US012797117B2

(12) United States Patent
Schifano et al.

(10) Patent No.: US 12,797,117 B2
(45) Date of Patent: Nov. 17, 2026

(54) METHOD AND IMPLANT SYSTEM FOR SACROILIAC JOINT FIXATION AND FUSION

(71) Applicant: Omnia Medical, LLC, Morgantown, WV (US)

(72) Inventors: Troy Schifano, Morgantown, WV (US); Steve Anderson, Folsom, CA (US); Teck-Mun Soo, Southfield, MI (US); Gowriharan Thaiyananthan, Irvine, CA (US)

(73) Assignee: OMNIA MEDICAL, LLC, Morgantown, WV (US)

( * ) Notice: Subject to any disclaimer, the term of this patent is extended or adjusted under 35 U.S.C. 154(b) by 0 days.

(21) Appl. No.: 17/745,896

(22) Filed: May 17, 2022

(65) Prior Publication Data

US 2022/0313334 A1 Oct. 6, 2022

Related U.S. Application Data

(63) Continuation of application No. 16/689,073, filed on Nov. 19, 2019, now abandoned, which is a
(Continued)

(51) Int. Cl.
*A61B 17/88* (2006.01)
*A61B 17/17* (2006.01)
(Continued)

(52) U.S. Cl.
CPC ...... *A61B 17/8872* (2013.01); *A61B 17/1757* (2013.01); *A61B 17/7055* (2013.01);
(Continued)

(58) Field of Classification Search
None
See application file for complete search history.

(56) References Cited

U.S. PATENT DOCUMENTS 1,032,897 A 7/1912 Hamilton
3,579,830 A 5/1971 Morel
(Continued)

FOREIGN PATENT DOCUMENTS

AU 728979 10/1998
AU 756550 5/2002
(Continued)

OTHER PUBLICATIONS

Giannikas, K. A., Khan, A. M., Karski, M. T., & Maxwell, H. A. (2004). Sacroiliac joint fusion for chronic pain: a simple technique avoiding the use of metalwork. European Spine Journal, 13(3), 253-256 accessed from "https://doi.org/10.1007/s00586-003-0620-1".

(Continued)

*Primary Examiner* — Tessa M Matthews
(74) *Attorney, Agent, or Firm* — McDonald Hopkins LLC

(57) ABSTRACT

An improved method of fusing the sacroiliac joint and tools for accomplishing the same is disclosed. In one embodiment, the present invention is a method that uses an intra-articular joint fusion device for connecting the sacrum and ilium that includes creating a first incision in the patient's skin proximal to the patient's sacroiliac joint, inserting a surgical channel tool into the incision from the patient's posterior, creating a void in the sacroiliac joint, inserting a fusion implant into the void, the fusion implant having at least one fixation element for engagement with bone tissue in the articular surfaces of the sacrum and the ilium, and driving the fusion implant into the void such that the at least one fixation element engages with bone tissue in an articular surface of at least one of the sacrum and ilium, and the fusion implant fixes relative positions of the sacrum and ilium.

5 Claims, 35 Drawing Sheets

Related U.S. Application Data continuation of application No. 14/668,976, filed on Mar. 25, 2015, now Pat. No. 10,993,757, which is a continuation-in-part of application No. 13/842,227, filed on Mar. 15, 2013, now Pat. No. 9,119,732.

(51) Int. Cl.

*A61B 17/70* (2006.01)
*A61B 17/86* (2006.01)
*A61F 2/30* (2006.01)
*A61F 2/44* (2006.01)
*A61F 2/46* (2006.01)
*A61B 17/16* (2006.01)

(52) U.S. Cl.

CPC ........ *A61B 17/8605* (2013.01); *A61B 17/869* (2013.01); *A61F 2/4455* (2013.01); *A61F 2/447* (2013.01); *A61F 2/4611* (2013.01); *A61B 17/1671* (2013.01); *A61F 2002/30785* (2013.01); *A61F 2002/30828* (2013.01); *A61F 2002/30904* (2013.01); *A61F 2002/30995* (2013.01)

(56) References Cited

U.S. PATENT DOCUMENTS

D264,125 S 4/1982 Biggs
4,481,020 A 11/1984 Lee et al.
4,569,338 A 2/1986 Edwards
4,927,421 A 5/1990 Goble et al.
D346,103 S 4/1994 Warner
5,334,205 A 8/1994 Cain
5,443,509 A 8/1995 Boucher et al.
5,534,031 A 7/1996 Matsuzaki et al.
5,649,946 A 7/1997 Bramlet
5,722,978 A 3/1998 Jenkins, Jr.
5,728,116 A 3/1998 Rosenman
5,741,261 A 4/1998 Moskovitz et al.
5,792,044 A 8/1998 Foley et al.
5,891,146 A 4/1999 Simon et al.
5,902,231 A 5/1999 Foley et al.
5,904,696 A 5/1999 Rosenman
5,954,635 A 9/1999 Foley et al.
6,007,487 A 12/1999 Foley et al.
6,053,916 A 4/2000 Moore
6,080,155 A 6/2000 Michelson
6,193,721 B1 2/2001 Michelson
6,206,822 B1 3/2001 Foley et al.
6,371,988 B1 4/2002 Pafford et al.
6,425,859 B1 7/2002 Foley et al.
6,436,098 B1 8/2002 Michelson
6,440,444 B2 8/2002 Boyce et al.
6,468,309 B1 10/2002 Lieberman
6,488,683 B2 12/2002 Lieberman
6,491,724 B1 12/2002 Ferree
6,520,907 B1 2/2003 Foley et al.
6,527,774 B2 * 3/2003 Lieberman ................ A61F 2/44 606/301
6,544,265 B2 4/2003 Lieberman
6,551,319 B2 4/2003 Lieberman
6,551,320 B2 4/2003 Lieberman
6,551,322 B1 4/2003 Lieberman
6,635,059 B2 10/2003 Randall et al.
6,648,917 B2 11/2003 Gerbec et al.
6,652,533 B2 11/2003 D'Neil
6,679,833 B2 1/2004 Smith et al.
6,689,153 B1 2/2004 Skiba
6,689,168 B2 2/2004 Lieberman
6,695,844 B2 2/2004 Bramlet et al.
6,770,074 B2 8/2004 Michelson
6,846,327 B2 1/2005 Khandkar et al.
6,953,462 B2 10/2005 Lieberman
6,991,656 B2 1/2006 Mears
7,018,416 B2 3/2006 Hanson et al.
7,125,425 B2 10/2006 Foley et al.
7,229,477 B2 6/2007 Biscup
D568,474 S 5/2008 Braunberger et al.
7,416,553 B2 8/2008 Patel et al.
D588,700 S 3/2009 Aldecoa
D593,202 S 5/2009 Petersen
7,575,572 B2 8/2009 Sweeney
7,601,167 B2 10/2009 Lieberman
D604,846 S 11/2009 Hintermann
7,648,509 B2 1/2010 Stark
D612,049 S 3/2010 Baynham
7,731,981 B2 6/2010 Trieu et al.
7,744,651 B2 6/2010 Trieu et al.
D620,111 S 7/2010 Courtney et al.
D620,115 S 7/2010 Pannu
D623,750 S 9/2010 Duffield et al.
D627,466 S 11/2010 Courtney et al.
D628,292 S 11/2010 Berberich
D629,104 S 12/2010 Calverley et al.
7,935,123 B2 5/2011 Fanger et al.
7,955,362 B2 6/2011 Erickson et al.
7,993,347 B1 8/2011 Michelson
7,993,378 B2 8/2011 Foley et al.
8,021,392 B2 9/2011 Petersen
8,025,684 B2 9/2011 Garcia-Bengochea et al.
D653,344 S 1/2012 Bar-Shalom
D653,756 S 2/2012 Courtney et al.
8,109,934 B2 2/2012 Guenther et al.
8,128,700 B2 3/2012 Delurio et al.
8,157,865 B2 4/2012 Hochschuler et al.
8,162,981 B2 4/2012 Vestgaarden
8,197,513 B2 6/2012 Fisher et al.
8,202,305 B2 6/2012 Reiley
8,221,428 B2 7/2012 Trieu
8,221,503 B2 7/2012 Garcia et al.
8,282,642 B2 10/2012 McClintock et al.
8,308,779 B2 11/2012 Reiley
8,328,815 B2 12/2012 Farr et al.
8,343,189 B2 1/2013 Assell et al.
8,348,950 B2 1/2013 Assell et al.
8,388,667 B2 3/2013 Reiley et al.
8,403,991 B2 3/2013 Ullrich, Jr. et al.
D685,087 S 6/2013 Voic
8,551,171 B2 10/2013 Johnson et al.
8,579,912 B2 11/2013 Isaza et al.
8,585,741 B2 11/2013 Gabelberger et al.
8,623,053 B2 1/2014 Vestgaarden
8,623,091 B2 1/2014 Suedkamp et al.
D704,334 S 5/2014 Walthall
8,740,912 B2 6/2014 Stark
D708,747 S 7/2014 Curran et al.
8,808,305 B2 8/2014 Kleiner
8,808,377 B2 8/2014 Donner
8,852,241 B2 10/2014 Datta
8,882,818 B1 * 11/2014 Vestgaarden ...... A61B 17/1662 623/17.11
8,945,224 B2 2/2015 Trieu
8,961,571 B2 2/2015 Lee et al.
8,979,928 B2 3/2015 Donner
9,017,407 B2 4/2015 Donner
D728,892 S 5/2015 Rogers et al.
9,039,774 B2 5/2015 Chataigner et al.
9,101,371 B2 8/2015 Assell et al.
9,113,972 B2 8/2015 Trudeau
9,119,732 B2 9/2015 Schifano et al.
9,149,286 B1 10/2015 Greenhalgh et al.
D742,187 S 11/2015 Thompson et al.
9,186,155 B2 11/2015 Katzman et al.
9,241,798 B2 1/2016 Petersen
9,247,943 B1 2/2016 Kleiner
9,375,243 B1 6/2016 Vestgaarden
9,381,045 B2 7/2016 Donner et al.
9,421,109 B2 8/2016 Donner
D765,855 S 9/2016 Ben-Yehuda et al.
9,451,986 B2 9/2016 Stoffman
9,492,284 B2 11/2016 Ginn et al.
9,498,349 B2 11/2016 Patterson et al.
9,662,128 B2 5/2017 Reiley
9,668,781 B2 6/2017 Stark

(56) References Cited

U.S. PATENT DOCUMENTS 9,700,356 B2 7/2017 Donner et al.
9,757,119 B2 9/2017 Norton et al.
9,757,154 B2 9/2017 Donner et al.
9,795,396 B2 10/2017 Donner
9,801,732 B2 10/2017 Chin et al.
9,808,346 B2 11/2017 Stark
9,833,321 B2 12/2017 Rindal
9,883,874 B1 2/2018 Vestgaarden
9,895,176 B2 2/2018 Vestgaarden
9,949,843 B2 4/2018 Reiley et al.
D816,469 S 5/2018 Toomey
9,999,430 B2 6/2018 Hirsch et al.
10,004,547 B2 6/2018 Reiley
D828,549 S 9/2018 Gonzalez
10,070,970 B2 9/2018 Lynn et al.
10,136,932 B2 11/2018 Freese
D835,787 S 12/2018 Radocy et al.
10,149,764 B2 12/2018 Stark
10,166,033 B2 1/2019 Reiley et al.
10,194,962 B2 2/2019 Schneider et al.
10,201,427 B2 2/2019 Mauldin
10,206,739 B2 2/2019 Godara et al.
10,219,841 B1 3/2019 Compton
10,219,912 B2 3/2019 Suh et al.
D846,976 S 4/2019 Williams
10,245,044 B2 4/2019 Petersen
10,245,087 B2 4/2019 Donner et al.
10,245,158 B2 4/2019 Song
10,254,044 B2 4/2019 Schindler et al.
10,265,176 B2 4/2019 Donner et al.
D847,994 S 5/2019 Asfora et al.
10,292,720 B2 5/2019 Donner
10,314,710 B2 6/2019 Donner et al.
10,321,945 B2 6/2019 Schifano et al.
10,342,577 B2 7/2019 Worrel
10,357,368 B2 7/2019 Aksu
10,363,140 B2 7/2019 Mauldin et al.
D857,897 S 8/2019 Loftus
10,426,539 B2 10/2019 Schifano et al.
10,492,802 B2 12/2019 Donner et al.
10,555,818 B2 2/2020 McConnell et al.
10,646,258 B2 5/2020 Donner et al.
10,660,763 B2 5/2020 Wilson et al.
10,682,150 B2 6/2020 Stark
10,736,752 B1 8/2020 Schifano et al.
10,744,003 B2 8/2020 Ryan et al.
10,751,196 B1 8/2020 Schifano et al.
10,765,532 B2 9/2020 Ashleigh et al.
10,779,958 B2 9/2020 Lins
D898,914 S 10/2020 Niver et al.
10,820,917 B2 11/2020 Sharifi-Mehr et al.
D905,232 S 12/2020 Schifano et al.
10,849,764 B2 12/2020 Moore et al.
10,893,861 B2 1/2021 Sauer
D919,087 S 5/2021 Schifano
D922,568 S 6/2021 Schifano et al.
11,033,291 B2 6/2021 Bright
D939,089 S 12/2021 Cao et al.
11,229,430 B2 1/2022 Souls et al.
D944,987 S 3/2022 Wang
D945,618 S 3/2022 Martinez et al.
D947,379 S 3/2022 Cao et al.
D952,147 S 5/2022 Schifano et al.
D954,940 S 6/2022 Vijayachandran et al.
2001/0000532 A1 4/2001 Michelson
2001/0031967 A1 10/2001 Nicholson et al.
2002/0022764 A1 2/2002 Smith et al.
2002/0055737 A1 5/2002 Lieberman
2002/0143400 A1 10/2002 Biscup
2003/0139648 A1 7/2003 Foley et al.
2004/0054414 A1 3/2004 Trieu et al.
2004/0073216 A1 4/2004 Lieberman
2004/0133279 A1 7/2004 Krueger et al.
2004/0215203 A1 10/2004 Michelson
2004/0228901 A1 11/2004 Trieu et al.
2005/0011975 A1 1/2005 Baltz
2005/0015092 A1 1/2005 Rathbun et al.
2005/0080422 A1 4/2005 Otte et al.
2005/0119754 A1 6/2005 Trieu et al.
2005/0159756 A1 7/2005 Ray
2005/0165420 A1 7/2005 Cha
2005/0240195 A1 10/2005 Axelson, Jr. et al.
2006/0054171 A1 3/2006 Dall
2006/0089633 A1 4/2006 L. Bleich et al.
2006/0089646 A1 4/2006 Bonutti
2006/0178673 A1 8/2006 Curran
2006/0189997 A1 8/2006 Guenther et al.
2006/0287854 A1 12/2006 Smolenski et al.
2007/0118224 A1 5/2007 Shah et al.
2007/0134343 A1 6/2007 Trieu et al.
2007/0156020 A1 7/2007 Foley et al.
2007/0156241 A1 7/2007 Reiley et al.
2007/0270879 A1 11/2007 Isaza et al.
2008/0009861 A1 1/2008 Stark
2008/0154275 A1 6/2008 Assell et al.
2008/0154374 A1 6/2008 Labrom
2008/0177266 A1 7/2008 Metcalf et al.
2008/0249569 A1 10/2008 Waugh et al.
2009/0024174 A1* 1/2009 Stark .................. A61B 17/7055
606/321
2009/0036927 A1 2/2009 Vestgaarden
2009/0076551 A1 3/2009 Petersen
2009/0088604 A1 4/2009 Lowry et al.
2009/0099610 A1 4/2009 Johnson et al.
2009/0105832 A1 4/2009 Allain et al.
2009/0216238 A1 8/2009 Stark
2009/0259261 A1 10/2009 Reiley
2009/0312763 A1 12/2009 McCormack
2010/0030065 A1 2/2010 Farr et al.
2010/0106194 A1 4/2010 Bonutti et al.
2010/0106200 A1 4/2010 Stark
2010/0131011 A1 5/2010 Stark
2010/0268228 A1 10/2010 Petersen
2010/0268279 A1 10/2010 Gabelberger et al.
2010/0312279 A1 12/2010 Gephart et al.
2011/0009869 A1 1/2011 Marino et al.
2011/0060375 A1 3/2011 Bonutti
2011/0098817 A1 4/2011 Eckhardt et al.
2011/0106261 A1 5/2011 Chin et al.
2011/0166575 A1 7/2011 Assell et al.
2011/0172494 A1 7/2011 Bass et al.
2011/0184518 A1 7/2011 Trieu
2011/0184519 A1 7/2011 Trieu
2011/0230966 A1 9/2011 Trieu
2011/0238181 A1 9/2011 Trieu
2011/0264229 A1 10/2011 Donner
2012/0022535 A1 1/2012 Mayer et al.
2012/0071978 A1 3/2012 Suedkamp et al.
2012/0078371 A1 3/2012 Gamache et al.
2012/0083883 A1 4/2012 Ginn
2012/0095560 A1 4/2012 Donner
2012/0116454 A1 5/2012 Edidin et al.
2012/0143334 A1 6/2012 Boyce et al.
2012/0158137 A1 6/2012 Pinczewski
2012/0191191 A1 7/2012 Trieu
2012/0253398 A1 10/2012 Metcalf et al.
2012/0259365 A1 10/2012 Richelsoph
2012/0271351 A1 10/2012 Vestgaarden
2012/0277801 A1 11/2012 Marik
2012/0296428 A1 11/2012 Donner
2013/0006368 A1 1/2013 Walsh et al.
2013/0018427 A1 1/2013 Pham et al.
2013/0035723 A1 2/2013 Donner
2013/0144343 A1 6/2013 Arnett et al.
2013/0172736 A1 7/2013 Abdou
2013/0173004 A1 7/2013 Greenhalgh et al.
2013/0211453 A1 8/2013 Lenke et al.
2013/0218215 A1 8/2013 Ginn et al.
2013/0238093 A1 9/2013 Mauldin et al.
2014/0031935 A1 1/2014 Donner et al.
2014/0081279 A1 3/2014 Kleiner
2014/0088707 A1 3/2014 Donner et al.
2014/0088711 A1 3/2014 Chin
2014/0094918 A1 4/2014 Vishnubholta et al.

(56) References Cited

U.S. PATENT DOCUMENTS

| | | | | |
|---|---|---|---|---|
| 2014/0100662 | A1 | 4/2014 | Patterson et al. | |
| 2014/0114423 | A1 | 4/2014 | Suedkamp et al. | |
| 2014/0135927 | A1 | 5/2014 | Pavlov | |
| 2014/0142700 | A1 | 5/2014 | Donner et al. | |
| 2014/0200618 | A1 | 7/2014 | Donner et al. | |
| 2014/0207191 | A1 | 7/2014 | Kornel | |
| 2014/0257408 | A1 | 9/2014 | Trieu et al. | |
| 2014/0277165 | A1 | 9/2014 | Katzman et al. | |
| 2014/0277204 | A1 | 9/2014 | Sandhu | |
| 2014/0277460 | A1 | 9/2014 | Schifano | |
| 2014/0336763 | A1 | 11/2014 | Donner et al. | |
| 2015/0012097 | A1 | 1/2015 | Ibarra | |
| 2015/0025534 | A1 | 1/2015 | Gordon et al. | |
| 2015/0057754 | A1 | 2/2015 | Reed et al. | |
| 2015/0073552 | A1 | 3/2015 | To | |
| 2015/0088200 | A1* | 3/2015 | Lins | A61B 17/7064 606/247 |
| 2015/0112444 | A1 | 4/2015 | Aksu | |
| 2015/0150683 | A1 | 6/2015 | Donner et al. | |
| 2015/0173805 | A1 | 6/2015 | Donner et al. | |
| 2015/0209087 | A1 | 7/2015 | Donner | |
| 2015/0230937 | A1 | 8/2015 | Voellmicke | |
| 2015/0250611 | A1 | 9/2015 | Schifano et al. | |
| 2015/0250612 | A1 | 9/2015 | Schifano et al. | |
| 2015/0328012 | A1 | 11/2015 | Hansell | |
| 2016/0030191 | A1 | 2/2016 | McLuen | |
| 2016/0175113 | A1 | 6/2016 | Lins | |
| 2016/0310197 | A1 | 10/2016 | Black et al. | |
| 2017/0209155 | A1 | 7/2017 | Petersen | |
| 2017/0245999 | A1 | 8/2017 | Ginn et al. | |
| 2018/0036017 | A1 | 2/2018 | Donner et al. | |
| 2018/0092748 | A1 | 4/2018 | Donner et al. | |
| 2018/0303624 | A1 | 10/2018 | Shoshtaev | |
| 2019/0021868 | A1 | 1/2019 | Ludwig | |
| 2019/0083271 | A1 | 3/2019 | Donner et al. | |
| 2019/0090888 | A1 | 3/2019 | Sand et al. | |
| 2019/0133613 | A1 | 5/2019 | Reiley et al. | |
| 2019/0183521 | A1 | 6/2019 | Li et al. | |
| 2019/0209011 | A1 | 7/2019 | Donner | |
| 2019/0254840 | A1 | 8/2019 | Gray et al. | |
| 2019/0262010 | A1 | 8/2019 | Cerundolo et al. | |
| 2019/0336292 | A1 | 11/2019 | Aksu | |
| 2019/0343640 | A1 | 11/2019 | Donner et al. | |
| 2020/0029979 | A1 | 1/2020 | Donner et al. | |
| 2020/0093612 | A1 | 3/2020 | Blain | |
| 2020/0138452 | A1 | 5/2020 | Gatrell et al. | |
| 2020/0138485 | A1* | 5/2020 | Kuwamura | A61F 2/30988 |
| 2020/0138589 | A1 | 5/2020 | Abbasi | |
| 2020/0179135 | A1 | 6/2020 | Castro | |
| 2020/0253619 | A1 | 8/2020 | Gregory | |
| 2020/0315811 | A1 | 10/2020 | Cryder | |
| 2020/0337856 | A1 | 10/2020 | Moore et al. | |
| 2020/0390566 | A1 | 12/2020 | Murray | |
| 2021/0015502 | A1 | 1/2021 | Sharifi-Mehr | |
| 2022/0031306 | A1 | 2/2022 | Hassan | |

FOREIGN PATENT DOCUMENTS

| | | |
|---|---|---|
| CN | 110123436 | 8/2019 |
| EP | 0374088 | 10/1989 |
| EP | 0663184 | 1/1995 |
| EP | 1290985 | 4/2008 |
| EP | 1328216 | 9/2009 |
| EP | 2877128 | 6/2018 |
| FR | 2727004 | 5/1996 |
| WO | 2006074422 | 7/2006 |
| WO | 2011087912 | 7/2011 |
| WO | 2011091349 | 7/2011 |
| WO | 2012174485 | 12/2012 |
| WO | 2013043584 | 3/2013 |
| WO | 2014146018 | 9/2014 |
| WO | 2017066443 | 4/2017 |
| WO | 2018195406 | 10/2018 |
| WO | 2019137626 | 7/2019 |

OTHER PUBLICATIONS

Cohen, S. P., Chen, Y., & Neufeld, N. J. (2013), Sacroiliac joint pain: a comprehensive review of epidemiology, diagnosis and treatment, Expert Review of Neurotherapeutics, 13(1), 99-116, accessed from "https://doi.org/10.1586/em.12.148".

Medtronic Sofamor Danek USA, Inc., Brochure for METRx® System Surgical Technique, 2004, available online at www.mtortho.com/public/metrxmicrost.pdf.

Si-Bone, Inc., Brochure for iFuse Implant System®, 2012, available online at http://si-bone.com/health_care_professionals/.

Google machine English translation of CN110123436 accessed on May 17, 2021 from https://patents.google.com/patent/CN110123436A/en?oq=CN110123436.

Google machine English translation of FR2727004 accessed on May 17, 2021 from https://patents.google.com/patent/FR2727004A1/en?oq=FR2727004.

Globus Medical Inc, Descritpion of SI-LOK® Sacroiliac Fixation System, accessed on Mar. 18, 2013 from "https://www.globusmedical.com/mis/240-si-lok".

Medtronic Inc., Description of Infuse bone Graft/LT-Cage Lumbar Tapered Fusion Device accessed on Mar. 18, 2013 from "www.medtroniccom/for-healthcare-professionals/products-therapies/spinal/bone-graft-options/infuse-bone-graft/index.htm".

Medtronic Sofamor Danek USA, Inc., Brochure for METRx® System Surgical Technique, 2004, available at "www.mtortho.com/public/metrxmicrost.pdf".

Minsurg Corporation, Description of TruFUSE® Procedure, accessed on Mar. 18, 2013 "www.minsurg.com".

Orthopedic Designs North America, Inc., Description of Talon® DistalFix® Femoral Nail System accessed on Mar. 18, 2013 from "www.odi-na.com".

Osteotech, Inc, Description of Xpanse® R Bone Insert, accessed on Mar. 18, 2013 from "www.osteotech.com".

Si-Bone, Inc., Brochure for iFuse Implant System®, accessed on Mar. 18, 2013 from "http://si-bone.com/health_care_professionals/".

Signus Medizintechnik Gmbh, Description of the DIANA system, access on Mar. 18, 2013 from "www.si-joint.net".

Medtronic Sofamor Danek, Inc., 510(k) premarket notification of intent to market MSB Sacroiliac Joint Fusion Device and response letter from the Department of Health and Human service, accessed Mar. 18, 2013 from "http://sijpain.com/wp-content/uploads/K110472.pdf".

Tedan Surgical Innovations, Description of Phantom TL Transverse Retractor Frame with locking conical connection, accessed on Mar. 18, 2013 from "www.tedansurgical.com".

VG Innovations, LLC, Descrption of the SiJoin™ sacroiliac implant, accessed on Mar. 18, 2013 from "www.vginnovations.com".

Zyga Technology, Inc., Description of the Slmmetry® sacroiliac joint fusion system, accessed on Mar. 18, 2013 from "www.zygatech.com".

Donner E.J. Sacroiliac joint fusion system, U.S. Appl. No. 61/335,947, filed Jan. 13, 2010.

LDR Holding Corporation, Description of the cage surgical implants, access on Mar. 27, 2015 from "http://www.ldr.com/products".

Alphatec Spine, Inc., Description of Alphatec Solus® Anterior Lumbar Interbody Fusion, accessed on Mar. 27, 2015 from "http://www.alphatecspine.com/products/thoracolumbar/solus.asp".

Muller et al., Bone screw, English Abstract of European Patent Publication of EP0374088, Jun. 20, 1990, European Patent Organization, accessed from "http://www.epo.org/searching/free/espacenet.html."

Rosenman, D., Spiral surgical tack, English Abstract of European Patent Publication EP0663184, Jul. 19, 1995 European Patent Organization, access from "http://www.epo.org/searching/free/espacenet.html".

LDR Holding Corporation, Description of the ALIF cage surgical impants, available on Mar. 27, 2015 from "http://us.ldr.com/portals/1/PDF/Products/ROI-A/Patientedmedianobliqueiraopf1reva09.pdf".

(56) References Cited

OTHER PUBLICATIONS

LDR holding corporation, Description of the Lateral Lumber cage surgical implants, accessed on Mar. 27, 2015 "http://us.ldr.com/portals/1/PDF/Products/AvenueLPatientEducationAVEPF1REVA082012.pdf".
LDR holding corporation, Description of the Cervical Cage surgical implants, accessed on Mar. 27, 2015 from "http://us.ldr.com/portals/1/PDF/Products/ROI-C/IR-CPF2REVA04.2012.pdf".
USPTO Non-patent literature Database Search 1, U.S. Appl. No. 13/842,227, filed Mar. 30, 2015.
USPTO Non-patent literature Database Search 2, U.S. Appl. No. 13/842,227, filed Mar. 30, 2015.

* cited by examiner

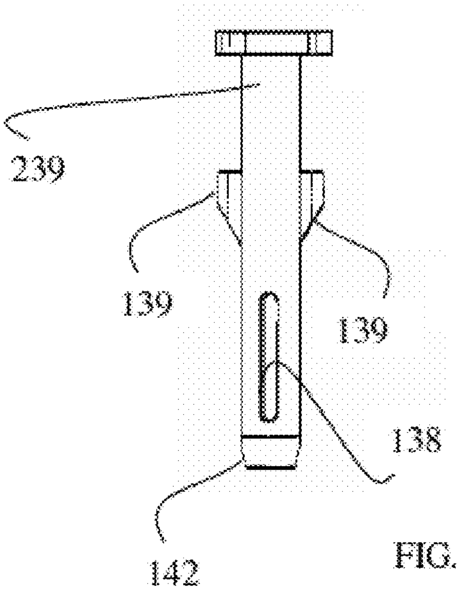
FIG. 28
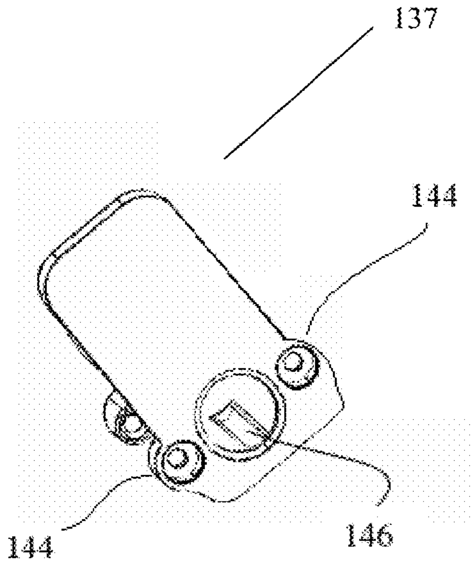
FIG. 29
FIG. 30
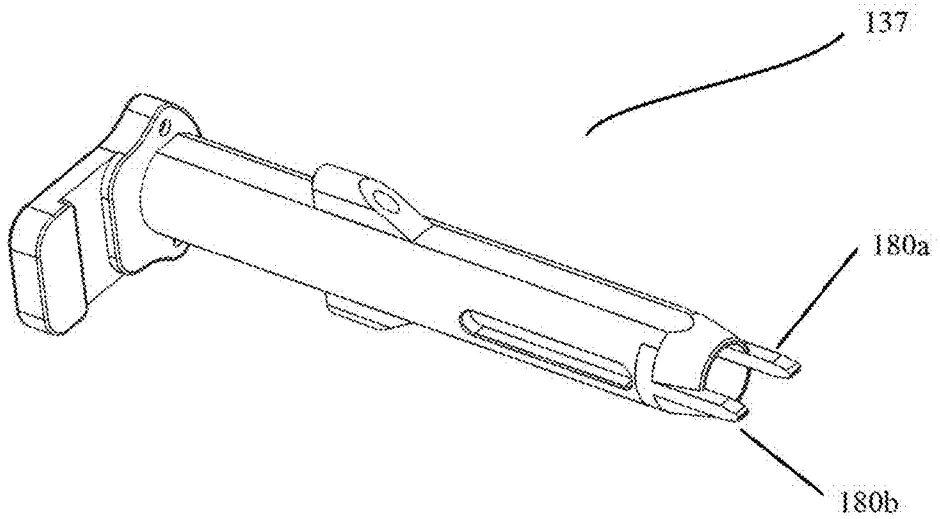

METHOD AND IMPLANT SYSTEM FOR SACROILIAC JOINT FIXATION AND FUSION

FIELD OF THE INVENTION

The present invention relates generally to medical devices and medical methods. More particularly, the present invention relates to musculoskeletal surgical methods and associated surgical tools for treatment of the sacroiliac joint.

DISCUSSION OF THE BACKGROUND

Lower back pain is a common ailment among the population and results in both pain and suffering as well as loss of work time. Thus, approaches for the treatment of back pain can both relieve suffering as well as reduce employee down time. Thus, effective treatments for lower back pain have both economic benefits as well as the benefit of alleviating considerable suffering.

The sacroiliac joint is located in the lower back at the juncture of the ilium, the upper bone of the pelvis, and the sacrum at the base of the spine. While the sacroiliac joint has a limited range of motion, dysfunction of the joint has been identified. The joint is supported by a range of ligaments including, for example, the sacroiliac ligament at the base of the joint and the anterior sacroiliac ligament at the top of the joint.

The sacroiliac joint (SI joint) is increasingly being diagnosed as a common pain generator. That is, SI joint degenerative disease and instability are being diagnosed and treated more commonly. Sacroiliac pain may be caused by a disruption in the joint itself, a biomechanical problem like a muscle imbalance, trauma, an inflammatory condition like ankylosing spondylitis, or a degenerative problem as seen with post-lumbar fusion adjacent segment disorder. Other contributing factors include post pregnancy pain/instability, longer life span, and/or more active lifestyles. In addition, complex spine surgeries, such as for correction of sagittal plane deformity, often require iliac fixation to maintain correction in patients with a high pelvic incidence or high risk of lumbo-sacral hardware failure.

High energy pelvic ring injuries that involve disruption of the SI joint and/or displaced fractures of the sacrum present unique challenges to the orthopedic traumatologist. Some sacral fractures require solid posterior stabilization, which may be difficult to achieve with typical treatment methods. Furthermore, vertically unstable sacral fractures/SI joint disruptions have a relatively high incidence of neurovascular injury and may require unique stabilization. Typically, a spinal surgeon will be involved to perform lumbo-pelvic stabilization of these injuries to provide vertical stability of the injury. However, there may be significant soft tissue trauma associated with these injuries, making extensive surgical approaches of elevated risk in terms of infection and wound complications.

Immobilization of the SI joint can result in significant relief of lower back pain. Current techniques and instrumentation systems may require extensive surgical exposure and dissection. Moreover, such instrumentation systems are typically designed for other applications, and not to connect and stabilize the lumbar spine and pelvis. As a result, this can make the surgical times longer and more frustrating for surgeons and surgical staff. For example, traditional posterior iliac screws are often prominent because the posterior iliac crest is relatively subcutaneous. Yet, this sometimes makes hardware painful for the patient and at risk for pressure soreness following surgery.

Furthermore, the current techniques and instruments do not allow for a secure and consistent fusion construct. They may provide one or the other many times, but not both issues. This may lead to further SI joint instability and a failed surgery.

It is therefore desirable to provide new surgical methods and tools for treating damaged sacroiliac joints that securely and consistently fuse the joint.

SUMMARY OF THE INVENTION

The present invention is an improved methods and devices for the immobilization or fusion of the Sacroiliac joint and apparatuses for facilitating the procedure. Immobilization may refer to mechanical holding or surgical fusion.

The present invention provides a system and surgical tools for introducing fusion implants that may perform the functions of mechanical fixation and stability, compression, and bony fusion. The present invention also relates to improved implant devices that may perform the functions of mechanical fixation and stability, compression, and bony fusion. The present invention also relates to methods of introducing fusion implants into a targeted joint through a novel exposure device. Specifically, with respect to some embodiments, an approach is described to address the SI joint through a posterior access approach while delivering fusion device that includes both a cavity or channel for graft or fusion-promoting material and fixation elements which can be in the form of helical anchors, claw or fluke anchors, blades, screws, and/or other fixation elements, which provide for compression across the sacroiliac joint. In some embodiments, a double barreled exposure device may be utilized to address the SI joint through a posterior approach while delivering both a fusion device to the SI joint and a separate fixation device for fixing the sacrum and ilium together, which can be in the form of a screw, or the like.

It is therefore an object of the present invention to provide an improved approach for both mechanical holding and surgical fusion through novel exposure devices described herein. The implants described herein may be introduced through a posterior approach to address the SI joint and the fusion device may perform the functions of fixation, compression, and bony fusion, providing a secure fixation element for mechanical stability and a bony fusion element that allows for fusion between the sacrum and the ilium.

It is also an object of the present invention to provide an improved, combined approach for both mechanical holding and surgical fusion using novel fusion devices that may be introduced through a novel exposure device through a posterior approach, while delivering a separate fixation device which can be in the form of a screw, or the like. Furthermore, the fusion device is delivered to the joint, placed between the sacrum and ilium, while the fixation device is delivered through the iliac wing, closest to the iliac crest, into the sacrum while not entering or going across the SI joint.

It is also an object of the present invention to provide novel fusion implants that are capable of performing perform the functions of fixation, compression, and bony fusion, allowing for stable fusion of the SI joint through a single posterior approach. However, such fusion implants may be used in combination with other devices to mechanically fix and stabilize the joint.

In some embodiments, the present invention relates to a fusion implant, comprising an elongate body adapted for placement in an intra-articular space between articular surfaces of a joint in general longitudinal alignment with a plane between the articular surfaces of the joint; at least one fixation element for engagement with bone tissue in at least one of the articular surfaces of the joint; and a cavity in the implant for holding a fusion-promoting material.

In some embodiments, the present invention relates to a medical instrument kit, including a joint fusion implant having a central body and at least one lateral fixation element for engagement with bone tissue in articular surfaces of a joint, and a surgical tool having a working channel for insertion into an incision (e.g., over a sacroiliac joint) in a human or animal, the working channel having a hollow barrel having a shape for receiving the joint fusion implant including the at least one lateral fixation element. The surgical tool may include at least one tang at the distal end thereof for insertion in a joint exposed by the incision, where the tang is operable to secure maintain a position of the working channel in the joint. In some implementations, and without limitation, the hollow barrel may have an oblong cross-sectional shape for accommodating the joint fusion implant and allowing the at least one fixation element to pass through the hollow barrel without obstruction, where the hollow barrel has a substantially uniform transverse cross section having a substantially elliptical shape and the elongate portions of the elliptical cross-section function as channels for receiving the at least one lateral fixation element. In some implementations, and without limitation, the hollow barrel may have at least one lateral slot running longitudinally along the hollow barrel to allow the at least one fixation element to pass through the interior passage without obstruction. In some embodiments, and without limitation, the surgical tool may further include a second working channel that is inserted into a second incision over an iliac wing of the human patient adjacent to the sacroiliac joint when the working channel is inserted into the sacroiliac joint. In some implementations, and without limitation, the working channel and the second working channel are connected by a connecting bar having a bend therein, and are connected at an acute angle that allows the working channel to be engaged with a posterior side of the sacroiliac joint and the second working channel to be engaged with a posterior portion of the iliac wing simultaneously. The kit may further include additional instruments to establish the working channels in the first and second incisions, and for introducing the fusion implant into the SI joint and a joint fixation device (e.g., a surgical screw) into the ilium and sacrum without traversing the SI joint, including a drill operable to be passed through the working channel into the incision and drilling a void through the connective tissues in the SI joint, as well as drill bits; an inserter having a proximal end configured to attach to the fusion implant, the inserter being operable to pass the fusion implant through the hollow barrel and into the joint; an impactor for driving the fusion implant into the joint, wherein driving the fusion implant engages the at least one fixation element with articular surfaces in the joint; joint cutting instruments; dilators; guide wires; guide pins; guide pin assemblies; a rasp; a box chisel; a driver for inserting surgical screws (e.g., a flex-shaft driver); adjustable arms for stabilizing the working channels; and other tools that may be utilized in establishing incisions and access to a joint or bone tissue.

In some embodiments, the present invention relates to a method including creating an incision proximal to the patient's SI joint, dilating the incision, engaging an exposure device with the incision, creating a void in the SI joint, and inserting and securing a joint fusing device in the void between the ilium and sacrum.

In some embodiments, the present invention relates to a method including creating an incision proximal to the patient's SI joint, creating an incision over iliac wing, dilating the incisions, engaging the exposure device with both incisions, creating a void in the SI joint, inserting a graft into the void, drilling a hole through the ilium and the S1 vertebra of the sacrum, and inserting a joint fusing device in the ilium and sacrum.

In some embodiments, the present invention relates to a method for repairing a sacroiliac joint of a patient that includes creating a first incision in the patient's skin proximal to the patient's sacroiliac joint; inserting a first working channel into the first incision and spreading the sacroiliac joint with an inserted end of the first working channel; creating a void in the sacroiliac joint; inserting a fusion implant into the void, the fusion implant having at least one fixation element for engagement with bone tissue in the articular surfaces of the sacrum and the ilium in the sacroiliac joint; creating a second incision in the patient's skin over an iliac wing of the patient adjacent to the sacroiliac joint; inserting a second working channel into the second incision wherein a longitudinal axis of the second working channel does not intersect the sacroiliac joint; and inserting a joint fixation device into the ilium and the sacrum through the second working channel, wherein the joint fixation device does not traverse the sacroiliac joint.

In some embodiments, the present invention relates to a method including preparing the patient for surgery (e.g., positioning the patient in a prone position to provide the surgeon access to the SI joint, general or local anesthesia, and the like), locating the SI joint and an incision point for access to the SI joint (e.g., by blunt finger palpation), insertion of a pin or wire to create an incision, insertion of a dilator over the pin and impacting the dilator to dilate the incision to a width through which instruments may be passed, inserting a working channel of an exposure device over the dilator, securing the working channel in position with fixing pins, removing the dilator, inserting a drill bit apparatus through the work channel, using the drill bit apparatus in the working channel to displace bone in the SI joint thereby creating a void, removing the drill bit apparatus, loading a joint fusion device into the first working channel until the joint fusion device is positioned proximal to the void in the patient's SI joint, inserting an impactor into the working channel and applying force to displace the graft into the void in the patient's SI joint, inserting a driver into the working channel, engaging the joint fusion device with the driver, and rotating the driver to rotate the joint fusion device such that anchoring devices on said joint fusion device engage with bone tissue of at least one of the sacrum and the ilium, removing all instruments, and closing the incision.

In some embodiments, the present invention relates to a joint fixation method including preparing the patient for surgery (e.g., positioning the patient in a prone position to provide the surgeon access to the SI joint, general or local anesthesia, and the like), locating the SI joint and an incision point for access to the SI joint (e.g., by blunt finger palpation), insertion of a pin or wire to create an incision, insertion of a dilator over the pin and impacting the dilator to dilate the incision to a width through which instruments may be passed, inserting a working channel of an exposure device over the dilator, securing the working channel in position with fixing pins, removing the dilator, inserting a drill bit apparatus through the work channel, using the drill bit apparatus in the working channel to displace bone in the SI joint thereby creating a void, removing the drill bit apparatus, excavating cortical bone tissue from articular surfaces within the joint, loading a joint fusion device into the first working channel until the joint fusion device is positioned proximal to the void in the patient's SI joint, inserting an impactor into the working channel and applying force to displace the joint fusion device into the void in the patient's SI joint, removing all instruments, and closing the incision.

In some embodiments, the present invention relates to a method of implanting a fusion device into a sacroiliac joint of a patient, including creating an incision in the patient's skin proximal to the patient's sacroiliac joint; using a joint probe to identify the sacroiliac joint; inserting a guide wire through a canal in the joint probe and into the sacroiliac joint; slotting a surgical channel device over the guide wire, the surgical channel device having a working channel; creating a void in the sacroiliac joint, wherein creating the void comprises displacing a portion of the patient's ilium and a portion of the patient's sacrum with an inserted end of the working channel, inserting a drill bit into the working channel, and drilling the void into the sacroiliac joint; inserting a fusion implant into the void, wherein the fusion implant includes a plurality of fixation elements and is configured to substantially compress, fix, and fuse the patient's ilium to the patient's sacrum; and engaging the fixation elements of the fusion implant with bone tissue in the articular surfaces of the patient's ilium and sacrum.

In some embodiments, the present invention relates to a method including preparing the patient for surgery (e.g., positioning the patient in a prone position to provide the surgeon access to the SI joint, general or local anesthesia, and the like), making a small incision over the top of the iliac wing from a posterior approach, locating the SI joint and an incision point for access to the SI joint (e.g., by blunt finger palpation), insertion of a pin or wire to create an incision, insertion of a dilator over the pin and impacting the dilator to dilate the incision to a width through which instruments may be passed, inserting a first working channel of a double-barreled, double-angled exposure device over the dilator and inserting a second working channel of said exposure device in the incision over the iliac wing, securing the first and second working channels in position with fixing pins, removing the dilator, inserting a drill bit apparatus through each of the first and second work channels, using the drill bit apparatus in the first working channel to displace bone in the SI joint thereby creating a void, using the drill bit apparatus (or a second drill bit apparatus) in the second working channel to drill a hole in the iliac crest and the S1 vertebra of the sacrum, removing the drill bit apparatus, loading a graft onto an inserter and inserting the graft and inserter into the first working channel until the graft is positioned proximal to the void in the patient's SI joint, inserting an impactor into the first working channel and applying force to displace the graft into the void in the patient's SI joint, inserting a joint fusion device coupled to a fusion device inserter into the second working channel and implanting said joint fusion device in the hole in the iliac crest and the sacrum, removing all instruments, and closing the incisions.

Additional objects of the invention will be apparent from the detailed descriptions and the claims herein.

BRIEF DESCRIPTION OF THE DRAWINGS

FIG. 28 is a side view of a surgical tool according to an embodiment of the present invention.

FIG. 29 is a top view of a surgical tool according to an embodiment of the present invention.

FIG. 30 is a perspective view of a surgical tool according to an embodiment of the present invention.

FIG. 120 is a posterior view of a pelvis with a surgical tool according to an embodiment of the present invention with two parallel barrels.

FIG. 121 is an enlarged posterior view showing two fusion implants inserted in an SI joint.

FIG. 122 is a posterior view of a pelvis with a surgical tool according to an embodiment of the present invention with two independent working channels, one inserted into an SI joint and one inserted over an iliac crest. The working channel inserted into the SI joint may have two barrels for the placement of two fusion devices in the SI joint.

FIG. 123 is an enlarged posterior view showing two fusion devices inserted in an SI joint and one fixation device in the ilium.

FIG. 124 is a superior view showing two fusion devices inserted in an SI joint and one fixation device in the ilium.

FIG. 125 is a posterior view of a pelvis with two surgical tools according to an embodiment of the present invention with a bilateral placement of the two surgical tools for the placement of bilateral implants.

FIG. 126 shows a perspective view of a fusion implant, according to an embodiment of the present invention.

FIG. 127 shows a side view of a fusion implant, according to an embodiment of the present invention.

FIG. 128 shows a cross-sectional view of a fusion implant, according to an embodiment of the present invention.

DETAILED DESCRIPTION

Figure 1:
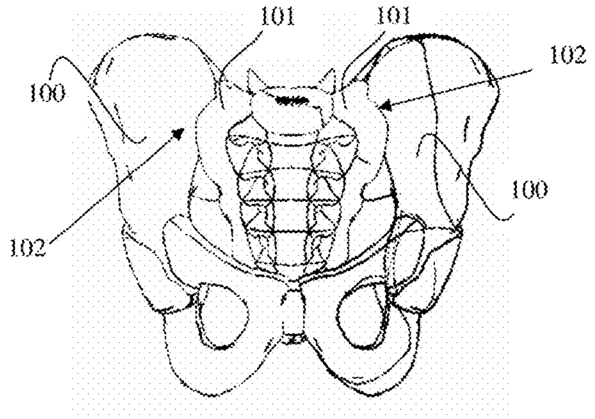
FIG. 1 is an anterior view of the bony anatomy of the pelvis and sacrum.

Reference will now be made in detail to certain embodiments of the invention, examples of which are illustrated in the accompanying drawings. While the invention will be described in reference to these figures and certain implementations and examples of the embodiments, it will be understood that such implementations and examples are not intended to limit the invention. To the contrary, the invention is intended to cover alternatives, modifications, and equivalents that are included within the spirit and scope of the invention as defined by the claims. In the following disclosure, specific details are given to provide a thorough understanding of the invention. References to various features of the "present invention" throughout this document do not mean that all claimed embodiments or methods must include the referenced features. It will be apparent to one skilled in the art that the present invention may be practiced without these specific details or features.

Reference will be made to the exemplary illustrations in the accompanying drawings, and like reference characters may be used to designate like or corresponding parts throughout the several views of the drawings.

The present invention relates to novel fusion implants and surgical tools designed for repairing a damaged or injured sacroiliac joint in a human patient, and methods for using such fusion implants and tools in procedures for repairing the damaged or injured sacroiliac joint. More specifically, the present invention pertains to a method for compressing, fixing, and fusing a damaged sacroiliac joint using a fusion implant having fixation element(s) (e.g., integrally formed fixation elements) and a channel or cavity for holding bone growth-promoting materials that provides for mechanical stability and promotes the formation of a contiguous piece of bone from the sacrum to the ilium. The fusion implants may be applied to the SI joint through a novel surgical tool (e.g., an exposure device) without the need for additional patient positioning or secondary surgery.

With respect to some embodiments, an approach is described to address the SI joint through a posterior approach while delivering a fusion implant device that may both compress and fix the SI joint and deliver bone growth-promoting material (e.g., autologous bone, allograft, BMP, etc.). The fusion implant may be delivered to the joint, placed between the sacrum and ilium, and one or more fixation elements (e.g., integral fixation elements) of the fusion implant may be engaged with bone tissue in the articular surfaces of the sacrum and ilium of the patient to thereby compress and fix the SI joint. In some embodiments, an additional fixation device may be delivered through the iliac wing and into the sacrum to assist in mechanically fixing the ilium and sacrum together, without the fixation device entering or traversing the SI joint.

An exemplary exposure device may include a working channel for guiding various surgical tools during a minimally invasive SI joint repair procedure. The surgical tool may allow the insertion of a fusion implant into the SI joint through the working channel in the surgical tool and guide the placement of the fusion implant into the SI joint. The tool enables a minimally invasive surgical method for repairing an SI joint that results in a secure, consistent, and reliable fusion of the SI joint. The surgical tool enables the insertion of the fusion implant into the SI joint while avoiding damage to the soft and connective tissues in and around the SI joint by closely controlling the placement of the fusion implant. The surgical tool may have a barrel or cannula through which the fusion implant is passed into the SI joint that has an interior perimeter shape that is complementary to and/or accommodative of the perimeter shape of the fusion implant. For example, and without limitation, the fusion implant may have lateral fixation elements (e.g., flukes or blades) for engaging with bone tissue in the articular surfaces of the sacrum and/or ilium within the sacroiliac joint, and the interior of the cannula or barrel may have an oblong or elliptical cross-sectional shape or lateral slots such that the lateral fixation elements of the fusion implant can be passed through the barrel or cannula without obstruction. The matching of the perimeter shapes of the interior of the barrel and the fusion implant may also allow the fusion implant to be properly oriented for placement in the SI joint. In some examples, and without limitation, the interior of the barrel may also include longitudinal notches that may be engaged with tabs or protrusions on the fusion implant in order to maintain proper orientation of the fusion implant within the barrel.

In some embodiments, the exposure device may include an additional working channel that is placed laterally to the SI working channel and over the iliac wing. The additional working channel may allow for the insertion of a fixation device (e.g., surgical screw) into the ilium and sacrum to aid in mechanically securing the SI joint. The additional channel may enable the insertion of a joint fixation device (e.g., a screw or other stabilizing device) into the ilium and sacrum such that the additional joint fixation device does not enter or traverse (pass through) the SI joint, thereby further avoiding damage to connective tissue of the SI joint.

Relevant Anatomy Description

Figure 2:
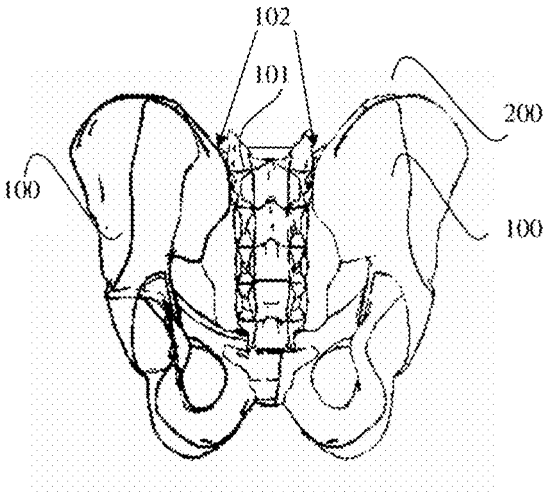
FIG. 2 is a posterior view of the bony anatomy of the pelvis and sacrum.
Figure 3:
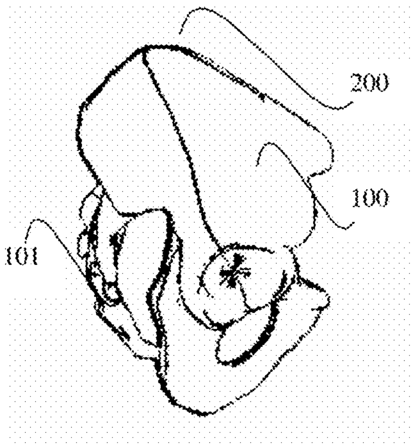
FIG. 3 is a right lateral view of the bony anatomy of the pelvis and sacrum.
Figure 4:
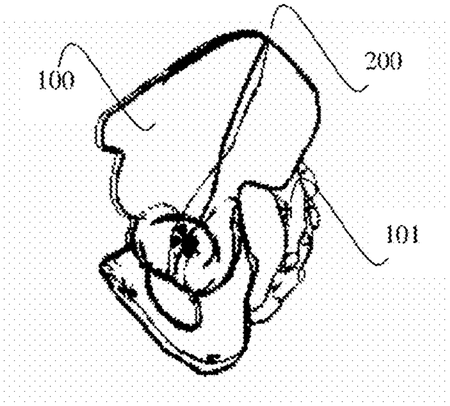
FIG. 4 is a left lateral view of the bony anatomy of the pelvis and sacrum.
Figure 5:
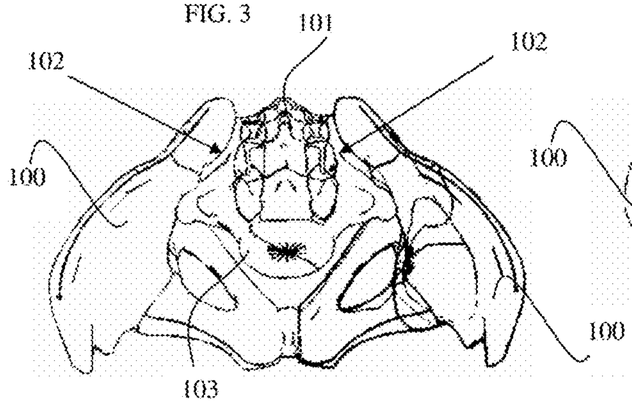
FIG. 5 is a superior view of the bony anatomy of the pelvis and sacrum.
Figure 110:
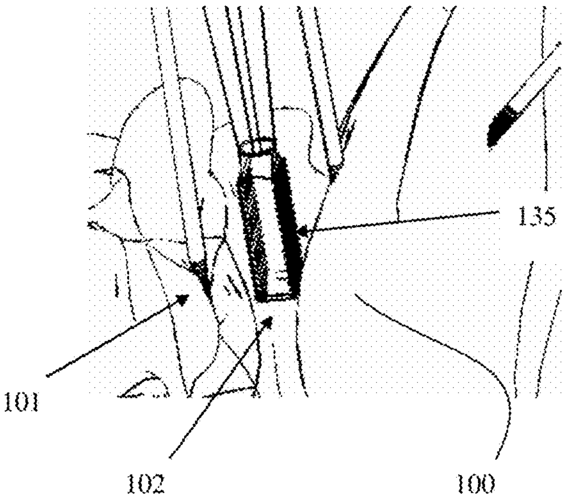
FIG. 110 is an enlarged oblique posterior view of a rasp inserted into an SI joint, with a working channel removed from view for clarity.
Figure 111:
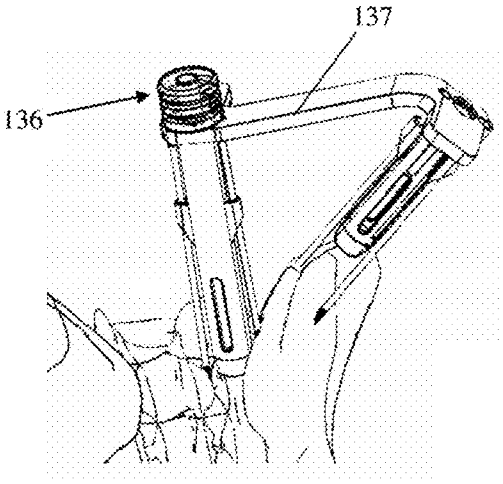
FIG. 111 is an oblique posterior view of a surgical tool according to an embodiment of the present invention engaged with an SI joint and the iliac wing with an impactor inserted into a working channel of the surgical tool.
Figure 112:
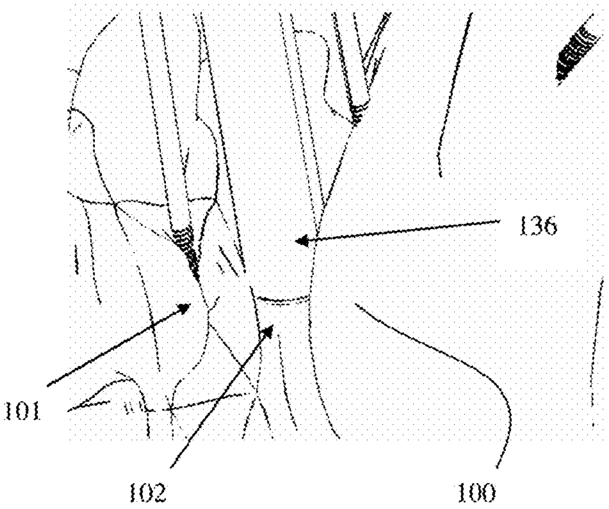
FIG. 112 is an enlarged oblique posterior view of an impactor inserted into an SI joint, with a working channel removed from view for clarity.

Referring to the drawings, FIG. 1 displays the bony anatomy of the sacrum and pelvis in a frontal, or anterior, view. The SI joint 102 is located between the ilium, or iliac wing, 100 and the sacrum 101 at the base of the pelvis 201. Additionally, the ridgeline of the articular process, the lateral ala 203 and the pedicle 104 of vertebrae S1 can be observed in this view. In FIG. 2, it can be seen that the SI joint 102 is not fully exposed for direct visualization from a rear, or posterior, viewpoint due to the angled and raised iliac crest 200 of the iliac wing 100. This angle provides a landmark for the entry point of the exposure device of the present invention at the posterior iliac crest. In FIG. 3 and FIG. 4, the prominence of the iliac crest 200 is displayed, along with the large surface area of the iliac wing 100, while the SI joint is fully enclosed between the iliac wing 100 and the sacrum 101 and occluded for direct visualization by the iliac wing 100. Again, the landmark of the posterior iliac crest can be seen. From a top down view, or superior view, the sacroiliac joint 102 can be fully observed between the iliac wing 100 and the sacrum 101, as shown in FIG. 5. Also shown in FIG. 5, the full sacrum 101 and specifically the vertebral body 103 of S1. The posterior superior iliac crest and the entry point of the S1 pedicle 104 can be observed in a direct line from one another (see also FIGS. 110-111).

Figure 6:
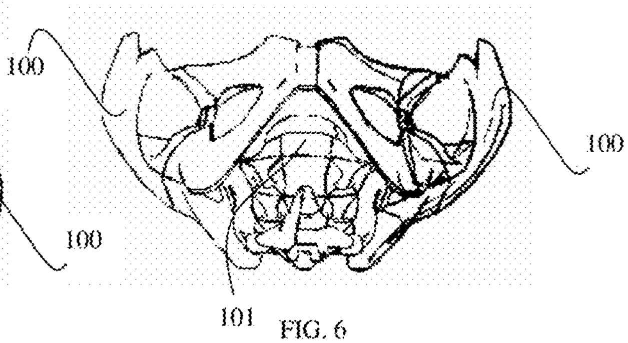
FIG. 6 is an inferior view of the bony anatomy of the pelvis and sacrum.

In FIG. 6, it can be again observed that the SI joint is occluded from direct visualization due to the anatomy of the sacrum 101, the ilium 100 and the pelvis 201. Therefore, the only direct visualization of the SI joint can be achieved through an anterior, superior or posterior-oblique view of the sacrum and pelvis. Due to major organs being present in the pelvic-sacral cavity (colon, rectum, bladder, etc.), an anterior or superior approach to the bony anatomy and, specifically the SI joint, presents an unreasonable risk. Lateral approaches can be performed as described in Published U.S. Pat. No. 5,334,205 to Cain, entitled "Sacroiliac Joint Fixation Guide," incorporated herein by reference and Published U.S. Pat. No. 8,221,428 to Trieu, entitled "Sacro-iliac joint implant system, method and instrument," incorporated herein by reference. However, these techniques rely on non-direct confirmation methods such as navigation and fluoroscopy to determine accurate landmark and sacroiliac joint locations.

Figure 7:
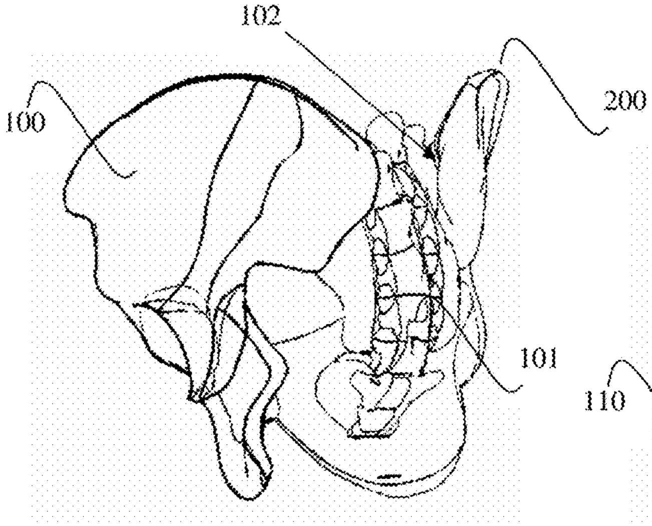
FIG. 7 is an oblique view of the right sacroiliac joint.
Figure 8:
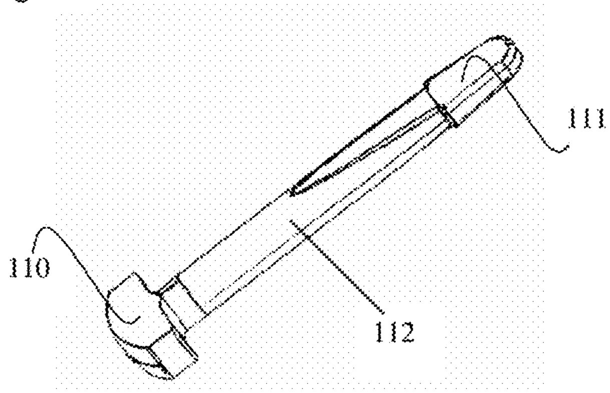
FIG. 8 is a perspective view of a joint probe.
Figure 9:
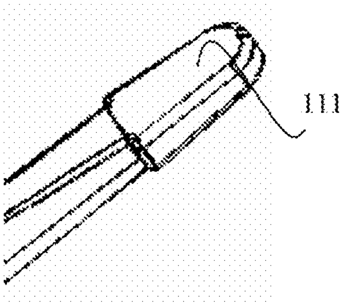
FIG. 9 is an enlarged view of the joint probe in FIG. 8.
Figure 10:
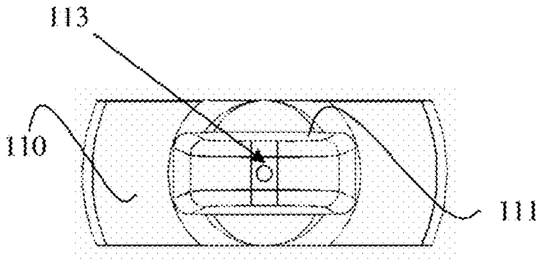
FIG. 10 is an end view of the joint probe in FIG. 8.

The present invention provides for novel surgical techniques and novel fusion implant and instrument designs which allow for a direct visualization of the SI joint by utilizing a posterior-oblique access method to the anatomy as displayed in the oblique view of FIG. 7. In this drawing, the SI joint 102 can be clearly viewed between the right ilium 100 and sacrum 101. A corresponding joint may be exposed through the same approach on the left hand side. Additionally, the anatomical landmark of the right posterior iliac crest and the corresponding access to the S1 pedicle 104 can be seen through this approach.

Instruments

The present invention utilizes a novel exposure device and a surgical tool kit that may be used in a novel surgical method to introduce and secure a fusion implant in a patient's SI joint. The present invention also relates to novel fusion implants that may be implanted into the SI joint, for example, by the novel surgical tools and methods of the present invention. Exemplary tools are described herein.

The novel exposure device may be a surgical guiding tool having a working channel therein for guiding other surgical tools for use in repairing an SI joint.

FIGS. 27-32B, show exemplary exposure devices 137 and 137*a* for accessing a sacroiliac joint is shown, having a working channel 239 that may be engaged with a posterior side of the sacroiliac joint. The working channels of the exposure devices may have a hollow barrel therein for passing various surgical tools that may have a shape corresponding to (complementary to) the hollow barrel. The working channel may provide a guide for inserting the various surgical tools into the SI joint, allowing precise surgical incisions, insertions of the fusion implant, etc. The barrel of the working channel may have an interior perimeter shape that is complementary to and/or accommodative of the perimeter shape of a fusion implant may be passed into the SI joint. The matching of the perimeter shapes of the interior of the barrel and the fusion implant may allow the fusion implant to be properly oriented for placement in the SI joint. For example, and without limitation, the exemplary exposure device 137 has a barrel having a substantially circular interior cross-section that may accommodate fusion implants that have circular cross-section (e.g., a helical implant) or a cross-section having a greatest diameter that is less than the diameter of the interior cross-section of the barrel.

In a further example, and without limitation, the barrel exposure device 137*a* may have an oblong or elliptical interior cross-section 190*a*, where the elongated portions of the barrel (e.g., the portions of the interior cross-section of the barrel that near the end of the major axis of the elliptical shape) act as channels through which lateral extensions of a fusion implant (e.g., a fusion implant having flukes or blades) may pass without obstruction. The interior of the barrel may have other shapes as well. For example, and without limitation, the interior perimeter of the barrel may have two lateral slots spaced at about 180° from one another in order to accommodate two lateral flukes, hooks, or blades extending from a body of an SI fusion implant. The working channel 239 may also have one or more pin guide slots 139 on one or more sides thereof for insertion of fixing pins to immobilize the exposure device 137 or 137*a* when it is engaged with the SI joint. In other implementations, and without limitation, a stabilizing arm (e.g., a retractor arm—not shown) may be engaged with a handle 140 and/or slot 141 in the handle in order hold the exposure device in a static and stable position.

The working channel 239 may have one or more windows 138 in the sides of the hollow barrel allowing the progress of a tool inserted therein to be observed through the one or more windows. For example, a surgical implement (e.g., a dilator) inserted into the hollow barrel of working channel 239 may have notches and/or unit markings on a side thereof that are visible through the one or more windows 138, allowing the progress and depth of the surgical implement to be precisely known. The windows 138 may also allow access to the surgical implements inserted into the working channel. If a surgical implement becomes difficult to remove during a surgical procedure due to the presence of fluid in the hollow barrel of the working channel (e.g., creating suction), appropriate tools can be used to access the surgical instrument through the window(s) 138 to aid in the removal of the surgical implement.

Referring to FIG. 29, the hollow barrel of the working channel 239 may have a slot 146 (e.g., a timing feature) that arrests the progress of a surgical implement inserted into the hollow barrel of the channel. The slot 146 prevents the surgical implement from advance too far into the SI joint or the ilium and sacrum, thereby preventing damage to the tissue of the patient. The surgical implements used in connection with the exposure device 137 may have a protrusion that is complementary to the slot 146, such that the slot is effective in controlling a depth to which the surgical implement can be inserted. The slot 146 also may ensure that such surgical implements having a complementary protrusion are and remain properly oriented in the hollow barrel of the working channel, with no axial movement, during the surgical procedure.

The hollow barrel of the working channel may also have guiding slots therein for properly aligning instruments (e.g., a fusion implant inserter, an impactor, etc.) and/or fusion implants for passage through the hollow barrel. The guiding slots may engage notches or protrusions on the instruments or implants such that the notches or protrusions slide along the guiding slots as the instrument or fusion implant is advanced through the hollow barrel. For example, and without limitation, guiding slots 146*a* are shown in the hollow barrel of exposure device 137*a* in FIG. 31. The guiding slots 146*a* are located at 180° relative to one another in the hollow barrel, but the invention is not limited to such an arrangement. Various implementations of the exposure device of the present invention may have one or more guiding slots (e.g., 1, 2, 3, etc.) and they may be arranged in various spatial arrangements within the hollow barrel.

The insertable end 142 of the working channel 239 may have a rounded circular or oblong geometry that prevents or reduces damage to the soft and connective tissues in and around the posterior side of the SI joint. Guide channels having other shapes (e.g., rectangular or square) may damage soft tissues around the SI joint when the guide channel is inserted therein. The round geometry of the insertable end 142 favorably reduces or prevents such damage. The round or circular insertable end 142 may also have a tapered or rounded profile, which may further aid in reducing or preventing damage to the soft and connective tissues around the SI joint. It is to be appreciated that the present invention is not limited to working channels having round, circular, or rounded ends. The working channels may have other perimeter shapes circular, oval, triangular, polygonal (pentagonal, hexagonal, etc.), Reuleaux shapes, and other applicable shapes.

Figure 32A:
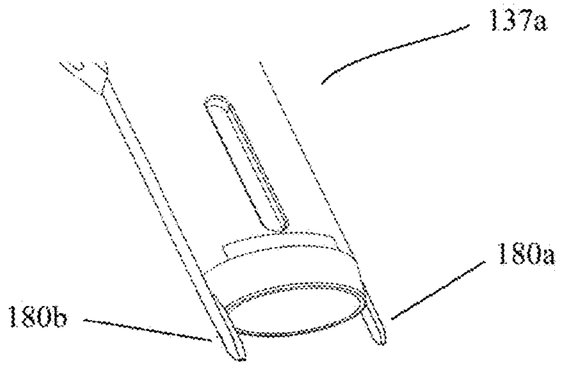
FIG. 32A is a close-up perspective view of the distal end of a surgical tool according to an embodiment of the present invention, where the surgical includes tangs at a distal end thereof.
Figure 32B:
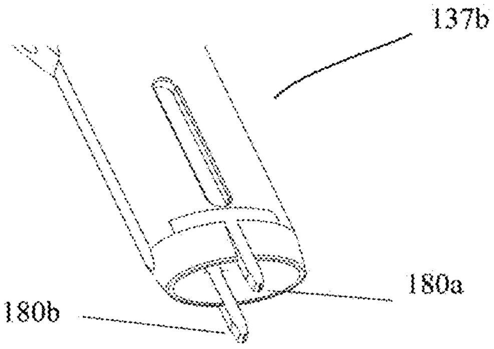
FIG. 32B is a close-up perspective view of the distal end of a surgical tool according to an embodiment of the present invention, where the surgical includes tangs at a distal end thereof.
Figure 33:
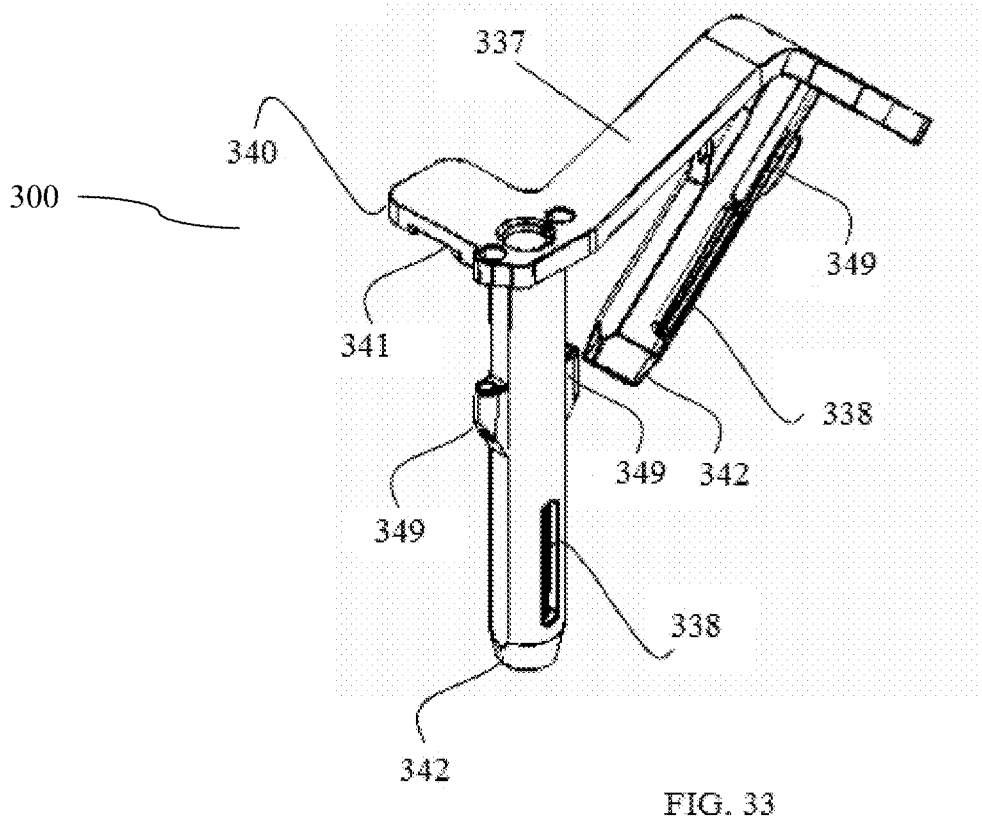
FIG. 33 is a perspective view of a surgical tool according to an embodiment of the present invention.
Figure 34:
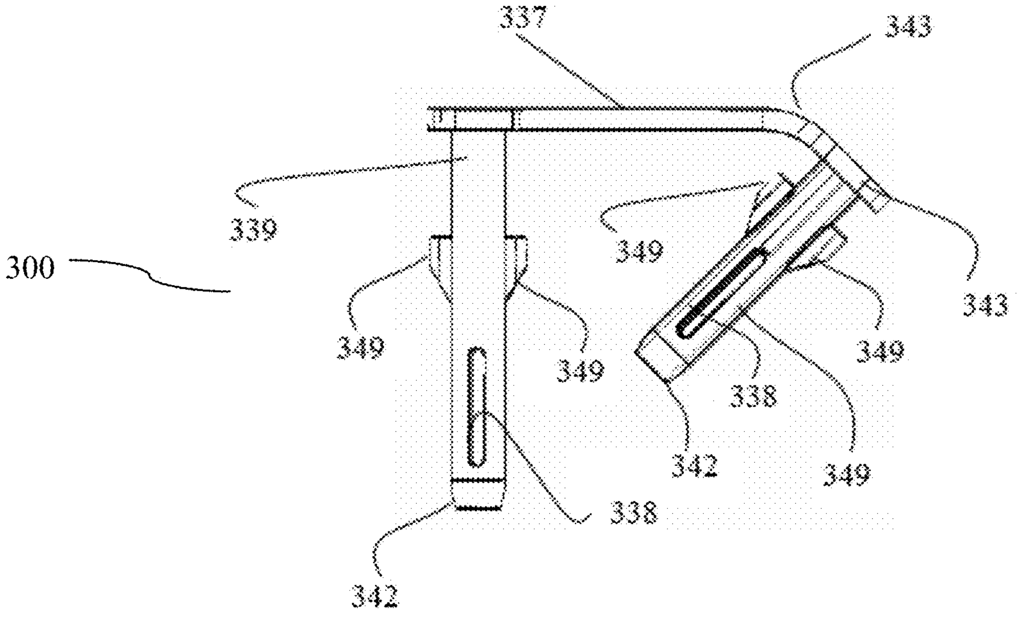
FIG. 34 is a side view of a surgical tool according to an embodiment of the present invention.

The insertable end of the working channel may also include one or more prongs or tangs that extend beyond the end of the hollow barrel. The one or more prongs or tangs may allow the working channel to be more easily centered in the SI joint (e.g., with the tangs aligned along the plane between the articular surfaces of the SI joint), and may also serve to help stabilize the position of the working channel in the SI joint. For example, and without limitation, FIGS. 30, 32A, and 32B show embodiments of an exposure device that includes tangs 180*a* and 180*b* extending from the distal, insertable end of exposure devices 137*b* and 137*b*. The tangs 180*a* and 180*b* are positioned 180° relative to one another on the end of the hollow barrel, but the invention is not limited to such an arrangement. In some embodiments (e.g., an embodiment exemplified by 137*b* shown in FIG. 32A), and without limitation, the tangs 180*a* and 180*b* may be included at the ends of the major axis of the oblong (e.g., elliptical) end of the working channel, which may be used with an implant having lateral fixation elements such as flukes that may be rotated into the bone tissue after being placed in the SI joint. In other embodiments (e.g., an embodiment exemplified by 137*c* shown in FIG. 32B), and without limitation, the tangs 180*a* and 180*b* may be included at the ends of the minor axis of the oblong (e.g., elliptical) end of the working channel, which may be used with an implant having lateral fixation elements such as lateral plates that may be inserted direct into the bone tissue of the SI joint.

The working channel may have other additional features such as handles 140 and slots 141 therein (e.g., for inserting handle extensions, etc.), as well. Additionally, the handle 140 may also be attachable to a stabilizing structure (e.g., a table or surgical arm, retractor/stabilizing arms, etc.) to prevent movement of the exposure device or surgical implements engaged therewith during surgical procedure. It is to be appreciated that the above description of the exposure tool does not limit the present invention, and other features are contemplated in and within the scope of the present invention.

In some embodiments the invention may comprise a double-barreled working channel having side by side (e.g., parallel) hollow barrels, each able to receive and guide surgical implements. The two barrels may have a same or different length. In reference to FIG. 120, a double-barreled working channel 295 may have first and second parallel barrels. Working channel 295 may allow multiple fusion implants to be inserted into an SI joint. In such embodiments, the additional working channel of the double-barreled working channel may have similar features as described above with respect to the working channel 239.

In some embodiments of the present invention, and without limitation, the exposure device may be a surgical guiding tool having two working channels therein for guiding other surgical tools for use in repairing an SI joint. The two working channels may be attached to one another by a connecting member, such as a bar or a rack. The bar may have a bend or angle therein that positions the two working channels at an angle (with respect to their longitudinal axes) relative to one another in a range of 0° to 180°. In some embodiments, the angle between the two working channels may be acute (e.g., about 30° to about 50°, or any angle in that range, such as about 45°). The angled positions of the two working channels allows one working channel to be positioned over the SI joint and the second working channel to be positioned over the ilium (e.g., the iliac wing) simultaneously and snugly, enabling the insertion of one more joint fusion implants into the SI joint and a joint fixation device (e.g., a bone screw) into the ilium and sacrum in a single procedure with a simple tool, without the need to reposition the surgical tool to insert either the joint fusion implants or the fixation device. In further embodiments, the relative angle of orientation of the two working channels may be a right angle or may be obtuse, depending on the desired insertion point on the ilium. If a different entry point for a joint fusion device is desired, the relative orientation angle of the two working channels may be in a range of about 45° to about 180° (e.g., about 90° to about 180°, about 45° to about 135°, about 90° to about 120°, or any value or range of values therein). For example, if the desired entry point on the ilium is more lateral or anterior, the angle of orientation between the two working channels may be 90° or greater.

Referring to FIGS. 33-37, a dual working channel exposure device 300 is shown having a connecting bar 337 connecting a first working channel 339 and a second working channel 350. The connecting bar 337 may have a bend or angle 343 between the first and second working channels 339 and 350. In some implementations, and without limiting the invention, the bend 343 may have an obtuse angle in a range of about 110° to about 160° (e.g., about 135° or any value therein). In some implementations, and without limiting the invention, the bend 343 may result in the first and second working channels being positioned at an acute angle relative to one another that may be complementary to the obtuse angle of the bend 343. In alternative implementations, and without limitation, the connecting bar may have a lockable joint therein between the first and second working channels 339 and 350 that may be adjusted to have an angle in a of about 90° to about 180° (e.g., about 135° or any value therein). The angle of the connecting bar 343 is configured to accommodate the contour of the pelvis between the ilium and the SI joint such that the first working channel 339 can be engaged with a posterior side of the sacroiliac joint and the second working channel 350 can be engaged with a posterior portion of the ilium simultaneously.

Figure 35:
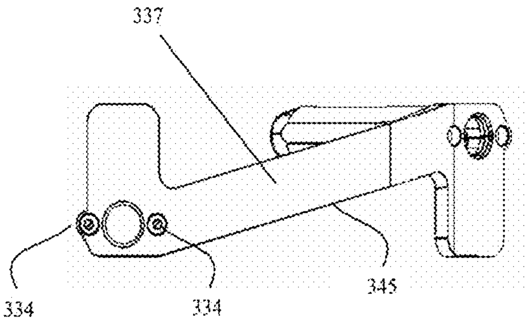
FIG. 35 is a top view of a surgical tool according to an embodiment of the present invention.
Figure 36:
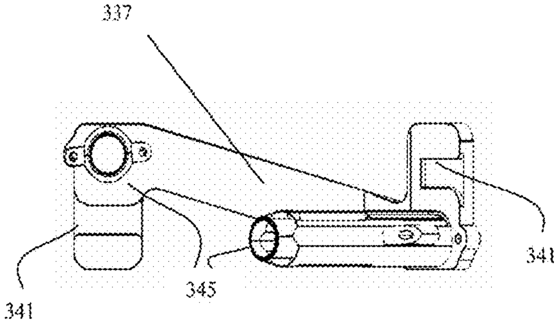
FIG. 36 is a bottom view of a surgical tool according to an embodiment of the present invention.

The connecting bar 337 may also have a second angle therein, as shown in the top perspective of FIG. 35 and the bottom perspective of FIG. 36. The first and second working channels 339 and 350 may be position at an angle between about 5° and about 40° (e.g., about 15°, or any angle therein). To further illustrate, the bar 343 may be angled such that the longitudinal axes of the first and second working channels 339 and 350 may run along different, but parallel planes. Thus, the working channels 339 and 350 are positioned at an acute angle relative to one another from a side perspective (e.g., FIG. 34), and on parallel planes relative to each other from top or bottom perspective (e.g., FIGS. 35 and 36). The additional angle in the connecting bar 343 may aid in positioning the second working channel 350 on the ilium when the first working channel is engaged with the SI joint, such that the second working channel 350 is positioned over the iliac wing, close to the iliac crest. The position and angle of the second working channel 350 may allow the insertion of a bone fusion device (e.g., a bone screw) through the ilium and the sacrum (e.g., the S1 vertebrae) through the hollow barrel of the second working channel 350, such that the bone fusion device does not traverse the SI joint (e.g., it is inserted anteriorly to the SI joint).

Each working channel may have a hollow barrel therein for passing various surgical tools that have a shape corresponding to (e.g., complementary to) the hollow barrel. The working channels provide a guide for inserting the various surgical tools into the SI joint and the ilium, allowing precise surgical incisions, insertions of fusion implants, bone-growth promoting material, etc. The working channel position over the SI joint may have a hollow barrel having an oblong or elliptical internal cross-section or other shape for accommodating fusion implants having one or more lateral fixation elements, as discussed above. Each of the first and second working channels 339 and 350 may have one or more pin guide slots 349 on a side thereof for insertion of fixing pins to immobilize the exposure device 300 when it is engaged with the SI joint and the ilium. The first and second working channels may also each have one or more windows 338 in sides of the hollow barrels allowing the progress of a tool inserted therein to be observed through the one or more windows, and allow access to instruments in the working channels through the windows, similarly to window 138 described above.

Figure 37:
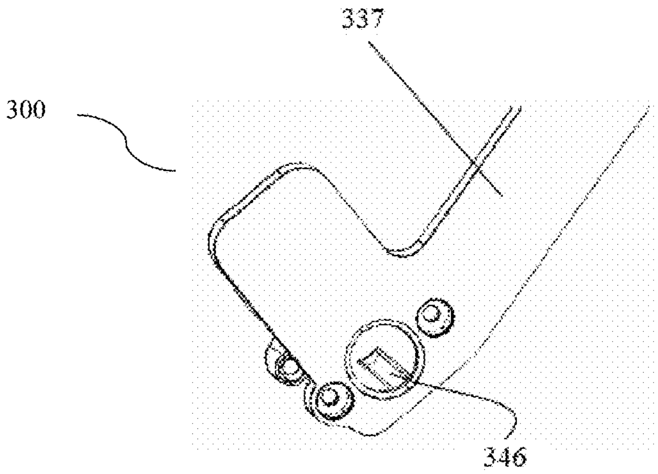
FIG. 37 is an isolated, top view of a surgical tool according to an embodiment of the present invention.

Referring to FIG. 37, the hollow barrels of the first and second working channels 339 and 350 may have a slot 346 (e.g., a timing feature) that arrests the progress of a surgical implement inserted into the hollow barrel of the channel. The slot 346 may prevent the surgical implement from advance too far into the SI joint or the ilium and sacrum and may ensure that surgical tools passed through the hollow barrels remain properly oriented, with no axial movement, thereby preventing damage to the tissue of the patient. The surgical implements used in connection with the dual working channel surgical tool may have a protrusion that is complementary to the slot 346, such that the slot is effective in controlling a depth to which the surgical implement can be inserted.

The insertable end 342 of the first working channel 339 may have a round or circular geometry that prevents or reduces damage to the soft and connective tissues in and around the posterior side of the SI joint. The round or circular insertable end 342 may also have a tapered or rounded profile, which may aid in reducing or preventing damage to the soft and connective tissues around the SI joint. The second working channel 350 may also have circular and/or rounded or tapered insertable end 342, as well. It is to be appreciated that the present invention is not limited to working channels having round, circular, oblong or otherwise rounded ends. The insertable end of the working channel 339 may also include one or more prongs or tangs that extend beyond the end of the hollow barrel, as discussed above. The one or more prongs or tangs may allow the working channel to be more easily centered in the SI joint (e.g., with the tangs aligned along the plane between the articular surfaces of the SI joint), and may also serve to help stabilize the position of the working channel in the SI joint.

The first and second working channels may have other additional features such as handles 340 and slots 341 therein (e.g., for inserting handle extensions), as well. It is to be appreciated that the above description of the surgical tool does not limit the present invention, and other features are contemplated in the present invention.

In some embodiments the invention may comprise one or more separate working channels that may be used in a similar manner to the dual working channel exposure device. In reference to FIG. 119, the invention may include first and second working channels 290, which can be individually positioned, for example, with one inserted into the posterior of the SI joint, and another positioned over the iliac wing. In such embodiments, the individual working channels may have the same features described above with respect to the dual working channel exposure devices described herein, except for the connecting bar 343 and the features particular thereto.

In some embodiments, the invention may include a kit or set of surgical implements and one or more joint fusion implants and joint fixation devices (e.g., surgical screws) that are associated with one or more of the exposure devices described above. Various tools may be included in such a set, including a joint cutting instrument (e.g., dilator), guide pins, guide pin assemblies, a drill, drill bits, a rasp, a box chisel, an inserter, and an impactor. Each of such tools may correspond to the exposure devices described herein. For example, the joint cutting instrument, the drill bits, the rasp, the box chisel, the inserter, and the impactor each may have a shape that is complementary to a hollow barrel of the exposure device, allowing each instrument to be inserted into the hollow barrel flush and in the proper orientation, without room to deviate from the path of the barrel. Thus, the working channel of the exposure device may act as precise guides for the surgical implements described above.

These surgical implements may be made of any suitable material, including medical grade plastics, metals, or alloys. In some embodiments, and without limitation, the tools are single use, in other embodiments the tools may be reused (and autoclaved, cleaned or otherwise suitably disinfected for further use). The tools may have various configurations, including those that differ from those depicted and specifically described herein.

The implements may include a joint probe capable of being used to locate an insertion point in an SI joint for a fusion implant. The joint probe may have a hollow channel therethrough for inserting a guide wire into the SI joint once the joint probe is properly positioned in the insertion point. Referring to FIGS. 8-11, the joint probe may have a rounded tip 111 for locating the insertion point, a shaft 112, and a handle 110. A hollow channel 113 run through the length of the joint probe to allow a guide wire to be inserted therethrough and into the SI joint.

Figure 11:
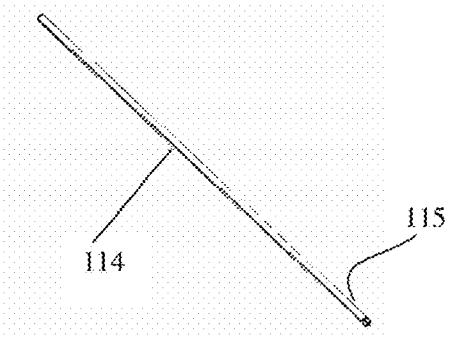
FIG. 11 is a perspective view of a guide pin.
Figure 12:
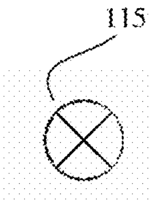
FIG. 12 is an end view of the guide pin in FIG. 11.
Figure 13:
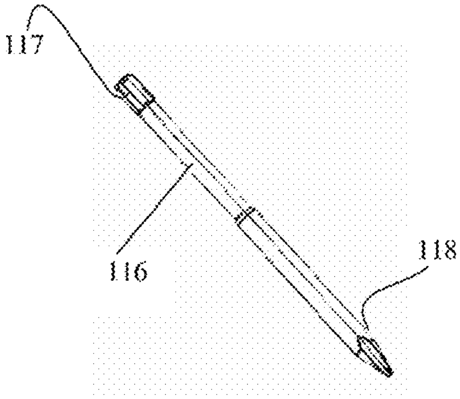
FIG. 13 is a perspective view of a joint cutting instrument.
Figure 14:
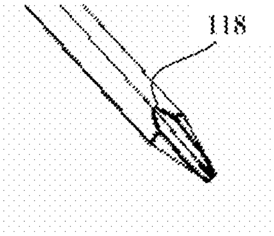
FIG. 14 is an enlarged view of the joint cutting instrument in FIG. 13.
Figure 15:
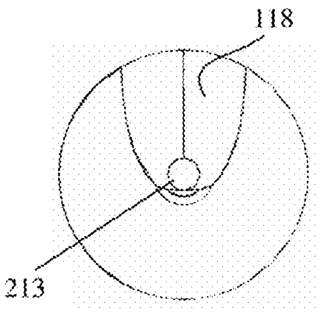
FIG. 15 is an end view of the joint cutting instrument in FIG. 13.
Figure 16:
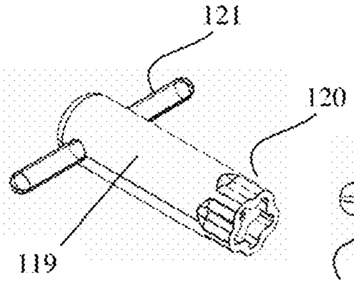
FIG. 16 is a perspective view of a t-handle addition for a joint cutting instrument.
Figure 17:
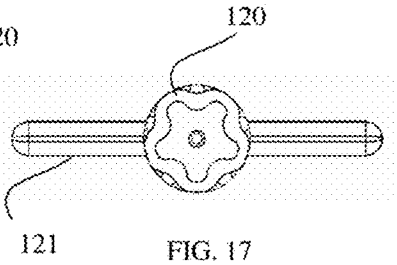
FIG. 17 is an end view of the t-handle addition in FIG. 16.

The set of tools may also include guide pins for securing the exposure device to the SI joint and the ilium. Referring to FIGS. 11-12, the guide pin 115 may have shaft that corresponds to the central channel of the joint probe and may be inserted into the SI joint through the dilator, to guide tools and implements subsequently positioned in said SI joint.

Figure 18:
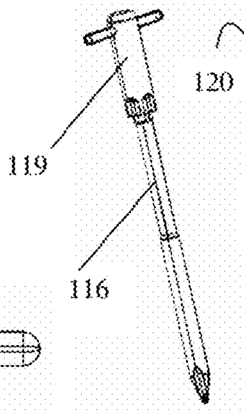
FIG. 18 is a perspective view of a joint cutting assembly.
Figure 19:
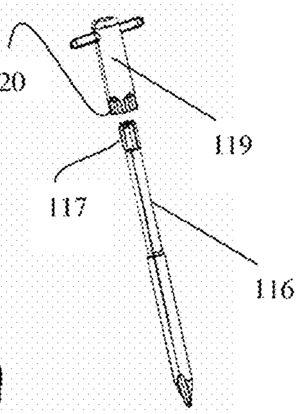
FIG. 19 is an exploded, perspective view of the joint cutting assembly in FIG. 18.

The set of surgical implements may include a dilator, which may be any device or structure capable of dilating an incision made in a human or other animal. FIGS. 13-19 illustrate an example of a dilator system that may be included in the present invention. Dilator 116 may be made of any suitable material and may have any suitable dimensions and configuration. In the depicted example, dilator 116 has a distal end 117, a proximal end 118, and a shaft therebetween. Proximal end 118 may have any configuration suitable to dilate an opening or incision, for example an incision made by a pin or wire in the patient's flesh and dilate that incision to increase its size. The proximal end 118 may be tapered, coming to a point at its end. The distal end 117 may be faceted, allowing it to be engaged with a grooved end 120 of a T-handle 119. A dilator assembly, an example of which is shown in FIGS. 18 and 19, allows the dilator to be spun or otherwise manipulated to adjust the size of an incision. The dilator 116 (and the t-handle 119) may have a central channel 213 running down its length that may allow a guide wire or pin to be inserted therethrough into the incision.

Figure 22:
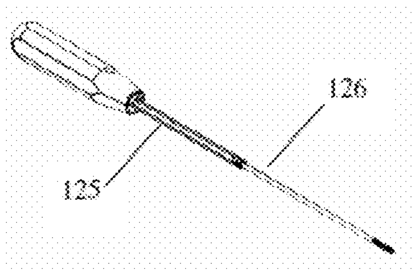
FIG. 22 is a perspective view of a fixation pin insertion assembly.
Figure 23:
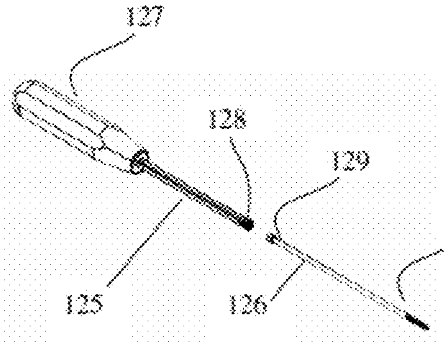
FIG. 23 is an exploded, perspective view of the fixation pin insertion assembly in FIG. 22.

Fixing pins 126 and a fixing pin handle 125, as shown in FIGS. 22-23, may be included in the set of tools that correspond to the pin guide slots 139 on sides of the working channels of the exposure devices. The guide pins may also have a sharp and/or threaded end 115 for piercing bone and other tissues. The fixing pins may correspond to the pin guide holes on sides of the working channels (e.g., pin holes 139, and 349) of the exposure devices described above. The fixing pins can be used to secure the working channels in a desired position over the SI joint or the ilium.

Figure 20:
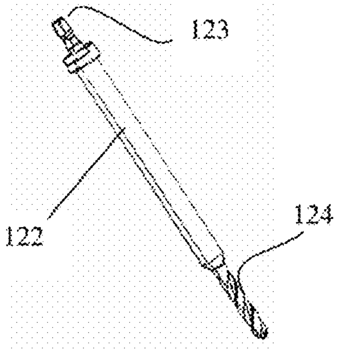
FIG. 20 is a perspective view of a drill bit.
Figure 21:
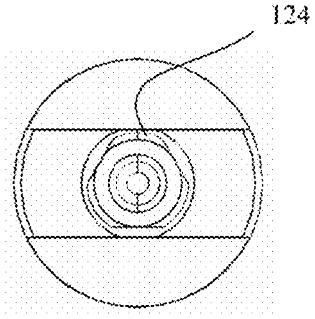
FIG. 21 is an end view of the drill bit in FIG. 20.

A drill 122, as shown in FIGS. 20-21, may be included in the set to allow for bone preparation for fusion implant insertion. The drill may have a thread portion 124 with numerous designs in order to provide a hole with the desired female thread cut in the desired anatomy. The drill may also be designed to be attached to power instruments, a hand drill or a handle. Without limiting the invention, FIG. 20 an exemplary drill having a Jacob's chuck connection 123 so that it may be attached to a powered drill for quick preparation. Additionally, the drill may have a central channel 124 running down its length that may allow a guide wire or pin 114 to be inserted there through into the incision as seen in FIG. 21.

Figure 24:
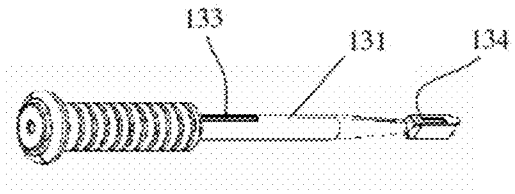
FIG. 24 is a side view of a box chisel.

A chisel 131, as shown in FIG. 24, may be included in the set to provide an opening in the bone with desired dimensions on its distal tip 134 to better facilitate entry for the fusion implant. The distal tip 134 may have a tapered nose in order to self-distract its way in between the sacrum and ilium. The distal tip 134 may also have cutting edges to dig into the bone and remove it from the surgical site. The chisel may be used to penetrate the cortical tissue of the sacrum and ilium to allow anchoring portions of the joint fusion implants of the present invention to penetrate the bone tissue and thereby anchor the fusion implant in the joint. The distal tip 134 may also have a containment device for removal of surgical site bone and windows may exist in the containment device to collect bone debris and remove the bone debris after removal from surgical site. The distal tip 134 may be undersized to a fusion implant to be inserted in order to ensure full bony contact on all sides of the fusion site. The chisel may have an outer diameter, as seen in FIG. 24, that matches the inner diameter of a working channel (e.g., working channels 239, 339, and 350) to keep the chisel directed in an axial plane for desired implant preparation. The chisel may have a timing feature 133 that mates with a female timing feature (e.g., timing feature 146 or 346) on the inside of a working channel to keep the chisel from plunging too far into the surgical site and to further keep the chisel in the proper orientation for desired implant site preparation.

Figure 25:
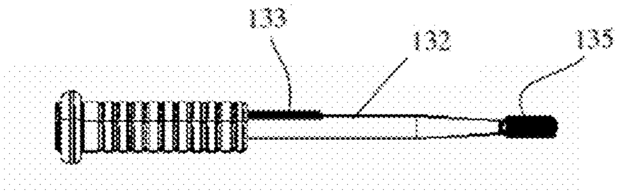
FIG. 25 is a side view of a rasp.

Additionally, a rasp 132, as shown in FIG. 25, may be included in the set to provide an opening in the bone with desired dimensions on its distal tip 135 to better prepare the bone for a fusion site for the fusion implant. The distal tip 135 may have a tapered nose in order to self-distract its way in between the sacrum and ilium. The distal tip 135 may have aggressive teeth which can scrape the bone to help prepare the bone surface for receiving anchoring portions of joint fusion implants of the present invention. The rasp may have an outer diameter as seen in FIG. 25, that matches the inner diameter of a working channel (e.g., working channels 239, 339, and 350) to keep the rasp directed in an axial plane for desired implant preparation. The rasp may have a timing feature 133 that mates with a female timing feature (e.g., timing feature 146 or 346) on the inside of a working channel to keep the instrument from traveling too far into the surgical site and to further keep the instrument in the proper orientation for desired implant site preparation.

Figure 26:
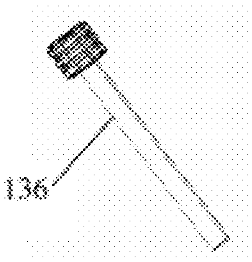
FIG. 26 is a perspective view of a bone graft impactor.
Figure 27:
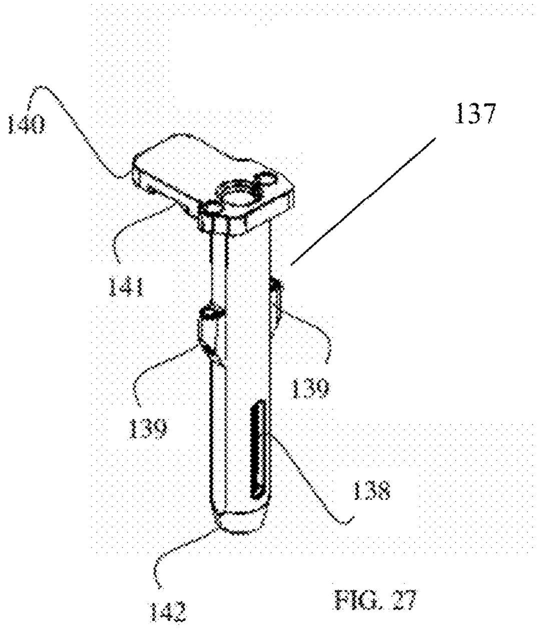
FIG. 27 is a perspective view of a surgical tool according to an embodiment of the present invention.
Figure 31:
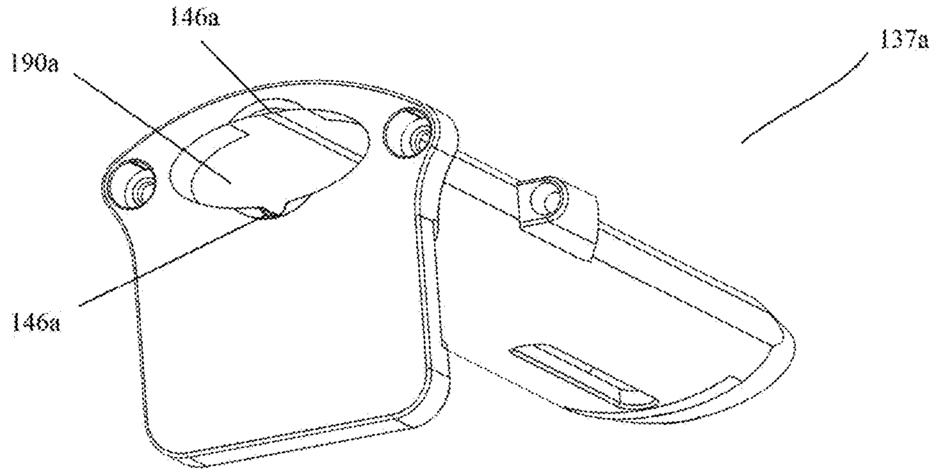
FIG. 31 is a perspective view of a surgical tool according to an embodiment of the present invention.

One or more impactors, such as impactor 136 shown in FIG. 26, may be included in the surgical implements, as well. The impactor may have a cylindrical proximal end, like a hammer. The impactor may be included in the set to facilitate secondary impaction and movement of a fusion implant and, optionally, to advance bone-fusion promoting materials in the SI joint in front of and/or behind the implant to better prepare the surgical site and to promote fusion of the SI joint. The impactor may have an outer diameter, as seen in FIG. 26, that matches the inner diameter of a working channel (e.g., working channels 239, 339, and 350) to keep the instrument directed in an axial plane for desired surgical site preparation.

Figure 38:
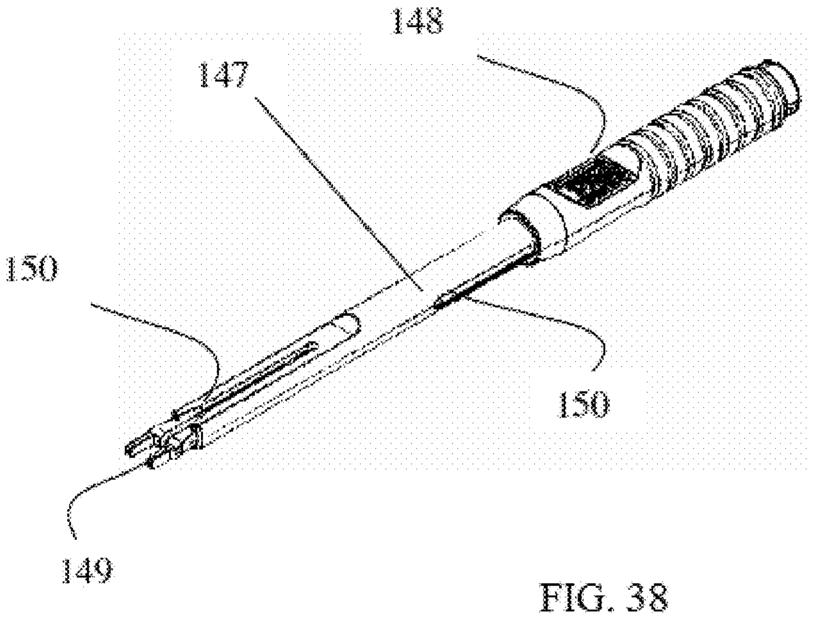
FIG. 38 is a perspective view of a fusion implant inserter for use with a surgical tool according to an embodiment of the present invention.
Figure 39:
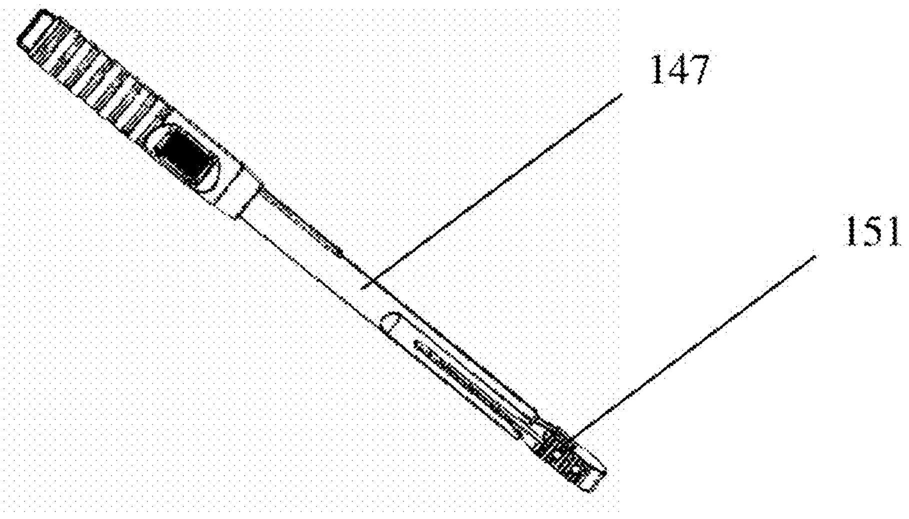
FIG. 39 is a perspective view of a fusion implant inserter engaged with a fusion implant for use with a surgical tool according to an embodiment of the present invention
Figure 40:
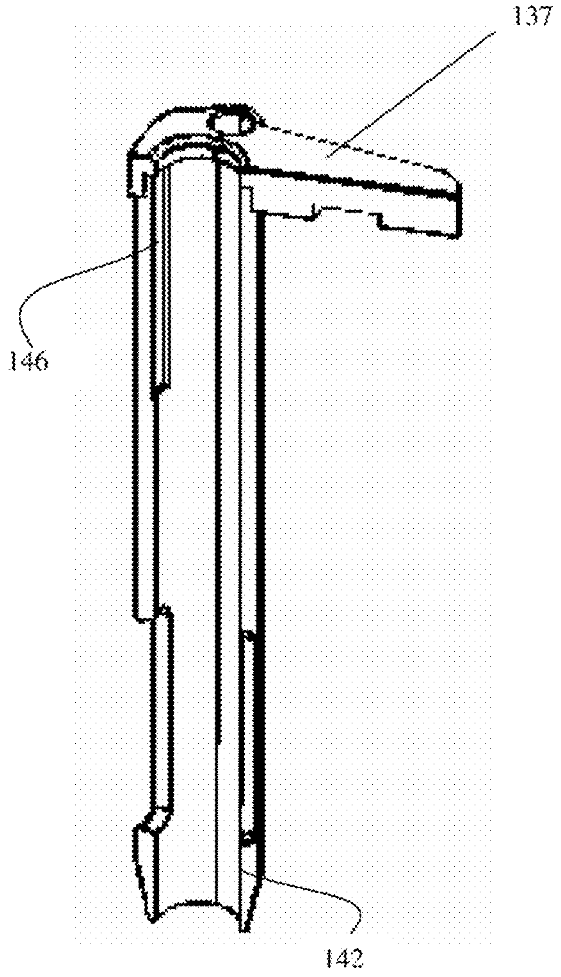
FIG. 40 is a cross sectional view of one barrel of a surgical tool according to an embodiment of the present invention.
Figure 41:
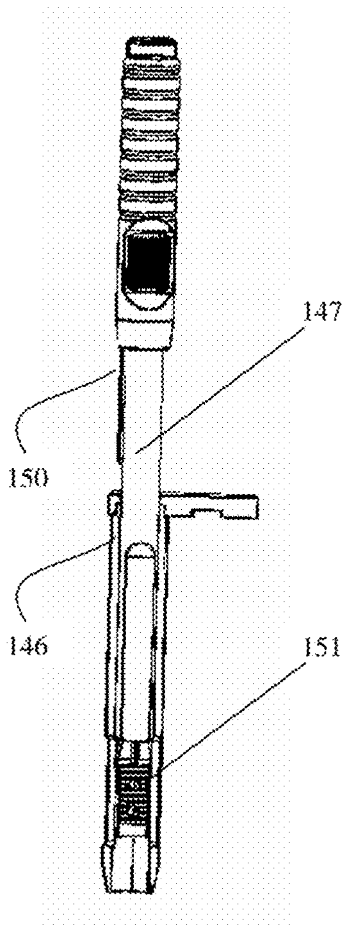
FIG. 41 is a cross sectional, side view of one barrel a surgical tool according to an embodiment of the present invention engaged with a fusion implant inserter.
Figure 42:
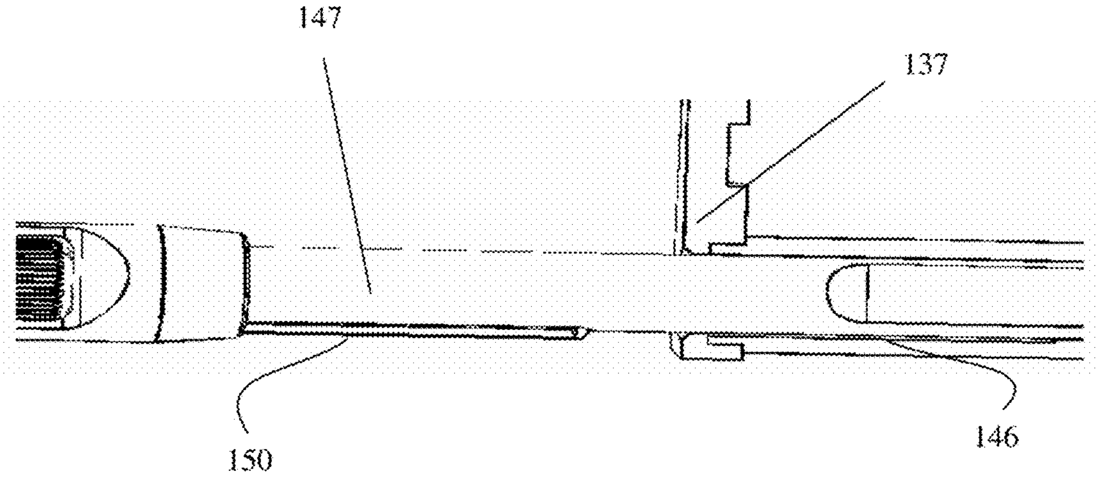
FIG. 42 is a cross sectional, side view of one barrel a surgical tool according to an embodiment of the present invention engaged with a fusion implant inserter.
Figure 43:
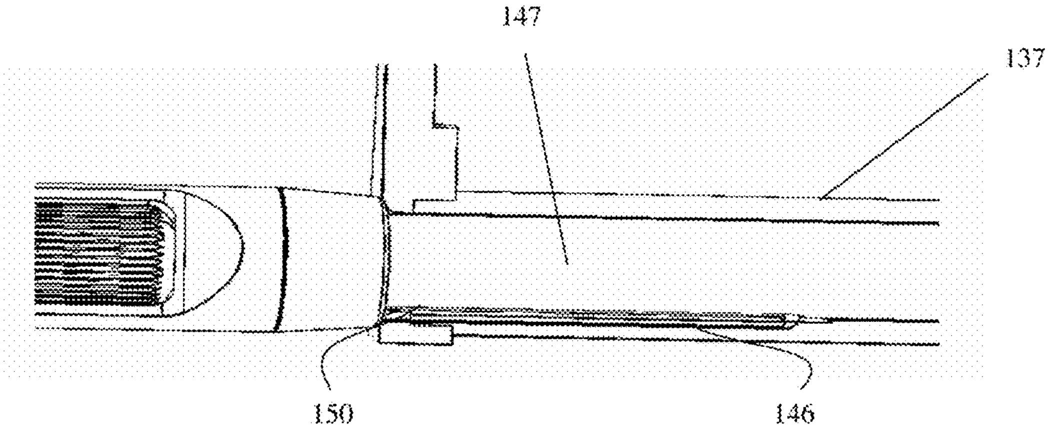
FIG. 43 is a cross sectional, side view of one barrel a surgical tool according to an embodiment of the present invention fully engaged with a fusion implant inserter.
Figure 44:
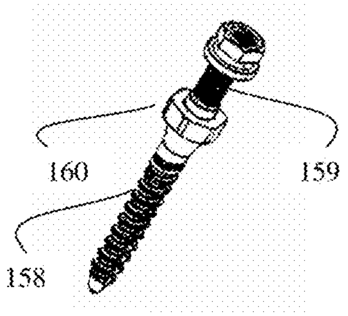
FIG. 44 is a perspective view of a fixation implant assembly.
Figure 45:
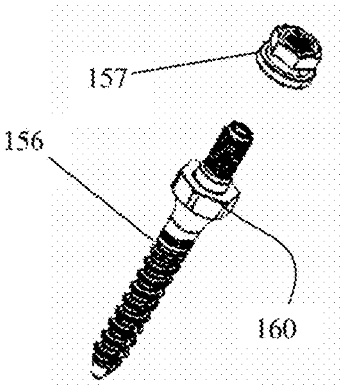
FIG. 45 is an exploded, perspective view of a fixation implant assembly.
Figure 46:
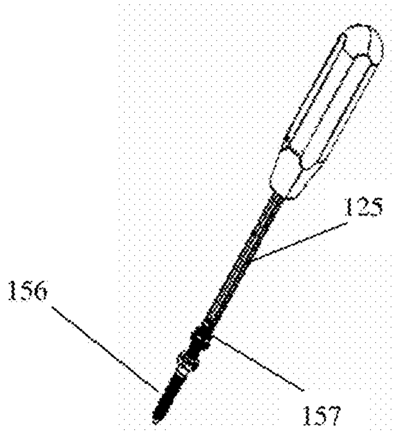
FIG. 46 is a perspective view of a fixation implant insertion assembly.
Figure 47:
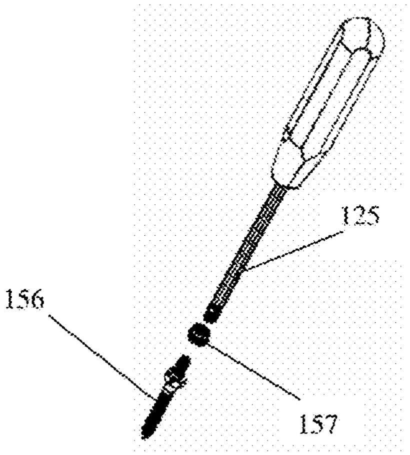
FIG. 47 is an exploded, perspective view of a fixation implant insertion assembly.
Figure 48:
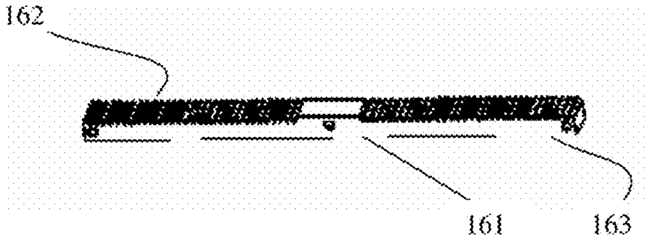
FIG. 48 is a perspective view of an adjustable rack for attaching working channels according to an embodiment of the present invention.

Inserters for fusion devices may be included in the set to facilitate delivery of implants or grafts into the sacroiliac joint and into the ilium and sacrum. Without limiting the invention, FIG. 38 shows an exemplary fusion inserter 147 can be used to deliver a fusion implant of desired materials such as PEEK, metal or biologic material into the surgical site. As seen in FIG. 38, the inserter may have a thumbwheel 148 that is attached to a spring element 150. When thumbwheel 148 is tightened, spring element 150 may be tightened down onto an fusion implant to keep the implant from disengaging from the inserter during implantation. Fork arms 149 may enter recesses on a proximal end of the fusion implant to keep the implant from losing its desired orientation during insertion. Upon desired placement of the fusion implant, thumbwheel 148 may be loosened and the spring element 150 detaches from the implant, leaving the implant in the desired position. Without limiting the invention, FIG. 39 shows an inserter 147 engaged with an exemplary fusion implant 151. In this example, and without limitation, the implant 151 has notices on the lateral sides thereof that may be engaged by the fork arms of inserter 147.

The inserter 147 may have an outer diameter as seen in FIG. 38, that matches the inner diameter of a working channel (e.g., working channels 239, 339, and 350) to keep the inserter directed in an axial plane for desired implant preparation. The inserter may have a timing feature 150 that mates with a female timing feature (e.g., timing feature 146 or 346) on the inside of a working channel (e.g., working channels 239, 339, and 350) to keep the instrument from traveling too far into the surgical site and to further keep the instrument in the proper orientation for desired implant site preparation.

Instrument kit of the present invention may additionally include a driver (e.g., a manual or electrically powered driver, etc.) for inserting joint fixation devices, such as surgical screws, into bone tissue in the articular surfaces of the SI joint and/or into the bone tissue of the ilium and sacrum without the fusion device traversing the SI joint. For example, a bone screw 158 (e.g., a compression screw) may passed through a working channel positioned over an iliac wing and driven through the ilium and sacrum with fixation device driver 125. In other examples, surgical screws 603 and 604 shown in FIGS. 59-61 may be inserted through a working channel over the SI joint and passed into fusion implant 600 at an oblique angle by a special driver having a universal joint or a flexshaft (not shown) that is operable drive the screws into the articular surfaces of the sacrum and ilium at oblique angles in order to secure the fusion implant 600 in the SI joint.

The surgical kits of the present invention may also include one or more of the joint fusion implants disclosed herein, and a particular kit may include an exposure device having an internal cross-section that corresponds to a shape of the one or more joint fusion implants that are included in the kit. The surgical kits may also include one or more joint fixation devices (e.g., surgical screws) for fixing the ilium and sacrum together.

It is to be appreciated that additional surgical tools or implements may be used with the present working channels, and that the invention is not limited to use of the implements described in this section.

Fusion Implants

The present invention also relates to fusion implants that include fixation element(s) that mechanically secure and compress the SI joint, and deliver bone-growth promoting material into the SI joint to facilitate the formation of a contiguous piece of bone from the sacrum to the ilium. The fusion implants of the present invention may be applied to the sacroiliac joint through the novel exposure devices described herein. The novel posterior exposure devices and the combined fixation and stability, compression, and fusion functionalities of the fusion implants of the present invention may allow for posterior approach that may eliminate the need for patient repositioning or further incisions, resulting in less surgery time, less morbidity, and improved recovery time for the patient. Thus, the surgical methods and fusion implants of the present invention allow for a minimally invasive methodology.

To create fixation, stability, and compression from a posterior implant in the sacroiliac joint, the fusion implants of the present invention draw together, connect, and hold the articular surfaces of both the sacrum and ilium together, while stimulating a fusion of the articular surfaces. The joint fusion device may create stress and pressure on the bone tissue by mechanically drawing the bones together, and may thereby utilize bone remodeling (e.g., as according to Wolff's Law) to promote stable and robust bone fusion in the targeted joint. The various embodiments of the fusion implants of the present invention all contain mechanisms that connect both the sacrum and the ilium independently, while using a body thereof to bridge across the two bones for a fusion site. Each of the various embodiments of the fusion implant may include a channel or cavity that may be used to hold bone-growth stimulating materials in the form of autologous bone, allograft, BMP, etc.

In some embodiments of the fusion implant, and without limitation, the fusion implant may have one or more helical anchors for insertion into bone tissue. In such embodiments, the fusion implant may also include a channel or cavity for holding bone growth-enhancing material for promoting fusion of adjacent bones held together by the fusion implant. For example, and without limitation, a fusion implant may include a single helix or multiple helices (e.g., 2 or 3 helices) that may be concentric and/or interwoven. In some embodiments, and without limitation, the helical path of the helical fixation anchors may have a uniform diameter from their proximal end to the distal end thereof. However, in other embodiments, and without limitation, the helical path of the helical fixation anchors may taper outward or inward from the proximal end to the distal end of the helical path to create a conical shape to the helical path.

Figure 49:
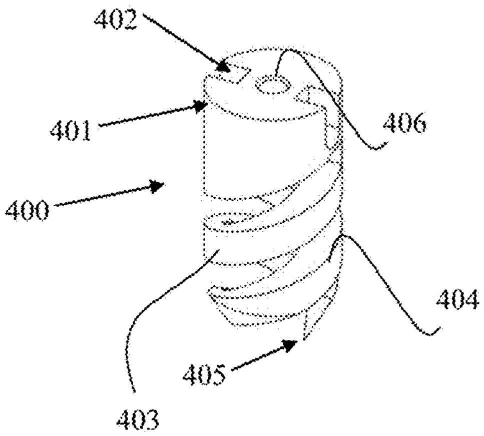
FIG. 49 is a perspective view of a fusion implant having helical fixation elements according to an embodiment of the present invention.
Figure 50:
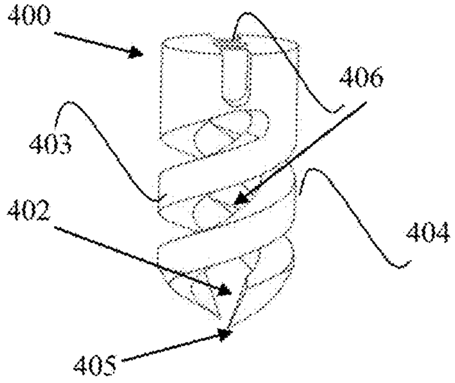
FIG. 50 is a side perspective view of a fusion implant having helical fixation elements according to an embodiment of the present invention.
Figure 51:
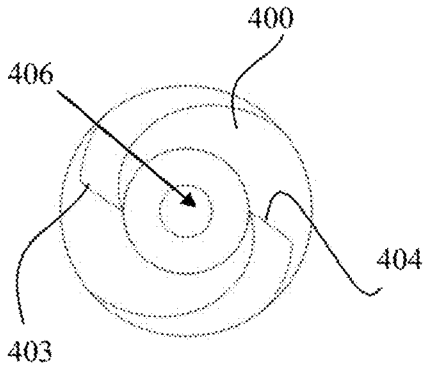
FIG. 51 is a distal view of a fusion implant having helical fixation elements according to an embodiment of the present invention.

Without limiting the invention, FIGS. 49-51 show an exemplary fusion implant 400 having two helical anchors. The implant 400 has a body 401 attached to two helical anchors 403 and 404, which may be concentric and interwoven. Each of the helical anchors 403 and 404 may have a distal cutting edge 405 that may be operable to penetrate bone tissue in joint targeted for fusion. The distal cutting edges of each of the helical anchors 403 and 404 may be on opposite sides of the fusion implant 400 such that as the implant is advanced into the SI joint, the helical anchor 403 engages the ilium and helical anchor 404 engages the sacrum. The body 401 of the fusion implant 400 may have notches or slots 402 in a perimeter thereof that may be engaged by a fusion implant inserter or driver as described herein (e.g., by fork arms 149). The implant 400 may have a outer diameter in a range of about 8 mm to about 20 mm (e.g., about 12 mm to about 18 mm, or any other value or range of values therein). The implant may be paired with a exposure device having a hollow barrel with an internal cross-section that corresponds to the diameter and cross-sectional shape of the implant.

Figure 52:
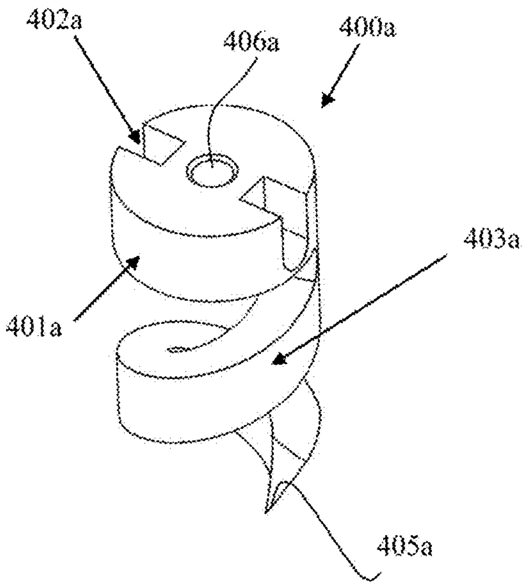
FIG. 52 is a perspective view of a fusion implant having a helical fixation element according to an embodiment of the present invention.
Figure 53:
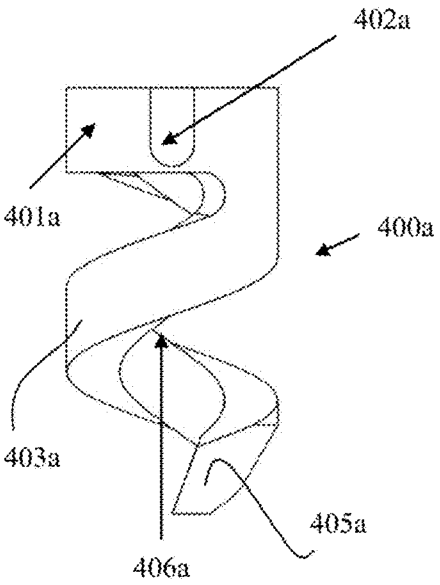
FIG. 53 is a side view of a fusion implant having a helical fixation element according to an embodiment of the present invention.
Figure 54:
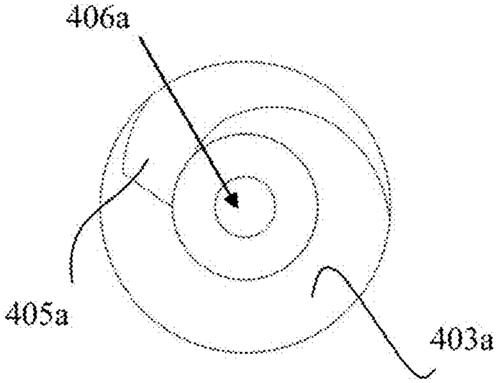
FIG. 54 is a distal view of a fusion implant having a helical fixation element according to an embodiment of the present invention.

In other embodiments, and without limitation, the fusion implant may have a single helix attached to the body of the fusion implant. For example, and without limitation, FIGS. 52-54 illustrate an exemplary fusion implant 400*a* that may include a single helical anchor 403*a*. The fusion implant 400*a* has a body 401*a* attached to the helical anchor 403*a*, which may have a distal cutting edge 405*a* that may be operable to penetrate bone tissue in joint targeted for fusion. After being inserted into the SI joint the body 401*a* may be rotated in a range of about 180° to about 360° (e.g. about 270°, or any value or range of values therein) such that helical anchor 403*a* may engage the articular surfaces of both the ilium and the sacrum so that the fusion implant can compress the bones together and stabilize the SI joint. The body 401*a* of the fusion implant 400*a* may have notches or slots 402*a* in a perimeter thereof that may be engaged by a fusion implant inserter or driver as described herein (e.g., by fork arms 149).

The process of inserting and advancing the fusion implant 400 (or 400*a*, or other related embodiments) may be performed by one or more tools that engage the notches or slots 402 (or 402*a*). An inserter (e.g., inserter 147) may be used to initially place the fusion implant 400 (or 400*a*, or other related embodiment) in a desired position between the sacrum and ilium, and the inserter may be subsequently rotated to engage the helical anchors with the bone tissue of the articular surfaces of the sacrum and ilium. For example, and without limitation, a driving tool may be attached to the inserter to aid in rotating the inserter. As the fusion implant is rotated, the sacrum and ilium bones may be pulled towards each other and the sacroiliac joint may be compressed and stabilized. Cutting edges 405 may be pierce the bone tissue (e.g., cortical and/or cancellous/spongy bone tissue) of the sacrum and ilium. As shown in FIGS. 49-50, but without limitation, the cutting edges 405 of the helical anchors 403 and 404 are aligned with the notches 402 for receiving the inserter tool. This alignment may be included in order to position the cutting edges in a precise position within the joint. For example, the alignment allows the surgeon to control insertion of the cutting edges such that the cutting edge of one of the helical anchors is positioned at the targeted articular surface of the sacrum and the cutting edge of the other helical anchor is positioned at the targeted articular surface of the ilium. In such implementations, the position of the cutting edges can be controlled by the aligning the inserter with the plane of the joint (the plane between the articular surfaces), and thereby placing the cutting edges in close proximity to the targeted articular surfaces such that they engage and penetrate the articular surfaces immediately upon rotation of the inserter. Other embodiments of the fusion implant (e.g., those having a single helical anchor, or flukes, claws, etc.) may also be inserted such that the portion of the fusion implant for engaged with the bone tissue is positioned adjacent to the targeted articular surface when inserted into the joint and prior to rotation of the implant.

In some implementations, and without limitation, surgical tools (e.g., a drill, chisel, rasp, etc.) may be used to remove cortical tissue from the targeted articular surfaces of the sacrum and ilium to prepare ("prep") the articular surfaces for engagement with the fusion implant before the fusion implant is inserted into the joint, allowing the helical anchors of the fusion implant to more easily pierce the bone tissue of the sacrum and ilium. In such implementations, and without limitation, the fusion implant may be inserted into the joint such that the cutting edges of the fusion implant may be aligned with and adjacent to the prepped articular surfaces.

In some implementations, and without limitation, the fusion implant may include a cannulated channel or cavity that allows for the addition of bone growth-stimulating materials into the targeted joint. For example, and without limitation, the fusion implant 400 (or 400*a*, or other related embodiment) may include a cannulated channel (e.g., 406) running from a central hole in the proximal end of body (e.g., 401) through the one or more helical anchors (e.g., 403 and 404) to the distal end(s) of the one or more helical anchors (e.g., 403 and 404). The cannulated channel may be packed with bone growth-stimulating materials (e.g., autologous bone, allograft, BMP, etc.) to stimulate bone growth across the fusion implant and the joint that may lead to fusion of the sacrum and ilium. Without limiting the invention, the bone growth-stimulating materials may be inserted into the channel through a proximal hole in the body after the fusion implant is set into desired operative position. In other implementations, the bone growth-stimulating materials may be present in the channel prior to insertion of the fusion implant into the SI joint.

As an example, and without limitation, FIG. 50 provides a side view of the fusion implant 400 in which the length of the cannulated channel 406 can be seen running from the proximal hole in the body 401 to the distal ends of the helical anchors 403 and 404. FIG. 51 provides a bottom view of the implant 400 and shows the complete cannulated channel 406 and the concentric and interwoven pattern of the helical anchors 403 and 404. However, it should be understood that the present invention is not limited to the particular arrangement of the exemplary helical anchors 403 and 404 in FIGS. 49-51. For example, and without limitation, FIG. 53 provides a side view of fusion implant 400*a* in which the length of cannulated channel 406*a* can be seen running from a proximal hole in the body 401 to the distal end of the helical anchor 403*a*. FIG. 54 provides a bottom view of fusion implant 400*a* showing the complete cannulated channel 406*a*.

Figure 55:
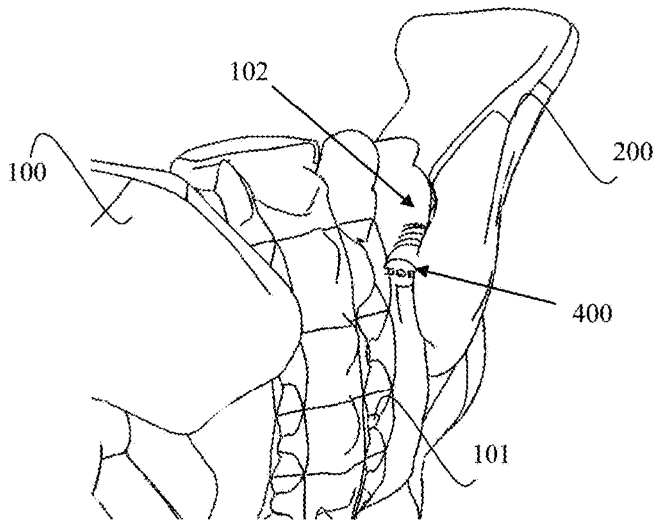
FIG. 55 is an oblique, posterior view of the sacroiliac joint with a fusion implant having helical fixation elements placed in the sacroiliac joint through a posterior approach according to an embodiment of the present invention.

FIG. 55 displays the fusion implant 400 in its desired operative position in the sacroiliac joint 102, where helical anchors 403 is engaged with the ilium 200 and anchor 404 is engaged with the sacrum 101. The implant may create stability and fixation across the joint, compression in the joint, and bone growth-promoting material can be added to the cannulated channel 406 to aid in fusion of the sacrum and ilium at the site of the fusion implant. It is to be understood that other related embodiments (e.g., fusion implant 400*a*) may be placed in the joint in the same manner. It is also to be understood that multiple fusion implants may be placed into the sacroiliac joint from the posterior approach. For example, and without limitation, the double-barreled exposure device 295 shown in FIGS. 118-119, which has two side by side (e.g., parallel) working channels may be used to introduce two fusion implants into the SI joint.

Figure 56:
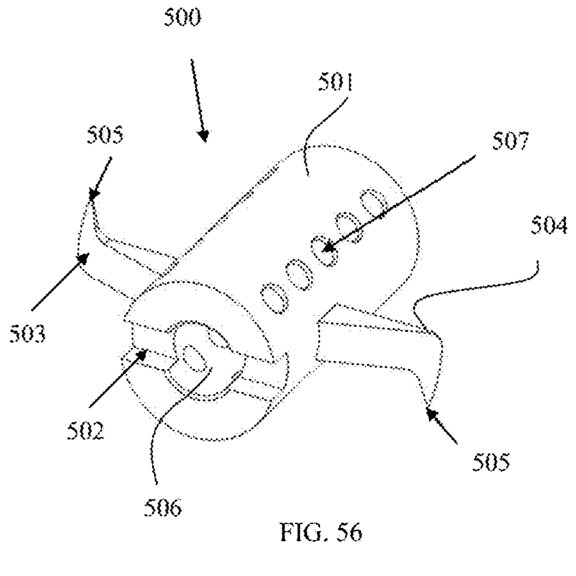
FIG. 56 is a perspective view of a fenestrated sacroiliac fusion implant having lateral flukes according to an embodiment of the present invention.
Figure 57:
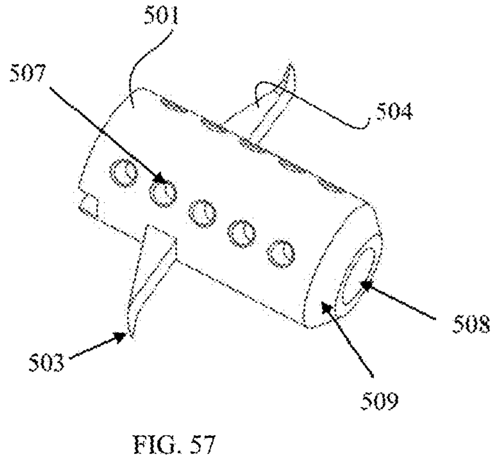
FIG. 57 is a side perspective view of a fenestrated sacroiliac fusion implant having lateral flukes according to an embodiment of the present invention.

In other embodiments of the fusion implant, and without limitation, the fusion implant may have a central body with flukes, claws, hooks, or other bone engaging structures attached thereto. Additionally, the central body may have a channel or cavity in which bone growth-enhancing materials may be included. Without limiting the invention, FIGS. 56-57 show an exemplary embodiment of a fusion implant 500 having lateral flukes 503 and 504 for engaging with the targeted articular surfaces of the SI joint. Each of the lateral flukes 503 and 504 may have a distal hooking ends 505 that may be operable to penetrate bone tissue in joint targeted for fusion. The distal cutting edges of each of the lateral flukes 503 and 504 may be on opposite sides of the fusion implant 500 such that as the fusion implant is advanced into the SI joint, the lateral fluke 503 engages the ilium and lateral fluke 504 engages the sacrum. The proximal end of the body 501 of the fusion implant 500 may have notches or slots 502 in a perimeter thereof that may be engaged by a fusion implant inserter or driver as described herein (e.g., by fork arms 149). The notches or slots 502 may allow the inserter to turn the fusion implant 500 (e.g., in a clockwise direction) to allow for the lateral flukes 503 and 504 to pull the sacrum and ilium towards each other, creating compression. The implant 500 may have a minimum (smallest) outer diameter in a range of about 8 mm to about 20 mm (e.g., about 12 mm to about 18 mm, or any other value or range of values therein), and a maximum (largest) outer diameter in a range of about of about 12 mm to about 40 mm (e.g., about 15 mm to about 30 mm, or any other value or range of values therein). The implant may be paired with an exposure device having a hollow barrel with an internal cross-section that corresponds to the outer diameters and cross-sectional shape of the implant.

The fusion implant 500 may include a cannulated channel or cavity 506 that allows for the addition of bone growth-stimulating materials into the targeted joint. For example, and without limitation, the fusion implant 500 includes cannulated channel 506 running from a central hole in the proximal end of body 501 a distal hole 508 in the body 501. The cannulated channel 506 may be packed with bone growth-stimulating materials (e.g., autologous bone, allograft, BMP, etc.) to stimulate bone growth across the fusion implant and the joint that may lead to fusion of the sacrum and ilium. The body 501 may have a number of fenestrations 507 therein to allow for lateral bone growth through the implant, which may result in a stable fusion site between the sacrum and ilium. Without limiting the invention, the bone growth-stimulating materials may be inserted into the channel 506 through the proximal hole in the body 501 after the fusion implant 500 is set into desired operative position. In other implementations, the bone growth-stimulating materials may be present in the channel 506 prior to insertion of the fusion implant 500 into the SI joint.

The process of inserting and advancing the fusion implant 500 may be performed by one or more tools that engage the notches or slots 502. An inserter (e.g., inserter 147) may be used to initially place the fusion implant 500 in a desired position between the sacrum and ilium. Without limiting the invention, FIG. 54 shows the fusion implant 500 having a self-distracting bullet nose 509. The bullet nose may have a round geometry and/or a tapered rounded profile that is operable to distract the SI joint with minimal damage to soft and connective tissue in and around the posterior side of the SI joint. The bullet nose 509 may facilitate entry into the sacroiliac joint prior to the lateral flukes 503 and 504 being rotated into place in the sacrum and ilium. The sloped bullet nose 509 and the inserter may be subsequently rotated to engage the lateral flukes 503 and 504 with the bone tissue of the articular surfaces of the sacrum and ilium. As the fusion implant 500 is rotated, the sacrum and ilium bones may be pulled towards each other and the sacroiliac joint may be compressed and stabilized. Hooking ends 505 may pierce the bone tissue (e.g., cortical and/or cancellous/spongy bone tissue) of the sacrum and ilium. As shown in FIGS. 56-57, but without limitation, the lateral flukes 503 and 504 may be aligned with the notches 502 for receiving the inserter tool. This alignment may be included in order to position the cutting edges in a precise position within the joint (e.g., with the lateral flukes aligned with the plane of the joint between the articular surfaces such that the hooking ends are positioned at the targeted articular surfaces).

As discussed above, and without limiting the invention, the working channel through which the implant is passed into the SI joint may have an oblong cross-sectional shape or slots running along its length for accommodating the lateral flukes of the implant. For example, and without limitation, the channel may have a hollow barrel with slots may be separated by about 180° along the length of the working channel and may have a shape that can accommodate the shape of the lateral flukes (e.g., a generally rectangular shape that is sufficiently large to accommodate the shape of the lateral flukes).

Figure 58:
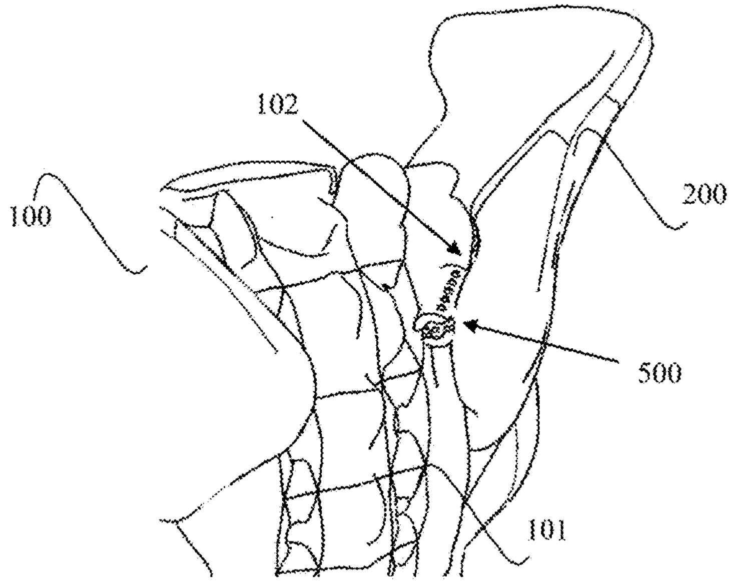
FIG. 58 is an oblique, posterior view of the sacroiliac joint with a fenestrated fusion implant having lateral flukes placed in the sacroiliac joint through a posterior approach according to an embodiment of the present invention.

FIG. 58 displays the implant 500 in a desired operative position in the sacroiliac joint 102, where lateral fluke 503 is engaged with the ilium 200 and lateral fluke 504 is engaged with the sacrum 101. The implant may create stability and fixation across the joint, compression in the joint, and bone growth-promoting material can be added to the cannulated channel 506 to aid in fusion of the sacrum and ilium at the site of the fusion implant.

Figure 59:
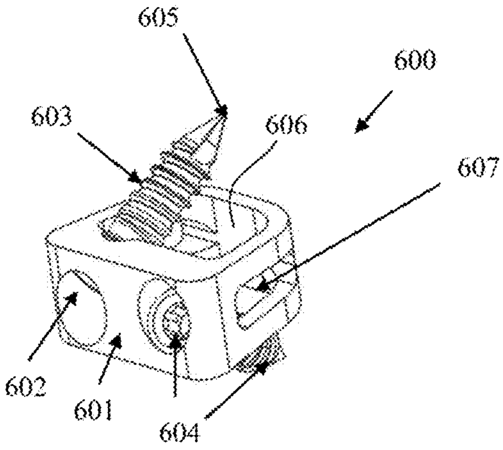
FIG. 59 is a perspective view of an open-body, compression screw sacroiliac fusion implant according to an embodiment of the present invention.
Figure 60:
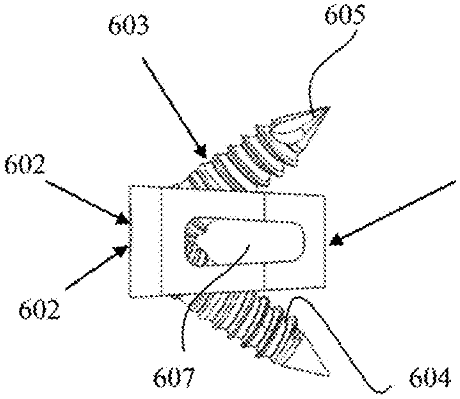
FIG. 60 is a superior view of an open-body, compression screw sacroiliac fusion implant according to an embodiment of the present invention.
Figure 61:
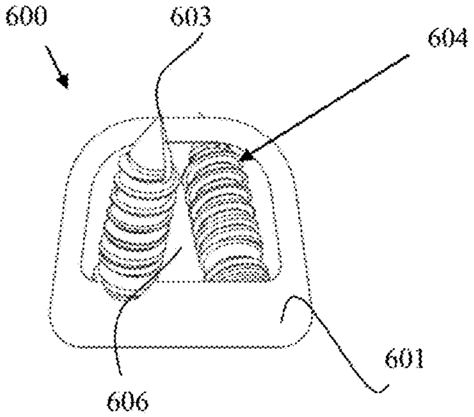
FIG. 61 is a side view of an open-body, compression screw sacroiliac fusion implant according to an embodiment of the present invention.

In other embodiments of the fusion implant, and without limitation, the fusion implant may have a box-like open body having holes therein for receiving one or more surgical screws for attaching the fusion implant to the sacrum and/or ilium. Without limiting the invention, FIGS. 59-61 show an exemplary embodiment of a fusion implant 600 having a box-like body 601 having holes 602*a* and 602*b* in a proximal end thereof for receiving surgical screws 603 and 604 for engaging with the targeted articular surfaces of the SI joint and holding the fusion implant 600 in place within the SI joint. The body 601 may be designed such that a central plane of the body 601 bisecting the proximal end of the body 601 and bisecting screw holes 602*a* and 602*b* may be roughly aligned with the plane of the SI joint between the articular surfaces when the fusion implant is inserted into the SI joint. The box-like geometry of the fusion implant 600 may resist torsional stress applied by movement of the SI joint. The implant 600 may have a minimum (smallest) outer diameter in a range of about 8 mm to about 20 mm (e.g., about 12 mm to about 18 mm, or any other value or range of values therein), and a maximum (largest) outer diameter in a range of about of about 12 mm to about 40 mm (e.g., about 15 mm to about 30 mm, or any other value or range of values therein). The implant may be paired with an exposure device having a hollow barrel with an internal cross-section that corresponds to the outer diameters and cross-sectional shape of the implant.

The screw holes 602*a* and 602*b* may be angled obliquely with respect to the central plane of the body 601. For example, and without limitation, hole 602*a* may run obliquely toward a first lateral side of the central plane, and hole 602*b* may run obliquely toward a second (and opposite) lateral side of the central plane. This arrangement allows the surgical screw 603 inserted through screw hole 602*a* to engage one of the bones in the SI joint (e.g., the sacrum) and the surgical screw 604 inserted through screw hole 602*b* to engage with the other bone in the SI joint (e.g., the ilium).

Without limiting the invention, the surgical screws 603 and 604 may be self-drilling screws that can penetrate the bone tissue (e.g., cortical and/or cancellous/spongy bone tissue) of the articular surface. The articular surfaces of the sacrum and/or the ilium may be prepared for the insertion of the surgical screws by removing cortical tissue at the insertion point for the screws or pre-drilling holes for the screws; in such embodiments, self-drilling screws may or may not be utilized. In some implementations, the surgical screws may be doubled threaded screws that create compression of the joints, which may draw the sacrum and ilium together as they are advanced into the bone tissue. The screws may be driven into the bone tissue of the ilium and sacrum by a driving device passed through the working channel positioned over the SI joint, where the driving device has a universal joint or flex shaft (not shown) that allows it to drive the screws into the ilium and sacrum at oblique angles.

The open body 601 of the implant 600 may have a cavity in which bone growth-enhancing materials may be included. The fusion implant 600 may have an open design, where there are no sidewalls closing off the cavity 606 to the articular surfaces of the sacrum and ilium so that bone growth stimulating material that may be placed within the cavity 606 may be in contact with the articular surfaces of the sacrum and ilium within the joint to allow fusion growth across the SI joint. FIG. 61 shows a side view of the fusion implant 600, in which it can be seen that the fusion implant 600 may have a cavity 606 that is completely open on the lateral sides with no sidewalls to obstruct contact between bone growth-stimulating materials in the cavity 606 and the articular surfaces of the sacrum and ilium. As shown in FIG. 60, the fusion implant 600 may further include openings 607 along the outer wall of the fusion implant to allow further access to the bone growth-stimulating material in the cavity 606.

The process of inserting and advancing the fusion implant 600 may be performed by one or more tools that advance the implant through a working channel, as described herein. An inserter (e.g., inserter 147) may be used to initially place the fusion implant in a desired position between the sacrum and ilium. In some embodiments, and without limitation, the fusion implant may include slots or notches on the proximal end thereof (not shown), which the inserter can engage. In other embodiments, and without limitation, the inserter may engage the lateral edges of the proximal end of the fusion implant. Once the fusion implant 600 is placed in the targeted position in the SI joint, the surgical screws 603 and 604 may be advanced through screw holes 602*a* and 602*b*, respectively. As the surgical screws 603 and 604 are advanced into the bone tissue of the sacrum and ilium, the sacrum and ilium bones may be pulled towards each other and the sacroiliac joint may be compressed and stabilized. The surgical screws 603 and 604 may pierce the bone tissue (e.g., cortical and/or cancellous/spongy bone tissue) of the sacrum and ilium.

As discussed above, and without limiting the invention, the working channel through which the implant is passed into the SI joint may have an oblong cross-sectional shape or slots running along its length for accommodating the width of the fusion implant 600. For example, and without limitation, the working channel may have a hollow barrel having slots may be separated by about 180° along the length of the working channel and may have a shape that may accommodate the shape of the body of the fusion implant.

Figure 62:
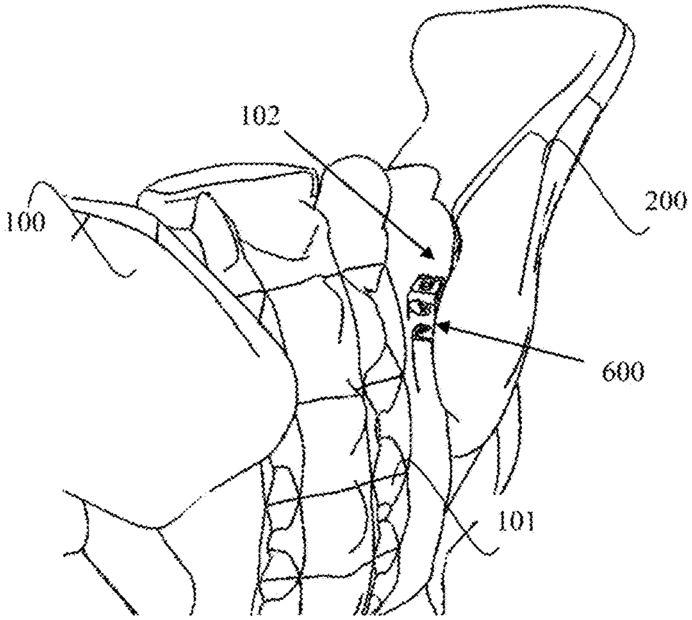
FIG. 62 is an oblique, posterior view of the sacroiliac joint with an open-body, compression screw sacroiliac fusion implant placed in the sacroiliac joint through a posterior approach according to an embodiment of the present invention.

FIG. 62 displays the implant 600 in a desired operative position in the sacroiliac joint 102, where surgical screw 603 may be engaged with the ilium 200 and surgical screw 604 may be engaged with the sacrum 101. The implant may create stability and fixation across the joint, compression in the joint, and bone growth-promoting material can be added to the cavity 606 to aid in fusion of the sacrum and ilium at the site of the fusion implant.

Figure 63:
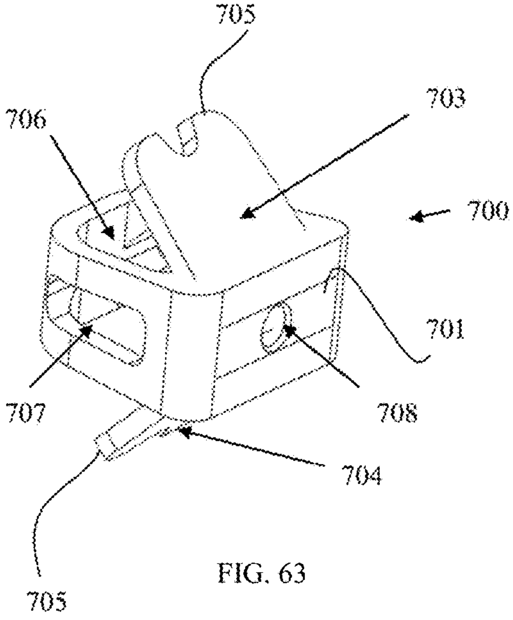
FIG. 63 is a perspective view of an open-body sacroiliac fusion implant having lateral blades according to an embodiment of the present invention.
Figure 64:
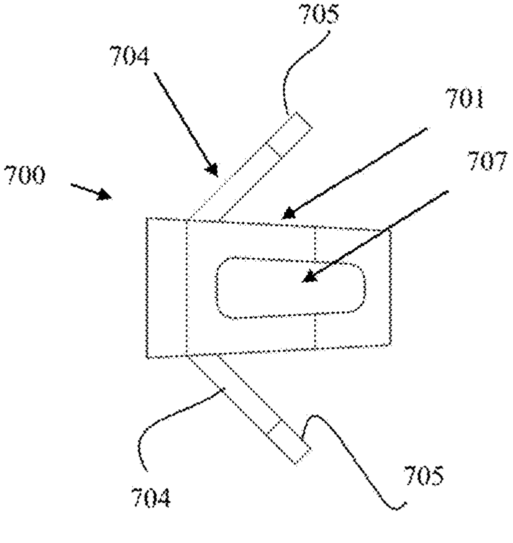
FIG. 64 is a superior view of an open-body sacroiliac fusion implant having lateral blades according to an embodiment of the present invention.

In other embodiments of the fusion implant, and without limitation, the fusion implant may have a box-like central body having laterally extending blades for engaging the sacrum and/or ilium. Without limiting the invention, FIGS. 63-64 show an exemplary embodiments of a fusion implant 700 having a box-like body 701 having laterally extending blades 703 and 704 for engaging with the targeted articular surfaces of the SI joint and holding the fusion implant 700 in place within the SI joint. The body 701 may be designed such that a central plane of the body 701 bisecting the proximal end of the body 701 may be roughly parallel or aligned with the plane of the SI joint between the articular surfaces when the fusion implant 700 is inserted into the SI joint. The box-like geometry of the fusion implant 700 may resist torsional stress applied by movement of the SI joint. The implant 700 may have a minimum (smallest) outer diameter in a range of about 8 mm to about 20 mm (e.g., about 12 mm to about 18 mm, or any other value or range of values therein), and a maximum (largest) outer diameter in a range of about of about 12 mm to about 40 mm (e.g., about 15 mm to about 30 mm, or any other value or range of values therein). The implant may be paired with an exposure device having a hollow barrel with an internal cross-section that corresponds to the outer diameters and cross-sectional shape of the implant.

The lateral blades 703 and 704 may be angled obliquely with respect to the central plane of the body 701. For example, and without limitation, blade 703 may run obliquely toward a first lateral side of the central plane, and blade 704 may run obliquely toward a second (and opposite) lateral side of the central plane. This arrangement allows the blade 703 to engage one of the bones in the SI joint (e.g., the sacrum) and the blade 704 to engage with the other bone in the SI joint (e.g., the ilium). The lateral blades may be separately formed or integral to the fusion implant 700. The lateral blades may have an outer edge 705 for engagement with the bone tissue of the sacrum or ilium. The outer edge may have varying geometry to facilitate entry into and compression of the sacrum and ilium. In some implementations, and without limitation, the outer edges of the lateral blades may have a sharp cutting edge which can penetrate the bone tissue. In some implementations, and without limitation, the outer edges may be serrated (e.g., with one or more kinds of teeth, such as triangular teeth, hook teeth, crown teeth, etc.). The outer edge may facilitate penetration of the lateral blades into the bone tissue (e.g., cortical and/or cancellous/spongy bone tissue) of the articular surfaces of the ilium and sacrum when the fusion implant is advanced into the SI joint. In some implementations, and without limitation, the articular surfaces of the sacrum and/or the ilium may be prepared for the insertion of the lateral blades by removing cortical tissue at the insertion point.

The body 701 of the implant 700 may have a cavity 706 in which bone growth-enhancing materials may be included. The fusion implant 700 may have an open design, where there are no sidewalls closing off the cavity 706 to the articular surfaces of the sacrum and ilium so that bone growth stimulating material that may be placed within the cavity 706 may be in contact with the articular surfaces of the sacrum and ilium within the joint to allow fusion growth across the SI joint. As shown in FIG. 64, the fusion implant 700 may further include openings 707 along the outer wall of the fusion implant to allow further access to the bone growth-stimulating material in the cavity 706. The fusion implant 700 may include a central hole 708 in the proximal end of the body 701. The central hole 708 may allow for access into the cavity 706, allowing the bone growth-stimulating materials to be inserted into the cavity 706 either before or after the fusion implant 700 is set into desired operative position in the SI joint. In some implementations, the bone growth-stimulating materials may be present in the cavity 706 prior to insertion of the fusion implant 700 into the SI joint. The design of fusion implant 700 (and other related embodiments) allows for bone graft to be placed pre-operatively as the cavity 706 is not obscured by the lateral blades (bone anchoring mechanism).

The process of inserting and advancing the fusion implant 700 may be performed by one or more tools that advance the implant through a working channel, as described herein. An inserter (e.g., inserter 147) may be used to initially place the fusion implant in a desired position between the sacrum and ilium. In some embodiments, and without limitation, the fusion implant may include slots or notches on the proximal end thereof (not shown), which the inserter can engage. In other embodiments, and without limitation, the inserter may engage the lateral edges of the proximal end of the fusion implant. The fusion implant 700 may be drive into place in the targeted position in the SI joint by the inserter. As the fusion implant 700 is advanced into the SI joint, the lateral blades 703 and 704 are driven into and penetrate the bone tissue of the sacrum and ilium, and the blades 703 and 704 may act to draw in the sacrum and ilium bones and the sacroiliac joint may be compressed and stabilized. The lateral blades 703 and 704 may pierce the bone tissue (e.g., cortical and/or cancellous/spongy bone tissue) of the sacrum and ilium as the fusion implant is driven into the SI joint. In other implementations, and without limitation, the inserter may be used to place the fusion implant 700 at the SI joint, and subsequently an impactor or other driving tool may be used to drive the fusion implant 700 into the bone tissue and into position in the SI joint.

As discussed above, and without limiting the invention, the working channel through which the implant is passed into the SI joint may have a hollow barrel having an oblong interior cross-sectional shape or slots running along its length for accommodating the width of the fusion implant 700 and the lateral blades 703 and 704. For example, and without limitation, a first set of slots may be separated by about 180° along the length of the working channel and may have a shape that is complementary to or large enough accommodate the shape of the fusion implant, and a second set of slots may be separated by about 180° along the length of the working channel and may have a shape may accommodate the shape of the lateral blades.

Figure 65:
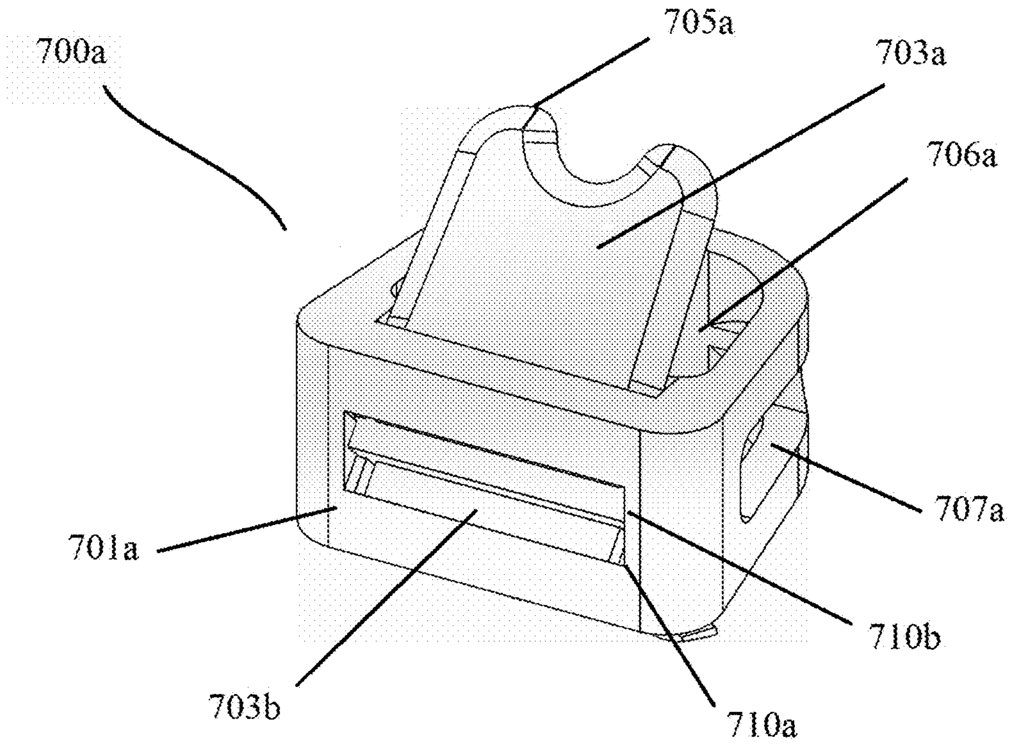
FIG. 65 is a perspective view of an open-body sacroiliac fusion implant having detachable lateral blades according to an embodiment of the present invention.
Figure 66:
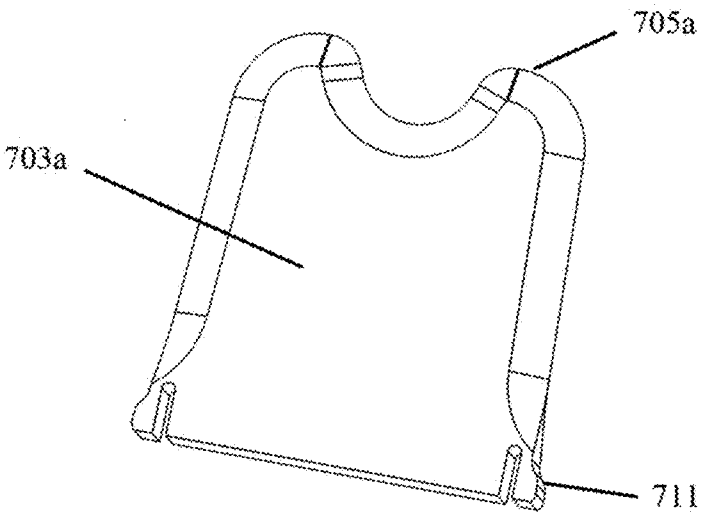
FIG. 66 is a perspective view of a detached lateral blade for an open-body sacroiliac fusion implant according to an embodiment of the present invention.

FIGS. 65-66 show a fusion implant 700*a* that is similar to implant 700 in shape, size, and function, but the blades 703*a* and 703*b* of implant 700*a* are detachable from the implant. As shown in FIG. 65, the lateral blades 703*a* and 703*b* are inserted into slots 710*a* and 710*b* in the distal portion of the body 701*a*, respectively. This fusion implant embodiment allows for the body 701*a* to be inserted into the SI joint prior to the insertion of the blades 703*a* and 703*b* into the body 701*a*. This may allow the implant 700*a* to be inserted into the SI joint and the blades to be subsequently inserted into the slots 710*a* and 710*b* and engaged with the bone tissue of the ilium and sacrum without the need for a specially shaped (e.g., oblong or slotted) working channel. The blades 703*a* and 703*b* may be passed through the working channel and into slots 710*a* and 710*b* after the body 701*a* has been positioned in the SI joint. An inserter and/or impactor or other tools may be used to insert the blades 703*a* and 703*b* into the slots 710*a* and 710*b* and into the bone tissue of the ilium and sacrum.

As shown in FIG. 66, the blades of implant 700*a* may include pressure clips 711 that engage with slots 710*a* and 710*b* when the blades are inserted into the slots. The pressure clips may lock the blades into the slots to help stabilize the fusion implant.

Figure 67:
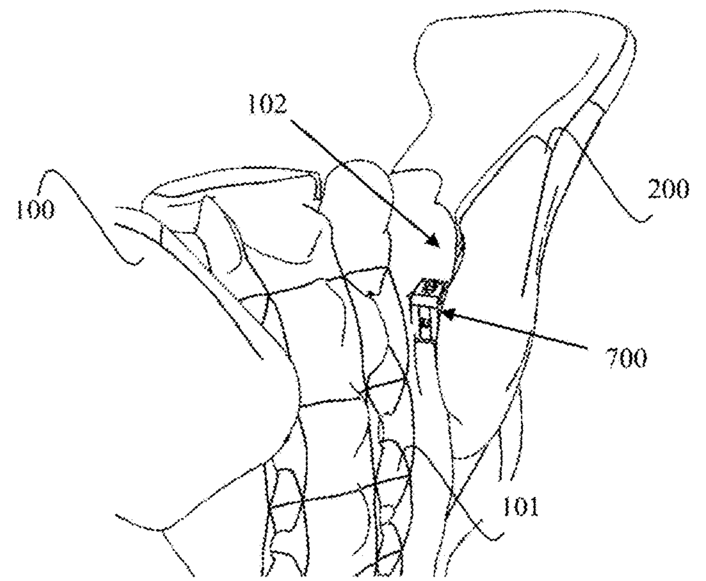
FIG. 67 is an oblique, posterior view of the sacroiliac joint with an open-body sacroiliac fusion implant having lateral blades placed in the sacroiliac joint through a posterior approach according to an embodiment of the present invention.

FIG. 67 displays the implant 700 (or implant 700*a*) in a desired operative position in the sacroiliac joint 102, where lateral blade 703 is engaged with the ilium 200 and lateral blade 704 is engaged with the sacrum 101. The implant may create stability and fixation across the joint, compression in the joint, and bone growth-promoting material can be added to the cavity 706 to aid in fusion of the sacrum and ilium at the site of the fusion implant.

Figure 68:
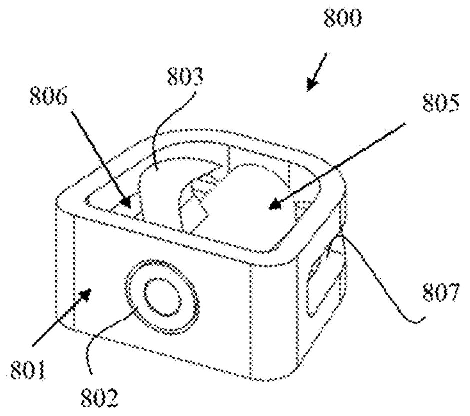
FIG. 68 is a perspective view of an open-body sacroiliac fusion implant having a rotatable member with lateral flukes according to an embodiment of the present invention.
Figure 69:
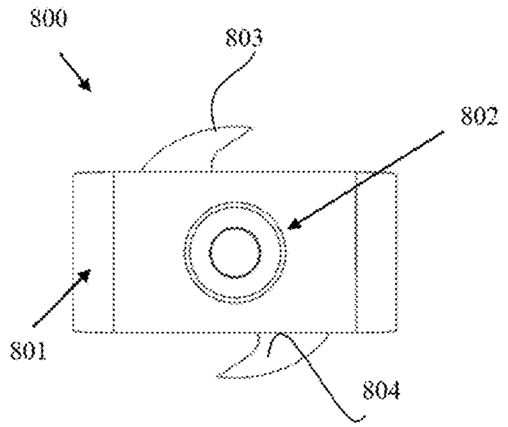
FIG. 69 is a proximal view of an open-body sacroiliac fusion implant having a rotatable member with lateral flukes according to an embodiment of the present invention.

In other embodiments of the fusion implant, and without limitation, the fusion implant may have a box-like central body having a rotatable central axle with lateral flukes thereon for engaging the sacrum and/or ilium as the central axle is rotated. Without limiting the invention, FIGS. 68-69 show an exemplary embodiment of a fusion implant 800 having a box-like open body 801 having a central axel 805 to which two flukes 803 and 804 are attached for engaging with the targeted articular surfaces of the SI joint and holding the fusion implant 800 in place within the SI joint. The flukes 803 and 804 may engage with the articular surfaces of the sacrum and ilium, respectively, when the central axis is rotated. The body 801 may be designed such that a central plane of the body 801 bisecting the proximal end of the body 801 may be roughly parallel to or aligned with the plane of the SI joint between the articular surfaces when the fusion implant 800 is inserted into the SI joint. The box-like geometry of the fusion implant 800 may resist torsional stress applied by movement of the SI joint. The implant 800 may have a minimum (smallest) outer diameter in a range of about 8 mm to about 20 mm (e.g., about 12 mm to about 18 mm, or any other value or range of values therein), and a maximum (largest) outer diameter in a range of about of about 12 mm to about 40 mm (e.g., about 15 mm to about 30 mm, or any other value or range of values therein). The implant may be paired with an exposure device having a hollow barrel with an internal cross-section that corresponds to the outer diameters and cross-sectional shape of the implant.

Without limiting the invention, the flukes 803 and 804 may extend out laterally from central rotating axis 805 at about 180° from each other. This arrangement allows the fluke 803 to engage one of the bones in the SI joint (e.g., the sacrum) and the fluke 804 to engage with the other bone in the SI joint (e.g., the ilium) as the central axle 805 is rotated. In other implementations, and without limitation, the flukes may have other relative positions on the central axle. In still other implementations, and without limitation, the fusion implant may have more than two flukes attached to the central axis that may be arranged in various positions on the central rotating axle. Without limiting the invention, the curvature of all of the flukes extending from the central axle may be oriented in either a clockwise or counterclockwise fashion when viewing the fusion implant from the proximal end of the body (e.g., like the perspective of FIG. 69). The consistent orientation of all of the flukes allows all of the hooks to engage (hook into) the tissue in the SI joint as the central axle is rotated. In other implementations, and without limitation, one or more of the flukes on the central axle may be obliquely oriented, which may provide additional bite and purchase into the bone tissue. The hooking edge of the hooks may have varying geometry to facilitate entry into and compression of the sacrum and ilium. In some implementations, and without limitation, the hooking edges of the flukes may have a sharp cutting edge which can penetrate the bone tissue. In some implementations, and without limitation, the hooking edges may be serrated (e.g., with one or more kinds of teeth, such as triangular teeth, hook teeth, crown teeth, etc.). The hooking edges may facilitate penetration of the flukes into the bone tissue (e.g., cortical and/or cancellous/spongy bone tissue) of the articular surfaces of the ilium and sacrum when the central axle is rotated. In some implementations, and without limitation, the articular surfaces of the sacrum and/or the ilium may be prepared for the insertion of the surgical screws by removing cortical tissue at the insertion point.

The body 801 of the implant 800 may have a cavity 806 through which the central axle 805 passes. The central axle may rotatably attach to both the proximal and distal ends of the body 801, such that the central axle 805 may be rotated once the fusion implant is inserted into the SI joint. The central axle 805 may be rotatable in either the clockwise and/or the counterclockwise direction (e.g., from the perspective of FIG. 69). In some implementations, and without limitation, the central axle 805 may be rotatable in only one direction, that being the direction that allows the hooks to bite into the bone tissue in the SI joint. The one-directional implementation may prevent the hooks from rotating and slipping out of the bone tissue, once they have been rotated and inserted into the bone tissue in the SI joint.

The cavity 806 may have an open design into which bone growth-enhancing materials may be inserted. The body 801 may have no sidewalls closing off the cavity 806 to the articular surfaces of the sacrum and ilium so that bone growth stimulating material that may be placed within the cavity 806 may be in contact with the articular surfaces of the sacrum and ilium within the joint to allow fusion growth across the SI joint. As shown in FIG. 68, the fusion implant 800 may further include openings 807 along the outer wall of the fusion implant 800 to allow further access to the bone growth-stimulating material in the cavity 806.

The process of inserting and advancing the fusion implant 800 may be performed by one or more tools that advance the implant through a working channel, as described herein. An inserter (e.g., inserter 147) may be used to initially place the fusion implant in a desired position between the sacrum and ilium. In some embodiments, and without limitation, the fusion implant may include slots or notches on the proximal end thereof (not shown), which the inserter can engage. In other embodiments, and without limitation, the inserter may engage the lateral edges of the proximal end of the fusion implant. Subsequently, a driving tool may be engaged with a central hole 802 in the proximal end of the body 801, which may be "keyed" with teeth or other structures that can be engaged by the driving tool. The driving tool may be operable to rotate the central axle 805 once it is engaged with the central hole 802, thereby driving the flukes 803 and 804 into the bone tissue in the articular surfaces of the sacrum and ilium.

In some embodiments, and without limitation, the inserter may have a head that has a complementary shape to the central hole 802, allowing the inserter to engage the with the central hole 802 prior to insertion. The ring structure around the central hole 802 may be connected with or integral to the central axle 805, allowing central axle to be rotated by the inserter. For example, and without limitation, the inserter can be used to insert the fusion implant into the SI joint, and then the head of the inserter may be rotated in order to rotate the central axle of the fusion implant, thereby engaging the hooks with the bone tissue in the articular surfaces of the sacrum and ilium.

As discussed above, and without limiting the invention, the working channel through which the implant is passed into the SI joint may have a hollow barrel having an oblong internal cross-section or slots running along its length for accommodating the width of the fusion implant 800 and the lateral flukes 803 and 804.

The central hole 802 may also allow for access into the cavity 806, such that bone growth-stimulating materials may be inserted into the cavity 806 after the fusion implant 800 is set into desired operative position in the SI joint. In some implementations, and without limitation, the bone growth-stimulating materials may be present in the cavity 806 prior to insertion of the fusion implant 800 into the SI joint. The design of fusion implant 800 (and other related embodiments) allows for bone graft to be placed pre-operatively as the cavity 806 is not obscured by the central axle and hooks (bone anchoring mechanism).

In some embodiments, and without limitation, the fusion implant may have a shape and features like the implant 151 shown in FIGS. 39 and 126-129. As an example, and without limiting the invention, the implant may be a bone graft as shown in FIGS. 126-129. The implant 151 may be substantially rectangular, having ribbing 153 on opposing sides to create a surface for catching or gripping with the SI joint when it is inserted. The implant 151 may also have a tapered proximal end to be inserted into the SI joint to act as a wedge, facilitating insertion. The implant 151 may also have slots 152 for receiving forceps of an inserter, and transverse holes to allow bone tissue to grow through the implant and incorporate the implant into the native bone tissue, thereby fusing the SI joint.

FIGS. 71-91 displays the implant in a desired operative position in the sacroiliac joint 102, where the implant is engaged with the ilium 200 and the sacrum 101. The implant may create stability and fixation across the joint, compression in the joint, and bone growth-promoting material can be added to the cavity 806 to aid in fusion of the sacrum and ilium at the site of the fusion implant.

Surgical Methods

In some embodiments, the methods of the present invention substantially fuse the SI joint, such that movement in the joint is minimized or substantially eliminated, thereby diminishing or substantially eliminating the patient's pain and discomfort. More specifically, an improved, combined approach for both mechanical holding and surgical fusion through a novel exposure device is described herein. Specifically, with respect to some embodiments, an approach is described to address the SI joint through a posterior approach. In some embodiments, and without limitation, the surgical fusion of the sacrum and an ilium may be accomplished with a posteriorly inserted fusion implant device alone. In other embodiments, and without limitation, surgical fusion may be accomplished with the delivery of both (1) a fusion implant device into the SI joint, and (2) a separate fixation device which can be in the form of a screw, or the like. The fusion may be delivered to the SI joint, placed between the sacrum and ilium, while the fixation device may be delivered through the iliac wing, near the iliac crest, into the sacrum while not entering or passing through the SI joint.

In some embodiments, and without limitation, the method may involve the posterior insertion of a fusion implant, including the steps of creating an incision proximal to the patient's SI joint, dilating the incision, engaging a novel exposure device as described herein with the incision, creating a void in the SI joint, and inserting the fusion implant into the void such that it engages with the articular surfaces of the sacrum and ilium.

Some embodiments, without limitation, include some or all of the following steps, preparing the patient for surgery (e.g., positioning the patient in a prone position to provide the surgeon access to the SI joint, general or local anesthesia, and the like), locating the SI joint and an incision point for access to the SI joint (e.g., by blunt finger palpation), insertion of a pin or wire to create an incision, insertion of a dilator over the pin and impacting the dilator to dilate the incision to a width through which instruments may be passed, inserting a working channel of a novel exposure device over the dilator, securing the working channel in position with fixing pins, removing the dilator, inserting a drill bit apparatus through the working channel, using the drill bit apparatus in the working channel to displace bone in the SI joint thereby creating a void, removing the drill bit apparatus, loading a fusion implant onto an inserter and inserting the fusion implant and inserter into the working channel until the implant is positioned proximal to the void in the patient's SI joint, inserting an impactor into the first working channel and applying force to displace the implant into the void in the patient's SI joint, removing all instruments, and closing the incision.

In some embodiments, and without limitation, the method may involve the posterior insertion a fusion implant and the insertion a separate fixation device through the ilium and sacrum, including the steps of creating an incision proximal to the patient's SI joint, creating an incision over iliac wing, dilating the incisions, engaging a novel exposure device as described herein with both incisions, creating a void in the SI joint, inserting a fusion implant into the void, drilling a hole through the ilium and the S1 vertebra of the sacrum, and inserting a joint fusing device in the ilium and sacrum. The fixation device may be inserted through the iliac wing, near the iliac crest, into the sacrum while not entering or passing through the SI joint.

Other embodiments, without limitation, include some or all of the following steps, preparing the patient for surgery (e.g., positioning the patient in a prone position to provide the surgeon access to the SI joint, general or local anesthesia, and the like), making a small incision over the top of the iliac wing from a posterior approach, locating the SI joint and an incision point for access to the SI joint (e.g., by blunt finger palpation), insertion of a pin or wire to create an incision, insertion of a dilator over the pin and impacting the dilator to dilate the incision to a width through which instruments may be passed, inserting a first working channel of a double-barreled, double-angled exposure device over the dilator and inserting a second working channel of said exposure device in the incision over the iliac wing, securing the first and second working channels in position with fixing pins, removing the dilator, inserting a drill bit apparatus through each of the first and second work channels, using the drill bit apparatus in the first working channel to displace bone in the SI joint thereby creating a void, using the drill bit apparatus (or a second drill bit apparatus) in the second working channel to drill a hole in the iliac crest and the S1 vertebra of the sacrum, removing the drill bit apparatus, loading an implant (e.g., a graft) onto an inserter and inserting the implant and inserter into the first working channel until the implant is positioned proximal to the void in the patient's SI joint, inserting an impactor into the first working channel and applying force to displace the implant into the void in the patient's SI joint, inserting a joint fusion device coupled to a fusion device inserter into the second working channel and implanting said joint fusion device in the hole in the iliac crest and the sacrum, removing all instruments, and closing the incisions.

Some embodiments include the use of embodiments of the tools or tool sets of the present invention, as described above. Other embodiments of the methods of the present invention are performed without using the tools of the present invention. The methods of the present invention may be performed in addition to or in conjunction with one or more of the known methods. Embodiments of the methods of the present invention (and tools of the present invention) are now further described with reference to the Figures. Although the methods are described with respect to the use of certain tools, other tools with different structures may be used and still be within the scope of the present invention.

Figure 72:
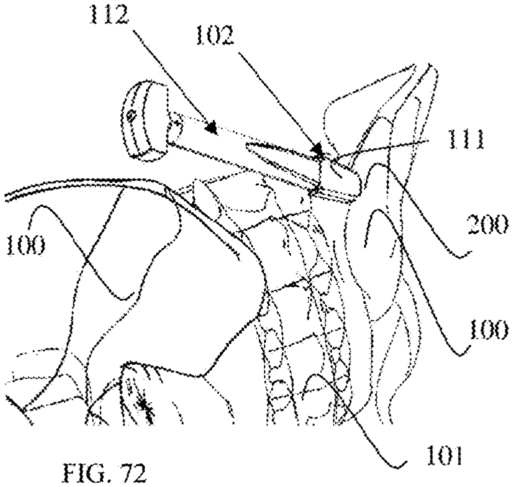
FIG. 72 is an oblique posterior view of the sacroiliac joint and a joint probe.

FIGS. 72-99 illustrate a surgical procedure for fusing an SI joint with both a fusion implant inserted in the SI joint and a joint fixation device (e.g., a bone screw). The procedure includes positioning a patient in the prone position and administering either a local or general anesthetic. Blunt finger palpation may be used to locate the patient's iliac wing and the SI joint. As shown in FIG. 72, the SI joint 102 is located between the iliac wing 100 and the sacrum 101 at the base of the pelvis. The SI joint is fully enclosed between the iliac wing 100 and the sacrum 101 and occluded for direct visualization by the iliac wing 100. Additionally, the iliac crest 200, the posterior iliac spines, and the pedicle 104 of vertebrae S1 can be observed in this view. The iliac crest 200 may provide a posterior landmark for the entry point of the exposure device of the present invention at the posterior iliac crest, and can be palpated to find the general location of the SI joint. Alternatively, suitable locations for an incision may be determined by imaging methods (e.g., x-ray), or any other suitable method.

Figure 70:
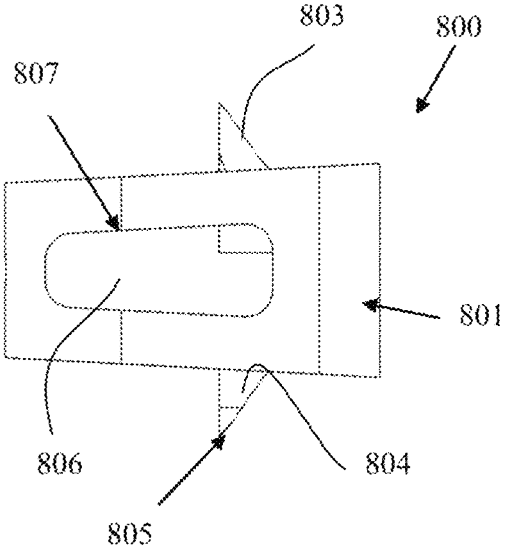
FIG. 70 is a side view of an open-body sacroiliac fusion implant having a rotatable member with lateral flukes according to an embodiment of the present invention.
Figure 71:
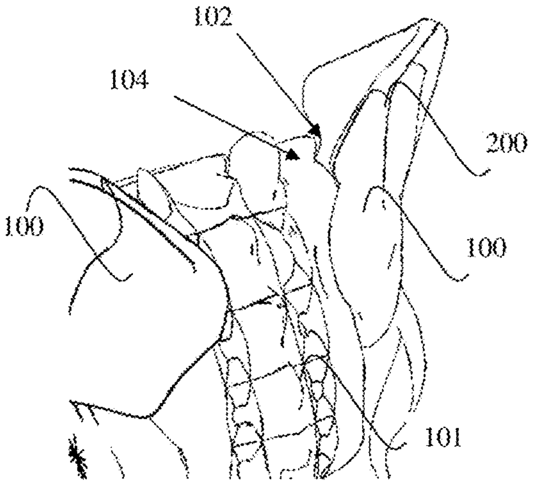
FIG. 71 is an oblique posterior view of the sacroiliac joint.
Figure 73:
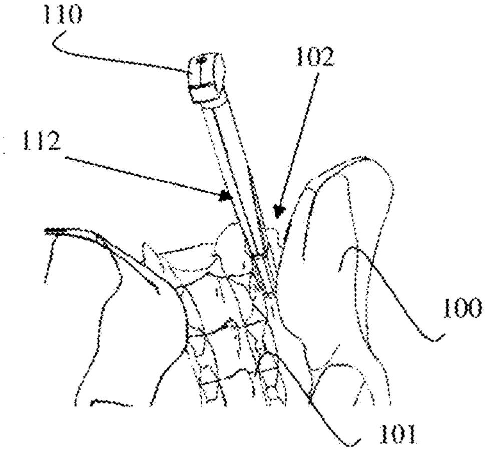
FIG. 73 is an oblique posterior view of the sacroiliac joint and a joint probe with the joint probe identifying the SI joint.
Figure 74:
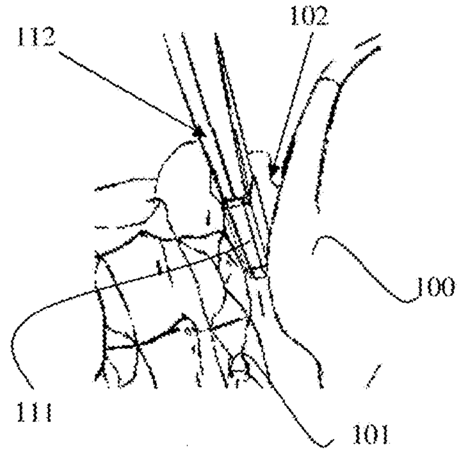
FIG. 74 is an enlarged oblique posterior view of the sacroiliac joint and a joint probe with the joint probe identifying the SI joint.
Figure 75:
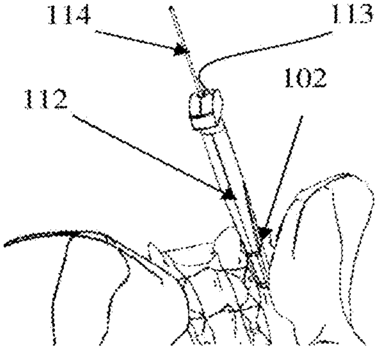
FIG. 75 is an oblique posterior view of the SI joint and a joint probe with a guide pin marking the SI joint.

As illustrated in FIG. 73-74, and without limitation, a joint probe 112 may be used to identify the insertion area on the posterior side of the SI joint. The area of the SI joint may be probed until the rounded geometry of the joint probe 112 finds or drops into the proper position in the SI joint, where an incision may be properly made. Subsequently, a guide pin 114 may be inserted through a central channel in the joint probe 112 and into the patient to create an incision in the SI joint, as illustrated in FIG. 70. Alternatively, the incision may be made by any suitable method, including scalpel or other cutting or dissection tool. The incision may be made proximal to the patient's SI joint, allowing the joint to be accessed by the exposure device. The guide pin 114 may be advanced until its proximal end is in contact with the SI joint or at least partially within SI joint.

As illustrated in FIGS. 76-79, and without limitation, a dilator may be used to dilate the incision. As an example, dilator 116 may be slotted over guide pin 114 through a central channel running the length of the dilator 116. The proximal end of the dilator 116 may be slotted over the guide pin 114, and dilator 116 may then be advanced to or near the SI joint through the incision. As dilator 116 enters the incision, the tapered end 118 pushes the patient's flesh and tissue aside, thereby dilating incision to accommodate an exposure device as described herein. A joint cutting assembly that includes the dilator 116 and a T-handle 120 engaged with a distal end of the dilator 116 may be used to further drive the dilator 116 into the incision to a desired depth to sufficiently expose the SI joint. Alternatively, an impactor (not shown) may be used to further drive the dilator 116 into the incision to a desired depth.

Figure 76:
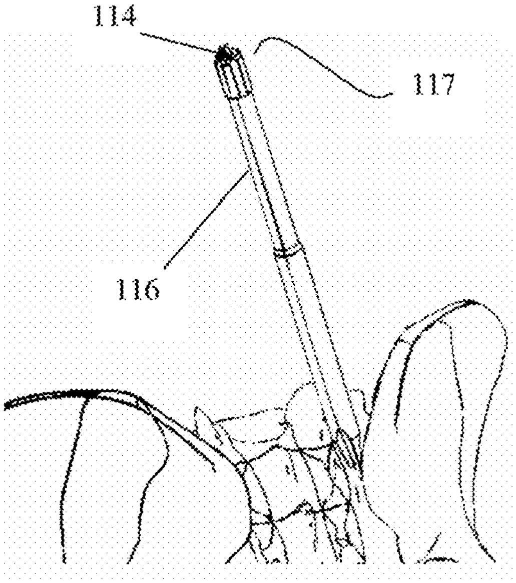
FIG. 76 is an oblique posterior view of an SI joint with a joint cutting instrument entering the joint.
Figure 77:
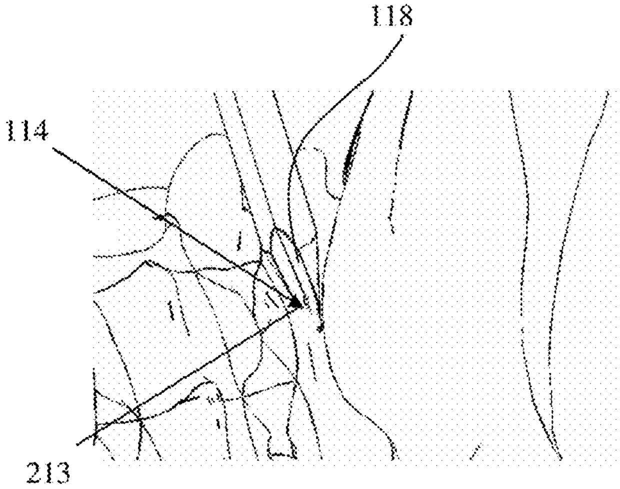
FIG. 77 is an enlarged oblique posterior view of an SI joint with a joint cutting instrument entering the joint.
Figure 78:
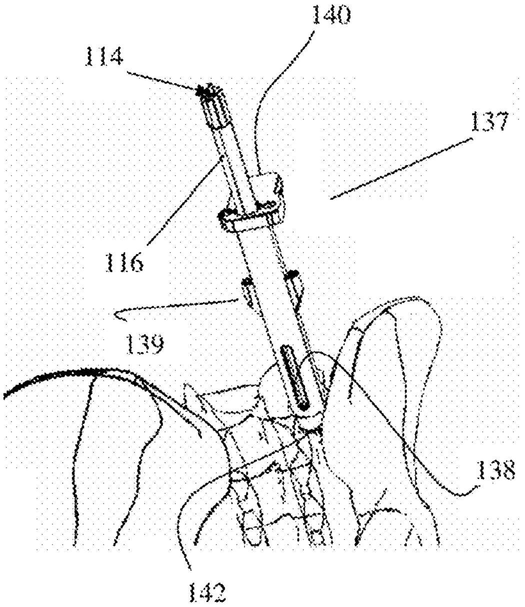
FIG. 78 is an oblique posterior view of a surgical tool according to an embodiment of the present invention inserted into an SI joint.
Figure 79:
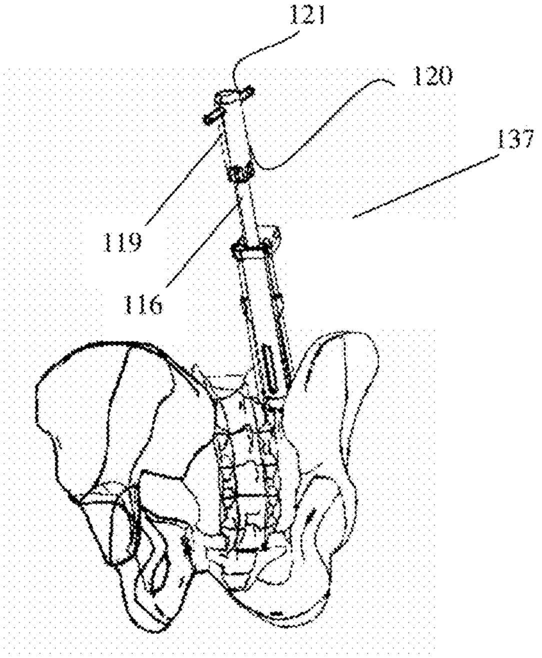
FIG. 79 is an oblique posterior view of a joint cutting assembly and a surgical tool according to an embodiment of the present invention inserted into an SI joint.
Figure 80:
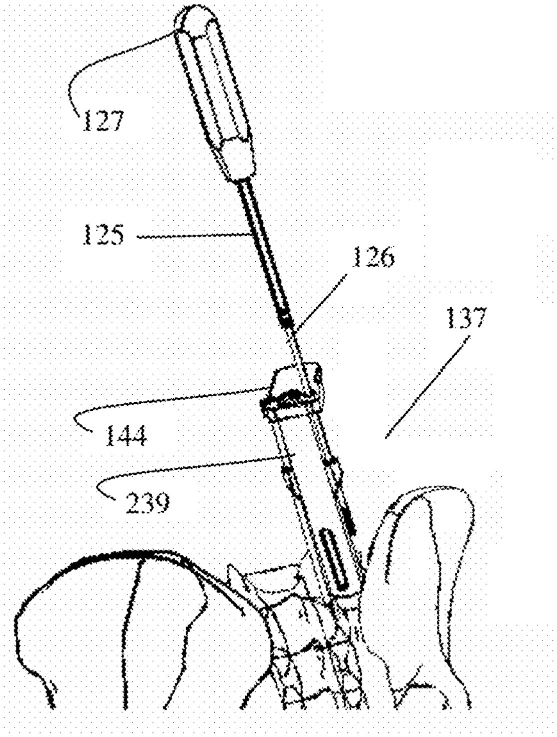
FIG. 80 is an oblique posterior view of an SI joint with a surgical tool according to an embodiment of the present invention and a fixation pin assembly.
Figure 81:
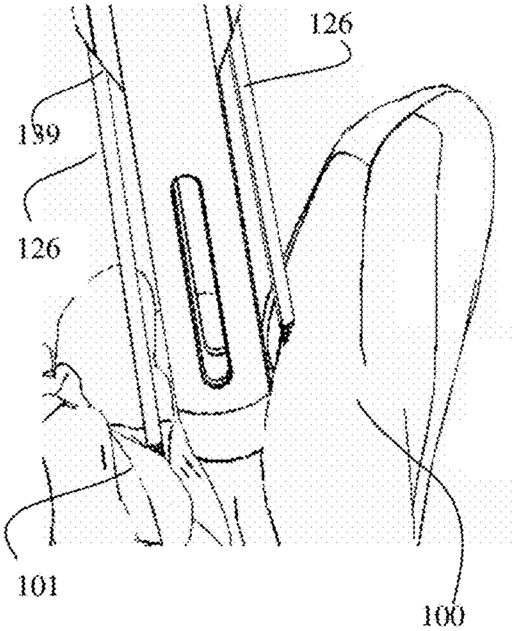
FIG. 81 is an enlarged oblique posterior view displaying a fixation pin assembly and a surgical tool according to an embodiment of the present invention.

FIG. 76 illustrates the placement of the exposure device 137 over the dilator 116. The exposure device 137 is advanced over dilator 116 and into incision. Dilator 116 enters the hollow barrel of exposure tool at the distal end of the working channel 239. The working channel 239 of the exposure tool has distal end 142 that may have a round geometry and/or a tapered rounded profile that is operable to distract the SI joint with minimal damage to soft and connective tissue in and around the posterior side of the SI joint. The working channel may include tangs extending from distal end 142 for engaging the SI joint between the sacrum and ilium. The tangs may align between the articular surfaces and help to position and stabilize the working channel. It is to be appreciated that the working channel may have other perimeter shapes such as oval, to accommodate the shape of some fusion implants. It should be understood that the working channel may have other shapes as well (e.g., triangular, polygonal [pentagonal, hexagonal, etc.], Reuleaux shapes, and other applicable shapes). The exposure device may also further dilate incision. The exposure device is advanced toward SI joint through incision until proximal end 142 is in contact with the SI joint or proximal to the SI joint and in contact with the sacrum and/or ilium. In such embodiments, dilator 116 functions to guide the proximal end 142 to the patient's SI joint.

FIGS. 78-81 illustrate a process of stabilizing the exposure device 137 within incision. As depicted, the exposure device is stabilized using fixing pins 126, slotted through fixing pin holes or slots 139 on sides of the working channel 239. Fixing pins 126 may have any suitable structure that permits them to stabilize the exposure device 137. In some embodiments, and without limitation, stabilizing pins 126 can penetrate the skin and/or flesh and tissue of a human. It is to be appreciated that any suitable method of stabilizing exposure device may be used. Dilator 116 and guide pin 115 may be removed from the working channel either before or after the fixing pins 126 are inserted. In other embodiments, and without limitation, the exposure device may be stabilized by attachment to a surgical or stabilizing arm to hold the exposure device in a static and stable position.

A guide pin 115 may be inserted into the incision through the working channel 239, either through the dilator before it is removed, or through a guide sleeve that may be used to insert the guide pin 115 and then may be removed from the working channel 239.

Figure 82:
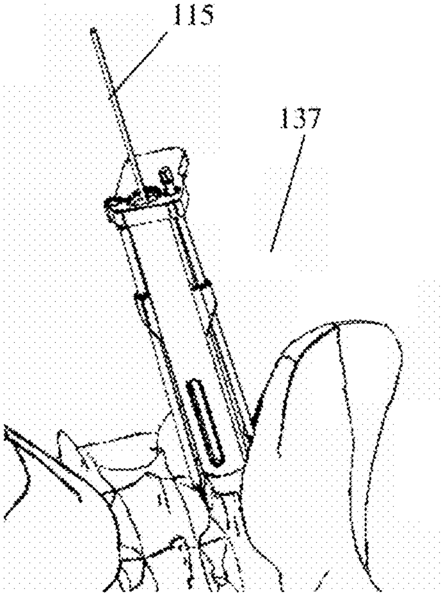
FIG. 82 is an oblique posterior view of a surgical tool according to an embodiment of the present invention inserted into an SI joint with the guide pins marking implant placements.
Figure 83:
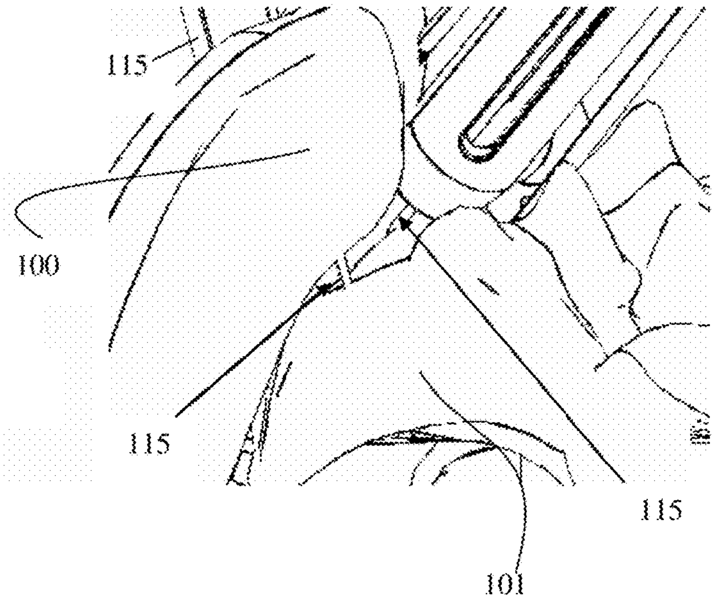
FIG. 83 is an enlarged, superior view of a surgical tool according to an embodiment of the present invention inserted into an SI joint with the guide pins marking implant placements.
Figure 84:
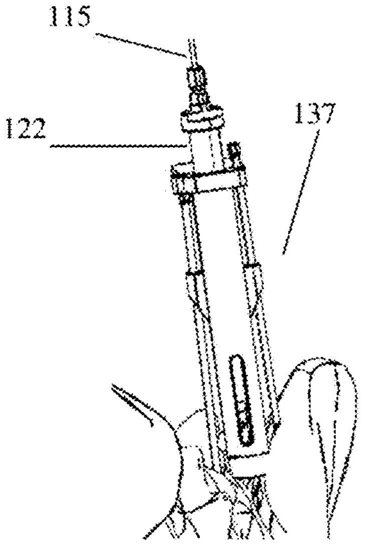
FIG. 84 is an oblique posterior view of a surgical tool according to an embodiment of the present invention inserted into an SI joint with drill bits present in working channel of the surgical tool.
Figure 85:
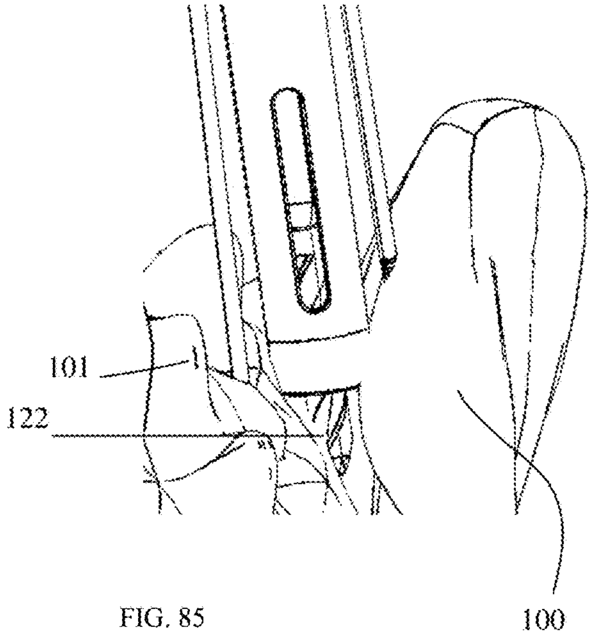
FIG. 85 is an enlarged oblique posterior view of a surgical tool according to an embodiment of the present invention inserted into an SI joint with drill bits present in working channel of the surgical tool.
Figure 86:
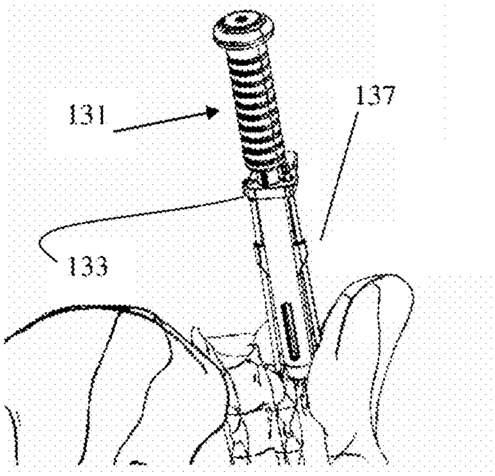
FIG. 86 is an oblique posterior view of a surgical tool according to an embodiment of the present invention inserted into an SI joint with a box chisel inserted into a working channel of the surgical tool.
Figure 87:
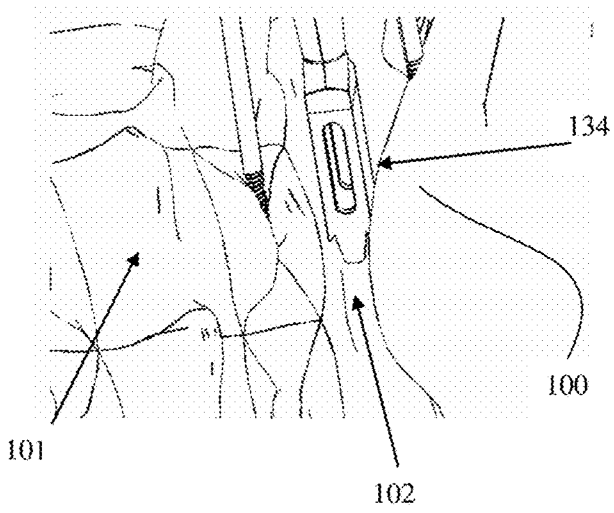
FIG. 87 is an enlarged oblique posterior view of a box chisel inserted into an SI joint, with a working channel removed from view for clarity.

FIGS. 82-83 illustrate insertion of drill bit apparatus 122 into the incisions through the working channel 239 of the exposure device 137. The drill bit may be connected to a power drill configured for medical procedures. The drill bit apparatus 122 may have cylindrical outer walls that allow the drill bit apparatus to freely spin with the hollow barrel of the working channel 239. The cylindrical outer wall may comprise a low-friction material that facilitates smooth spinning of the drill within the hollow barrel of the working channel. The proximal end of the drill bit apparatus 122 may be inserted into the working channel 239 and may be advanced to a predetermined point. In some examples, and without limitation, the proximal end of drill bit apparatus 122 does not extend past the proximal end of the working channel 239 when fully inserted. Preferably, drill bit apparatus 122 may be configured such that it will interact with the working channel 239 only in an orientation that ensures proper positioning of drill bit apparatus 122 relative to the SI joint. For example, and without limitation, the drill bit apparatus may fit snugly into the hollow barrel to avoid any axial deviations, but may still be able to spin freely and at a rapid rotational speed without causing excessive friction or causing significant extraneous or unwanted motion. In other embodiments, and without limitation, the drill bit may have an outer stationary housing that is complementary to and fits snugly within the hollow barrel of the working channel, and the rotating portion of the bit may be within the outer stationary housing and can be rotated while the stationary outer housing is statically engaged with the hollow barrel of the working channel.

In some implementations, and without limitation, the drill bit in the drill bit apparatus 122 may be advanced into the working channel 239 toward SI joint to a predetermined depth. This may be accomplished by an arrestor system in the drill that only allows a particular depth of insertion or by any other suitable method. The drill bit in the working channel 239 may be positioned such that when activated it will create a void in the patient's SI joint by displacing portions of sacrum and ilium. In such examples, the drill bit may be configured such that it will contact the patient's SI joint at a desired portion of the joint and, once activated, will create a void of a desired depth. The void may be configured to receive a fusion implant as described herein or other joint repairing appliance or bone graft for fusing the SI joint. Other joint repairing appliances or apparatus may include a polyether ether ketone (PEEK) implant, a titanium implant, etc. As an example and without limiting the invention, the implant may be a fusion implant like one of those shown in FIGS. 49-70.

Figure 88:
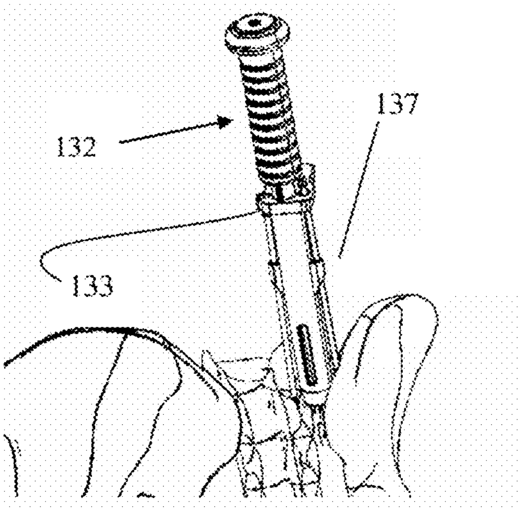
FIG. 88 is an oblique posterior view of a surgical tool according to an embodiment of the present invention inserted into an SI joint with a rasp inserted into a working channel of the surgical tool.
Figure 89:
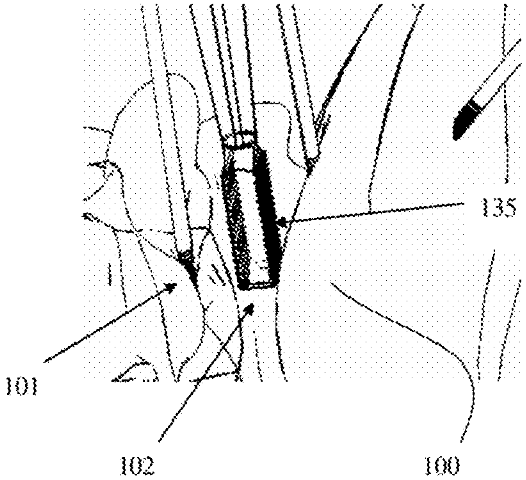
FIG. 89 is an enlarged oblique posterior view of a rasp inserted into an SI joint, with a working channel removed from view for clarity.

As shown in FIGS. 84-93, several implements may be inserted through the working channel 239 into the void in the SI joint to prepare the void for receiving a fusion implant. For instance, a box chisel 131 and/or a rasp 132 may be inserted into the void through the working channel 239 to expand and clear tissue from the void to facilitate a clean and efficient insertion of the fusion implant into the void (see, e.g., FIGS. 84-86). As shown in FIGS. 88-89, an impactor 136 may also be used to deepen or spread the void.

Figure 90:
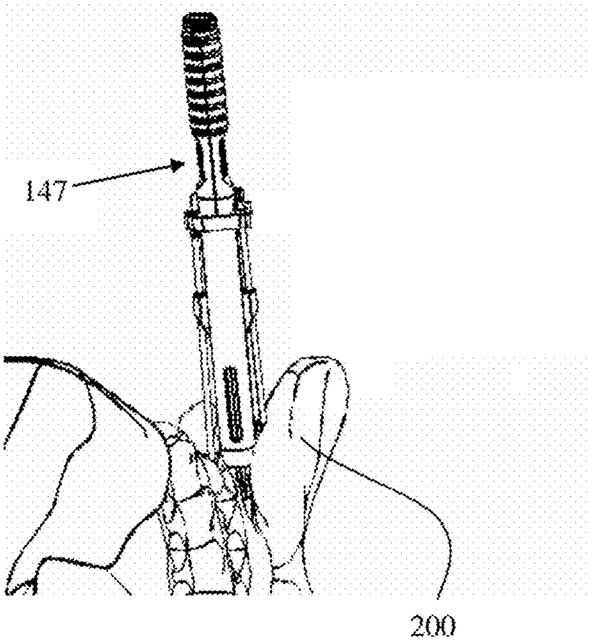
FIG. 90 is an oblique posterior view of a surgical tool according to an embodiment of the present invention inserted into an SI joint with a fusion implant inserter inserted into a working channel of the surgical tool.

FIGS. 39 and 90 illustrate the use of a fusion implant inserter 147 to insert a fusion implant into the void in the SI joint. The inserter 147 may be inserted into the working channel 239 of the exposure device 137 once a void has been formed in the SI joint. For example, and without limitation, prior to insertion, the fusion implant is grasped by forceps of the inserter 147, which may engage with grooves along sides of the fusion implant. In other examples, and without limitation, the inserter may have a head that is threaded, keyed, or otherwise structured such that it is complementary to a hole in the proximal end of the fusion implant (e.g., the proximal hole in fusion implant 700 or 800). Once engaged with the fusion implant, the inserter 147 may be inserted into the working channel and may be advanced until it meets resistance at the void. The inserter 147 may be operable to then release the fusion implant, leaving it in the void. In some examples, the inserter 147 may have a mechanism for grasping and releasing the fusion implant (e.g., arms 149 may be operable to clamp and release the fusion implant), providing an efficient means of depositing the fusion implant in the void.

In some implementations, and without limitation, the fusion implant may require that one or more elements thereof be rotated in order for the fusion implant to engage with the bone tissue in the SI joint (e.g., fusion implants 400, 400*a*, 500, 800, and other related embodiments). In some implementations, and without limitation, the inserter may have arms thereon for engaging slots or notches in the proximal end of the fusion implant and may be capable of rotating the fusion implant (e.g., fusion implants 400, 400*a*, 500, and related embodiments) once it is placed in the SI joint. In such implementations, the inserter may have distal rotatable member that is capable of rotating independently of shaft and handle of the inserter, allowing the surgeon to use the inserter to place the fusion implant into the void in the proper orientation without unwanted rotation and then deliberately rotate the fusion implant and engage it with the articular surfaces. In other implementations, and without limitation, the inserter may include a distal head that may be operable to engage a hole in the proximal surface of the fusion implant, which may be threaded or machined (e.g., to have gear teeth, notches, angular sides [e.g., a square shape, etc.] or other features) in a manner to allow an interlocking fit with the distal head of the inserter. In such implementations, the distal head may be operable to rotate the fusion implant once it is placed in the void in the SI joint. In other implementations, and without limitation, a tool separate from the inserter may be used to rotate the fusion implant once it is in place within the SI joint. For example, and without limitation, a driver having a distal head operable to engage the fusion implant may be passed through the working channel and engage with the fusion implant, and subsequently rotate the fusion implant.

Figure 91:
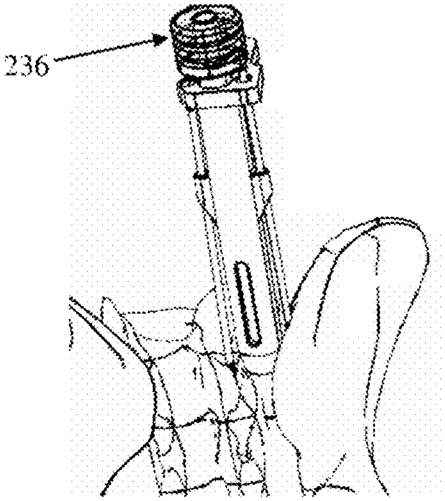
FIG. 91 is an oblique posterior view of a surgical tool according to an embodiment of the present invention inserted into an SI joint with an impactor inserted into a working channel of the surgical tool.

An impactor 236 may be used to exert force on the fusion implant as it is in the void, in order to drive the fusion implant securely into the void, as shown in FIG. 91. The impactor may be utilized to drive the fusion implant into the bone tissue of the articular surfaces of the SI joint, particularly in implementations that utilize a fusion implant having lateral blades (e.g., fusion implant 700 and related embodiments). The fusion implant may thereby be properly inserted into the void. Though, the impactor may be used in other implementations as well, for example, to drive the fusion implant deeper into the void prior to rotating the fusion implant (e.g., fusion implants 400, 400*a*, 500, and related embodiments), or prior to driving screws of the fusion implant into the articular surfaces of the SI joint (e.g., fusion implant 600 and related embodiments). Additionally, the impactor 236 may be used to add additional therapeutic materials, such as bone morphogenetic proteins (BMP), demineralized bone matrix (DBM), stem cells, and other materials, to the void to improve recovery and growth of the bone in the SI joint.

Subsequently, the exposure device may be removed from the patient. Also, the fixing pins 126 may be removed from both incisions. The tissues in the incisions may then be sutured, to facilitate healing.

In some embodiments of the present invention, and without limitation, surgical fusion may be accomplished with the delivery of both (1) a fusion implant device into the SI joint, and (2) a separate fixation device which can be in the form of a screw, or the like. The fusion may be delivered to the SI joint, placed between the sacrum and ilium, while the fixation device may be delivered through the iliac wing, near the iliac crest, into the sacrum while not entering or passing through the SI joint. In such embodiments, the steps of locating the SI joint and making an incision over the SI joint may be the same or similar to the steps described above and as shown in FIGS. 71-77.

Figure 92:
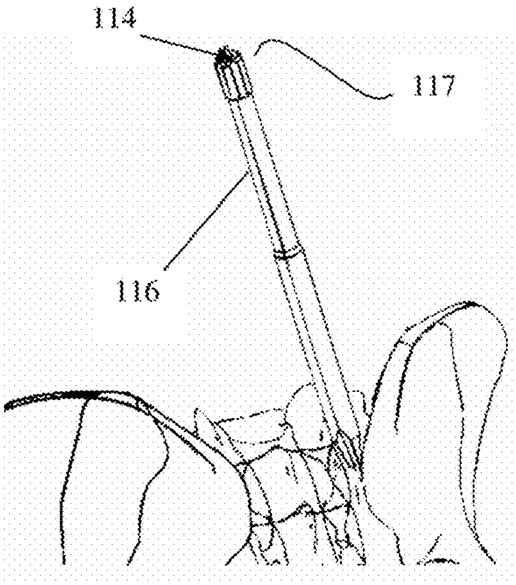
FIG. 92 is an oblique posterior view of an SI joint with a joint cutting instrument entering the joint.
Figure 93:
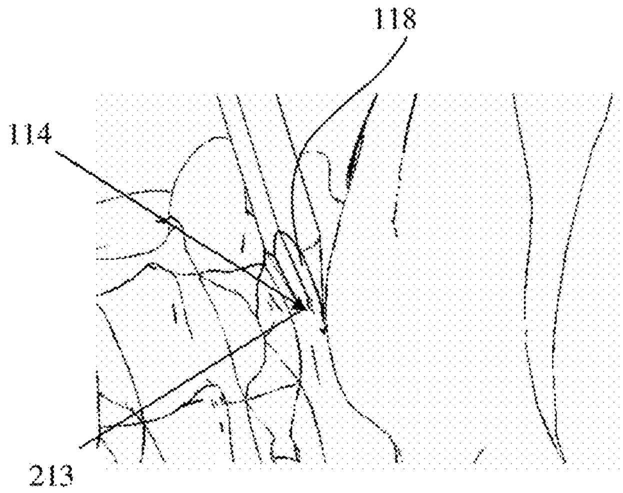
FIG. 93 is an enlarged oblique posterior view of an SI joint with a joint cutting instrument entering the joint.

FIGS. 92-114 illustrate additional steps of a surgical procedure for fusing an SI joint with both a fusion implant inserted in the SI joint and a joint fixation device (e.g., a bone screw) fixing the ilium and sacrum together. The procedure may include making an incision over the iliac wing near the iliac crest for the insertion of a second working channel of a double-barreled, double-angled exposure device. A dilator may be used to dilate an incision formed over the SI joint, as previously described. As an example, and without limitation, FIGS. 92-93 show dilator 116 may be slotted over a guide pin 114 through a central channel running the length of the dilator 116. The proximal end of the dilator 116 may be slotted over the guide pin 114, and dilator 116 may then be advanced to or near the SI joint through incision. As dilator 116 enters the incision, the tapered end 118 pushes the patient's flesh and tissue aside, thereby dilating incision to accommodate exposure device. A joint cutting assembly that includes the dilator 116 and a T-handle 120 engaged with a distal end of the dilator 116 may be used to further drive the dilator 116 into the incision to a desired depth to sufficiently expose the SI joint. Alternatively, an impactor (not shown) may be used to further drive the dilator 116 into the incision to a desired depth.

Figure 94:
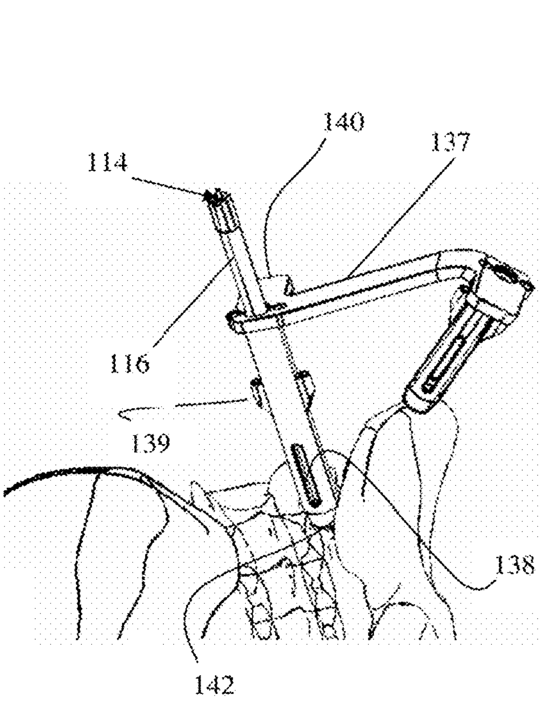
FIG. 94 is an oblique posterior view of a surgical tool engaged with the sacroiliac joint and the iliac wing according to an embodiment of the present invention inserted into an SI joint.
Figure 95:
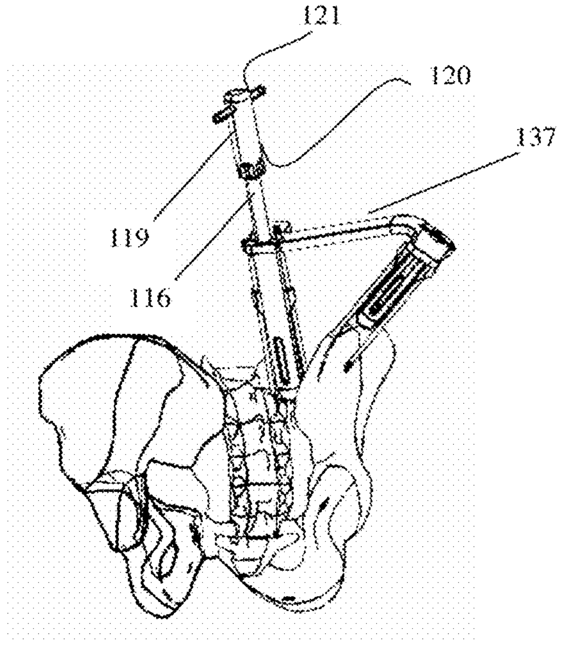
FIG. 95 is an oblique posterior view of a joint cutting assembly and a surgical tool engaged with the sacroiliac joint and the iliac wing according to an embodiment of the present invention inserted into an SI joint.
Figure 96:
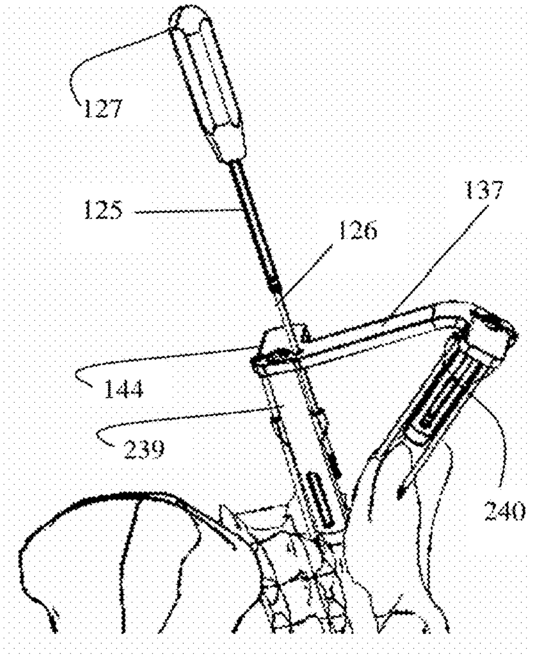
FIG. 96 is an oblique posterior view of an SI joint with a surgical tool and a fixation pin assembly engaged with the sacroiliac joint and the iliac wing according to an embodiment of the present invention.
Figure 97:
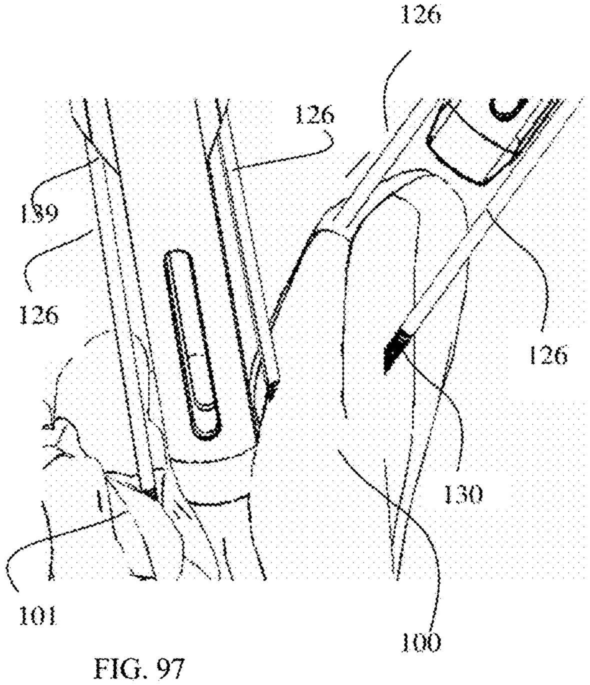
FIG. 97 is an enlarged oblique posterior view displaying a fixation pin assembly and a surgical tool engaged with the sacroiliac joint and the iliac wing according to an embodiment of the present invention.
Figure 98:
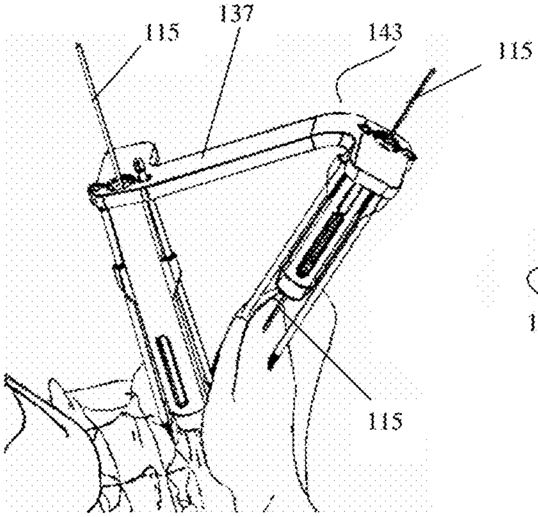
FIG. 98 is an oblique posterior view of a surgical tool with the guide pins engaged with the sacroiliac joint and the iliac wing according to an embodiment of the present invention inserted into an SI joint.
Figure 99:
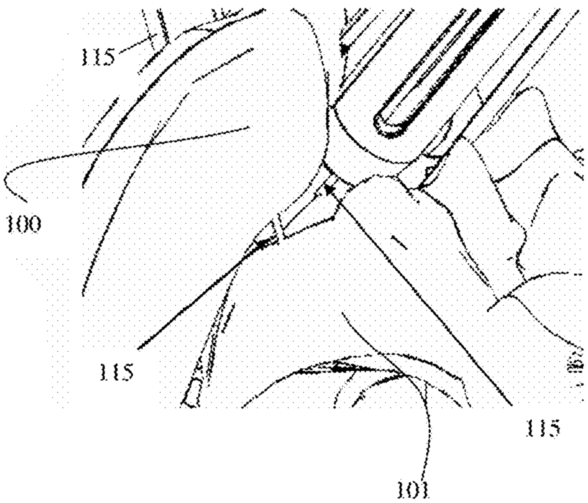
FIG. 99 is an enlarged, superior view of a surgical tool with the guide pins engaged with the sacroiliac joint and the iliac wing according to an embodiment of the present invention.

FIGS. 94-95 illustrate the placement of the double-barreled, double-angled exposure device over the dilator 116. The exposure device is advanced over dilator 116 and into incision. Dilator 116 enters the hollow barrel of exposure tool at the distal end of the first working channel 239. Without limiting the invention, the first working channel 239 of the exposure tool has proximal end 142 that may have a round geometry and/or a tapered rounded profile that is operable to distract the SI joint with minimal damage to soft and connective tissue in and around the posterior side of the SI joint. It is to be appreciated that the working channel may have other perimeter shapes circular, oval, triangular, polygonal (pentagonal, hexagonal, etc.), Reuleaux shapes, and other applicable shapes. The exposure device may also further dilate incision. The exposure device is advanced toward SI joint through incision until proximal end 142 is in contact with the SI joint or proximal to the SI joint and in contact with the sacrum and/or ilium. In such embodiments, dilator 116 functions to guide the proximal end 142 to the patient's SI joint.

The exposure device may be configured such that when the first working channel 239 of the exposure device is established in position in or near the SI joint the second working channel 240 is oriented over the iliac wing near the iliac crest (the location of the incision) and in an orientation that will allow the second working channel to guide a drill bit through the ilium and sacrum (e.g., the S1 vertebra) without traversing the SI joint (i.e., without causing damage to the SI joint). The relative position of the first and second working channels of the double-barreled, double-angled exposure device accommodates the contour of the pelvis between the ilium and the SI joint such that said first working channel can be engaged with a posterior side of the SI joint and said second working channel can be engaged with a posterior portion of the iliac wing at an angle that is aligns a longitudinal axis of the second working channel anterior to the SI joint.

FIGS. 96-99 illustrate a process of stabilizing the exposure device within incision. As depicted, the exposure device is stabilized using fixing pins 126, slotted through fixing pin holes or slots 139 on sides of the first and second working channels 239 and 240. Fixing pins 126 may have any suitable structure that permits them to stabilize the exposure device. In some embodiments, stabilizing pins 126 can penetrate the skin and/or flesh and tissue of a human. It is to be appreciated that any suitable method of stabilizing exposure device may be used. Dilator 116 and guide pin 115 may be removed from the first working channel either before or after the fixing pins 126 are inserted.

Figure 100:
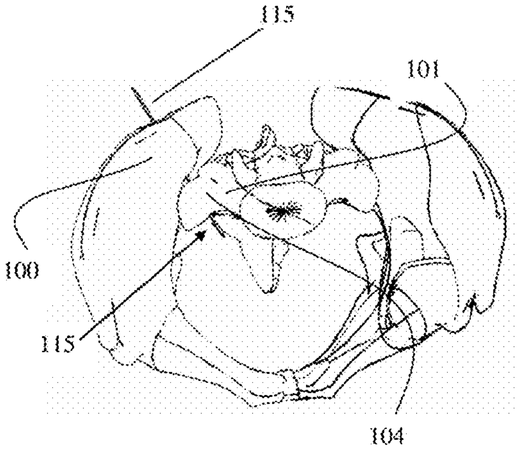
FIG. 100 is a superior view of guide pin placements according to an embodiment of the present invention.
Figure 101:
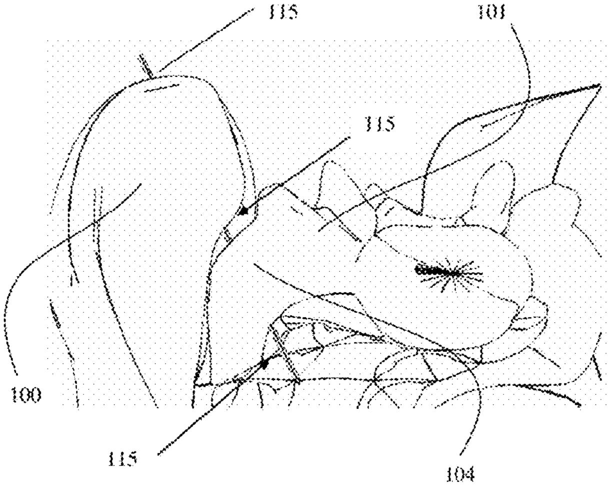
FIG. 101 is an enlarged superior view of guide pin placements according to an embodiment of the present invention.
Figure 102:
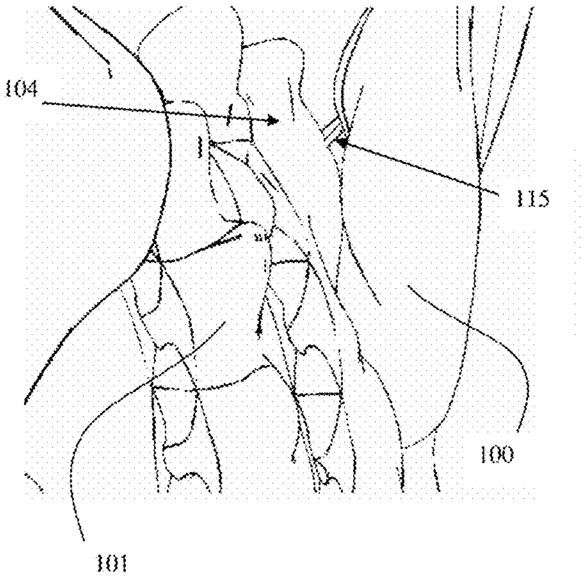
FIG. 102 is an enlarged, posterior view of guide pin placements according to an embodiment of the present invention.
Figure 103:
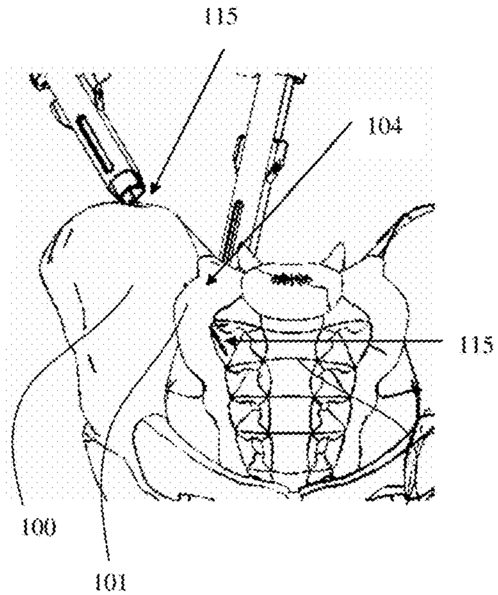
FIG. 103 is an anterior view of a surgical tool according to an embodiment of the present invention inserted into an SI joint with guide pins for guiding fusion implant placement.
Figure 104:
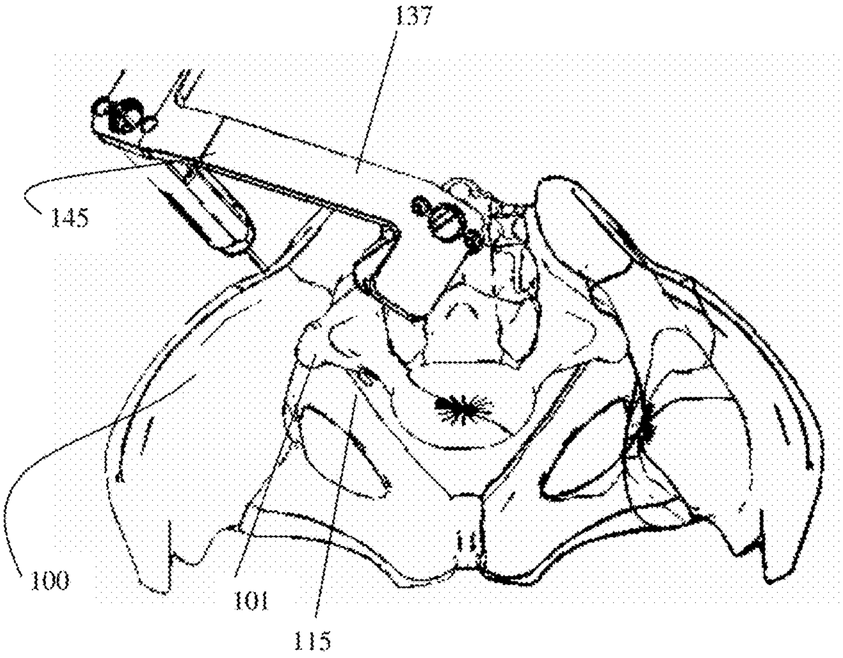
FIG. 104 is a superior view of a surgical tool according to an embodiment of the present invention engaged into an SI joint with guide pins for guiding fusion implant placement.

Guide pins 115 may be inserted into the incision through the first and second working channels 239 and 240, either through the dilator before it is removed, or through guide sleeves that may be used to insert the guide pins 115 and that may then be removed from the first and second working channels 239 and 240. FIGS. 100-102 provide views of exemplary guide pin placement for the double-barreled exposure device from multiple perspectives. FIGS. 103-104 provide views of exemplary placement of the double-barreled exposure device from multiple perspectives.

Figure 105:
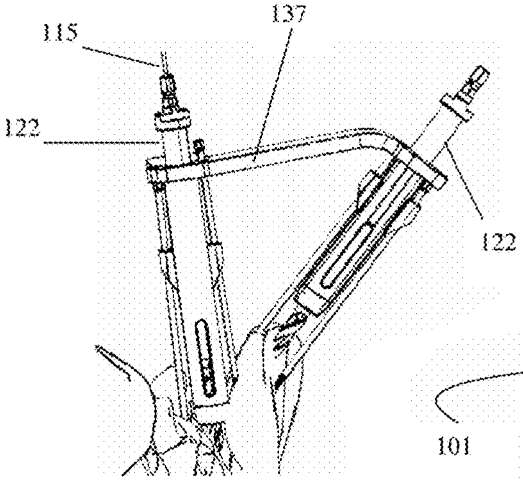
FIG. 105 is an oblique posterior view of a surgical tool according to an embodiment of the present invention engaged with an SI joint and the iliac wing with drill bits present in working channels of the surgical tool.
Figure 106:
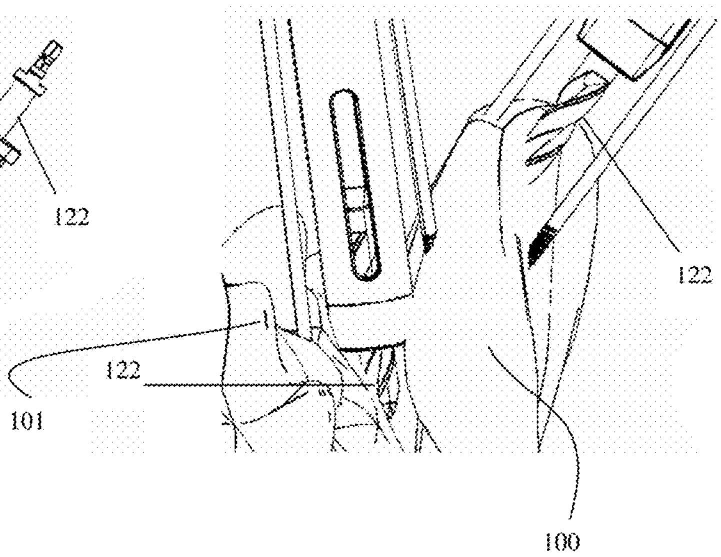
FIG. 106 is an enlarged oblique posterior view of a surgical tool according to an embodiment of the present invention engaged with an SI joint and the iliac wing with drill bits present in working channels of the surgical tool.
Figure 107:
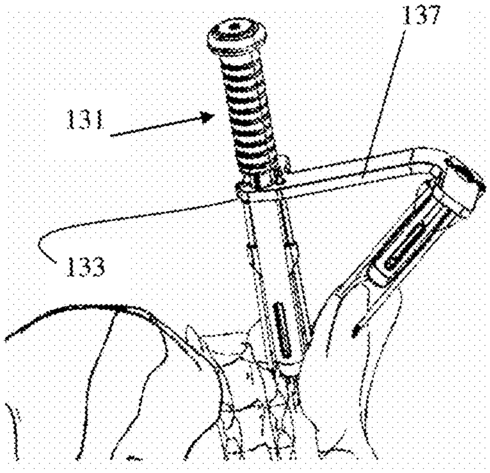
FIG. 107 is an oblique posterior view of a surgical tool according to an embodiment of the present invention engaged with an SI joint and the iliac wing with a box chisel inserted into a working channel of the surgical tool.
Figure 108:
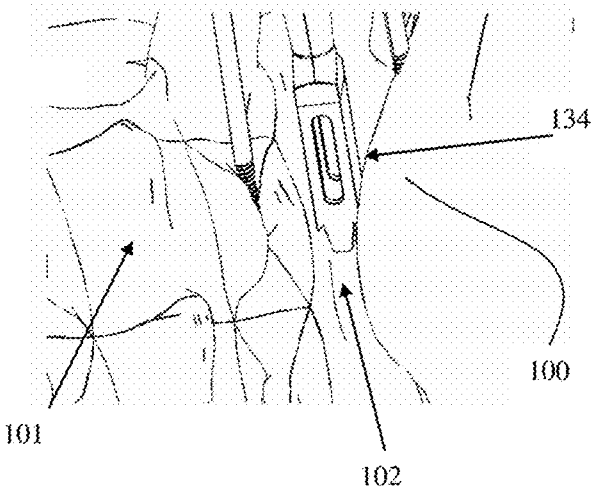
FIG. 108 is an enlarged oblique posterior view of a box chisel inserted into an SI joint, with a working channel removed from view for clarity.
Figure 109:
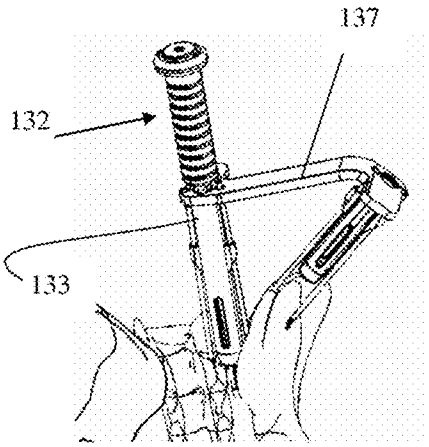
FIG. 109 is an oblique posterior view of a surgical tool according to an embodiment of the present invention engaged with an SI joint and the iliac wing with a rasp inserted into a working channel of the surgical tool.

FIGS. 105-106 illustrate insertion of drill bit apparatus 122 into the incisions through the first and second working channels 239 and 240 of the exposure device. The drill bit may be connected to a power drill configured for medical procedures. The drill bit apparatus 122 may have cylindrical outer walls that allow the drill bit apparatus to freely spin with the hollow barrel of the first and second working channels 239 and 240. The cylindrical outer wall may comprise a low-friction material that facilitates smooth spinning of the drill within the hollow barrels of the first and second working channels. The proximal ends of the drill bit apparatus 122 may be inserted into the first and second working channels 239 and 240 and may be advanced to a predetermined point. In some examples, the proximal ends of drill bit apparatus 122 do not extend past the proximal end of the first and second working channels 239 and 240 when fully inserted. Preferably, drill bit apparatus 122 are configured such that it will interact with the first and second working channels 239 and 240 only in an orientation that ensures proper positioning of drill bit apparatus 122 relative to the SI joint and the ilium. For example, the drill bit apparatus may fit snugly into the hollow barrel to avoid any axial deviations, but may still be able to spin freely and at a rapid rotational speed without causing excessive friction or causing significant extraneous or unwanted motion. In other embodiments, and without limitation, the drill bit may have an outer stationary housing that is complementary to and fits snugly within the hollow barrel of the working channel, and the rotating portion of the bit may be within the outer stationary housing and can be rotated while the stationary outer housing is statically engaged with the hollow barrel of the working channel.

The drill bits in the drill bit apparatus 122 may be advanced into channel the first and second working channels 239 and 240. With regard to the drill in the first working channel 239, the drill bit is advanced toward SI joint to a predetermined depth. This may be accomplished by an arrestor system in the drill that only allows a particular depth of insertion or by any other suitable method. The drill bit in the first working channels 239 may be positioned such that when activated it may create a void in the patient's SI joint by displacing portions of sacrum and ilium. In such examples, the drill bit may be configured such that it will contact the patient's SI joint at a desired portion of the joint and, once activated, will create a void of a desired depth.

The void may be configured to receive a fusion implant as described herein or other joint repairing appliance or apparatus for fusing the SI joint. Other joint repairing appliances apparatus may include a polyether ether ketone (PEEK) implant, a titanium implant, etc. As an example and without limiting the invention, the implant may be a fusion implant like one of those shown in FIGS. 49-70. The fusion implant may also have slots for receiving forceps of an inserter tool or a hole or recess in a proximal end of the fusion implant for receiving an inserter tool, and transverse holes to allow bone tissue to grow through the implant, and incorporate the implant into the native bone tissue, thereby fusing the SI joint.

The drill bit in the second working channels 239 may be positioned such that when activated it will drill a hole through the iliac wing of the patient near the iliac crest and through the sacrum (e.g., the S1 vertebra). The drill bit may have sufficient length to reach the S1 vertebra from the iliac wing position of the second working channel. The relative angled position of the first and second working channels 239 and 240 of the exposure device positions the second working channel such that the drill bit can be advanced through to the S1 vertebra without traversing (passing through) the SI joint, thereby avoiding any damage to the SI joint tissues (e.g., the ligaments).

As shown in FIGS. 107-112, several implements may be inserted through the first working channel 239 into the void in the SI joint to prepare the void for receiving a fusion implant. For instance, and without limitation, a box chisel 131 and or a rasp 132 may be inserted into the void through the first working channel 239 to expand and clear tissue from the void to facilitate a clean and efficient insertion of the fusion implant into the void. An impactor 136 may also be used to deepen or spread the void.

Figure 113:
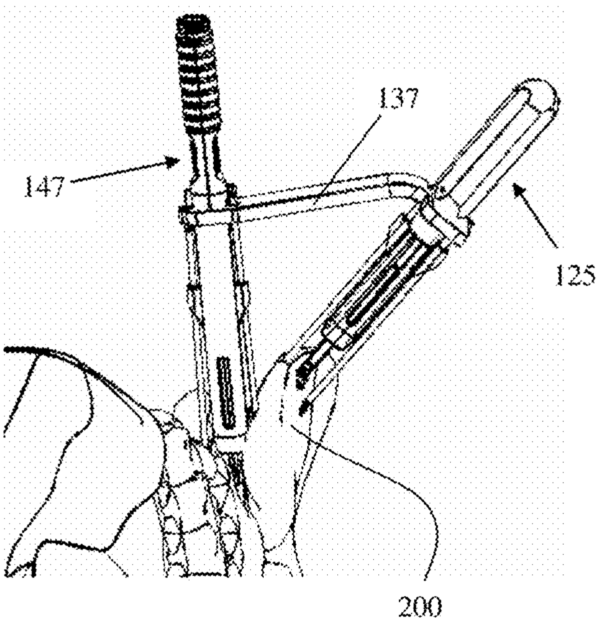
FIG. 113 is an oblique posterior view of a surgical tool according to an embodiment of the present invention inserted into an SI joint with a fusion implant inserter placed in a working channel of the surgical tool.

FIGS. 39 and 113 illustrate the use of a fusion implant inserter 147 to insert a fusion implant (e.g., as described above and shown in FIGS. 49-70) into the void in the SI joint. The inserter 147 may be inserted into the first working channel 239 of the exposure device. Prior to insertion, the fusion implant may be grasped by the forceps of the inserter 147, which may engage with grooves or recesses on the fusion implant. In other implementations, and without limitation, the fusion implant may have a hole or recess in a proximal end of the fusion implant for receiving an inserter tool, and the inserter tool may have a head or extension that fits within the hole or recess. The inserter 147 and the fusion implant may be inserted together into the first working channel and may be advanced until it meets resistance at the void. The inserter 147 may then release the fusion implant, leaving it in the void. In some examples, the inserter 147 may have a mechanism for grasping and releasing the fusion implant, providing an efficient means of depositing the fusion implant in the void.

Figure 114:
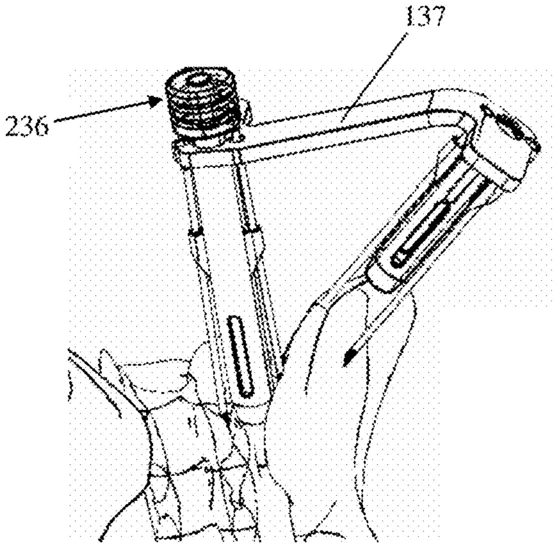
FIG. 114 is an oblique posterior view of a surgical tool according to an embodiment of the present invention inserted into an SI joint with an impactor inserted into a working channel of the surgical tool.

Subsequently, an impactor 236 may be used to exert force on the fusion implant in the void, in order to drive fusion implant securely into the void, as shown in FIG. 114. The fusion implant may thereby be properly inserted into the void. Additionally, the impactor 236 may be used to add therapeutic materials, such as bone morphogenetic proteins (BMP), demineralized bone matrix (DBM), stem cells, and other materials, to the void to improve recovery and growth of the bone in the SI joint.

A joint fixation device (e.g., a compression screw) may be inserted into the iliac wing and the sacrum (the S1 vertebra) through the second working channel as the double-barreled exposure device is secured to the SI joint and the ilium. A fixation device 158 may be inserted at angle into the ilium and the sacrum that compresses the SI joint, thereby compressing the fusion implant within the SI joint. However, in other embodiments, the angle of the hole drilled in the ilium and sacrum in an orientation that distracts the SI joint, providing room in the SI joint for bone tissue grow around the fusion implant. In further embodiments, the structure of the joint fixation device 158 may be configured to create distraction in the SI joint.

Figure 115:
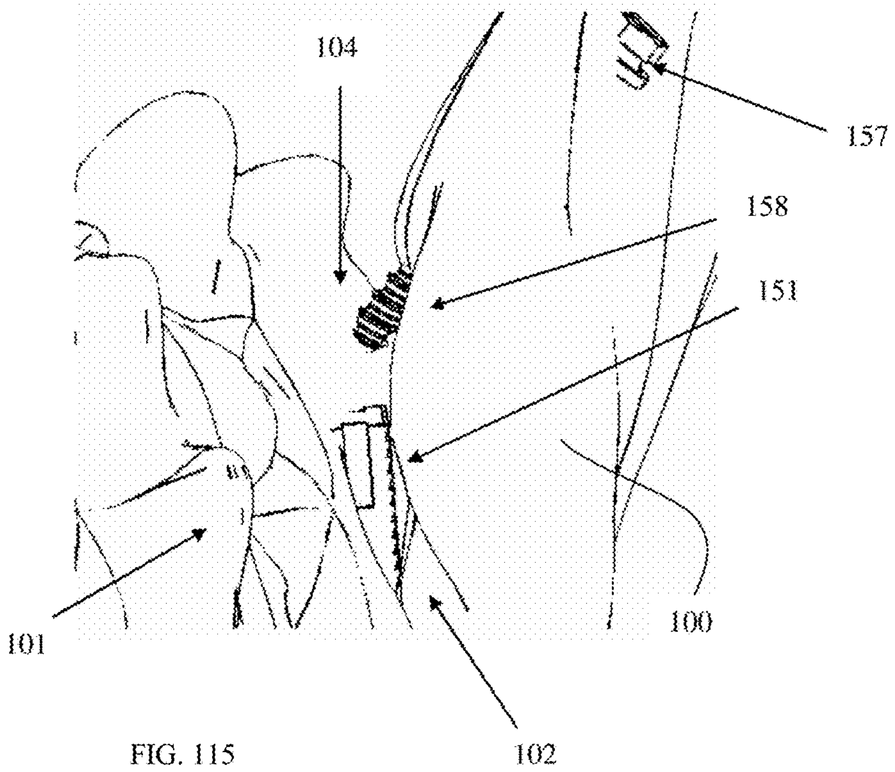
FIG. 115 is an enlarged, oblique view of a fusion implant and a fixation implant in place in the sacroiliac joint and the iliac wing and sacrum, respectively, where the fixation implant does not pass through the sacroiliac joint.
Figure 116:
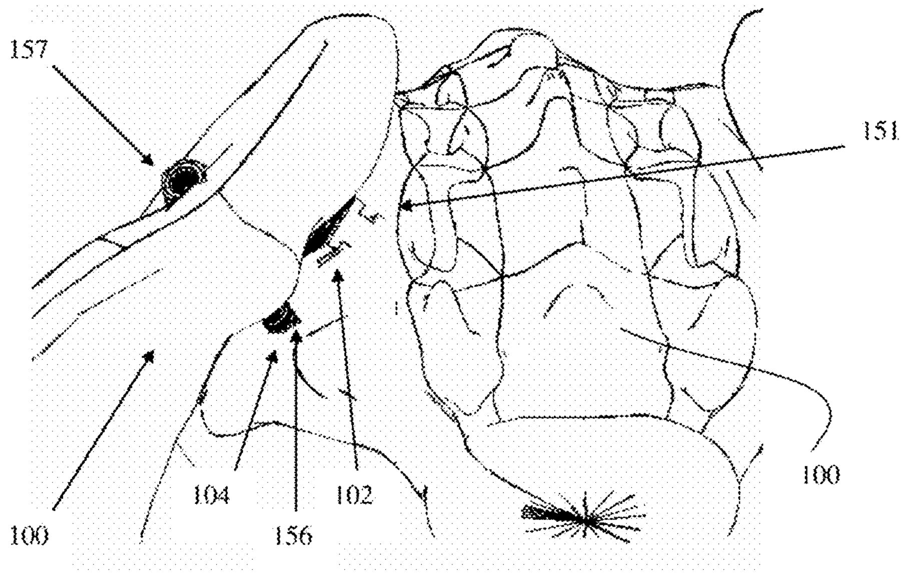
FIG. 116 is an enlarged, superior view of a fusion implant and a fixation implant in place in the sacroiliac joint and the iliac wing and sacrum, respectively.

The joint fixation device 158 may be inserted into the second working channel along with a fixation implant driver 125 engaged therewith. In the case of a screw, the screw 158 may be advanced into the hole drilled through the ilium and the sacrum manually with a specialized driver 125. Alternatively, the screw or other fusion device can be installed by an automated process. Without limiting the invention, FIGS. 115-116 show an exemplary fixation device 158 and an exemplary fusion implant 151 positioned in the pelvis from posterior and superior views, respectively. The fusion implant 151 sits in the SI joint 102 between the articular surfaces of the sacrum 101 and the iliac wing 100. The fixation device 158 passes through the iliac wing 100 and into the body of S1 of the sacrum 101 without traversing (passing through) the SI joint 102.

Once the fusion implant 151 and the fixation device 158 are implanted in their proper positions, the fixation implant insertion implant device 125 and the double-barreled exposure device may be removed from the patient. Also, the fixing pins 126 may be removed and the exposure device may be removed from both incisions. The tissues in the incisions may then be sutured, to facilitate healing.

Figure 117:
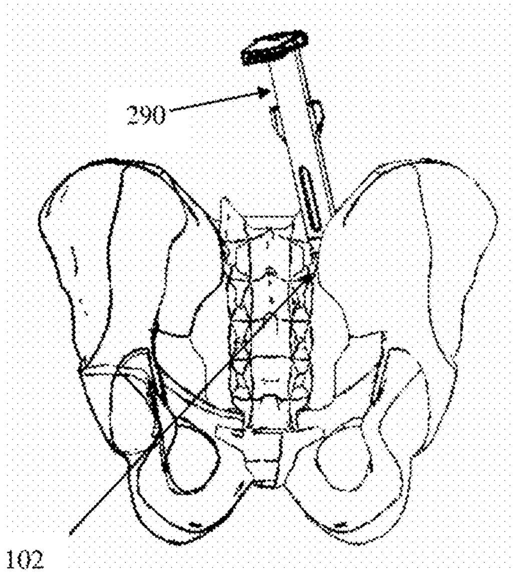
FIG. 117 is a posterior view of a pelvis with a surgical tool according to an embodiment of the present invention inserted into an SI joint.
Figure 118:
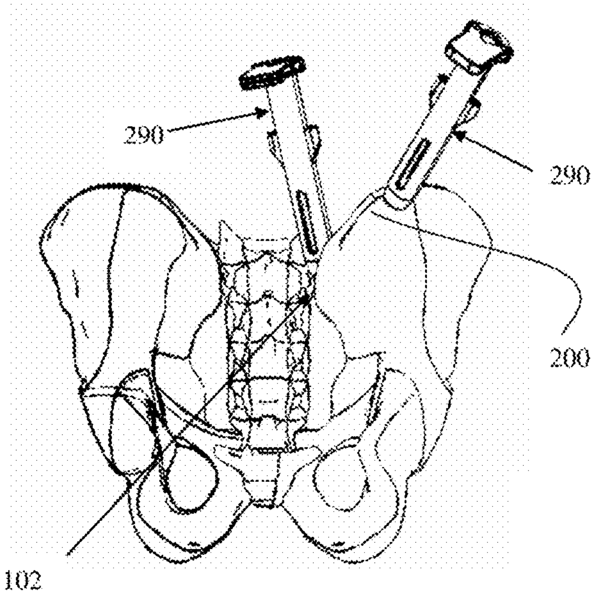
FIG. 118 is a posterior view of a pelvis with a surgical tool according to an embodiment of the present invention with two independent working channels, one inserted into an SI joint and one positioned over an iliac crest.
Figure 119:
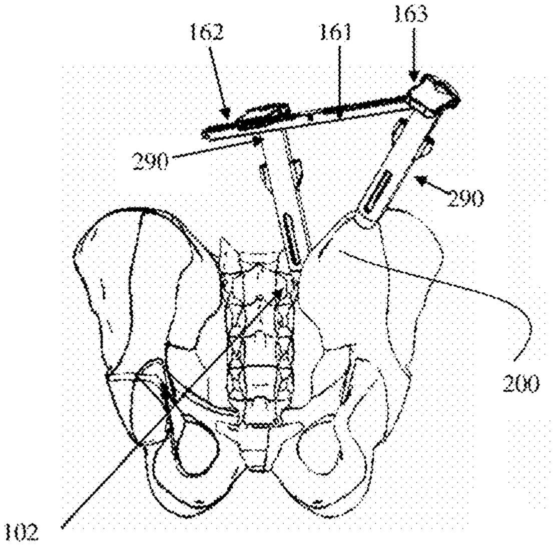
FIG. 119 is a posterior view of a pelvis with a surgical tool according to an embodiment of the present invention with two independent working channels attached by an adjustable rack.

In some embodiments, and without limitation, the working channels may have different structures and orientations. Without limiting the invention, FIGS. 117-120 illustrate further embodiments of the invention. In FIG. 117, a single working channel 290 is shown engaged with the SI joint. In this example, the single working channel 290 can be individually orientated and engaged with the SI joint, and separately as second working channel 290 may be engaged with the preferred insertion point on the ilium, as shown in FIG. 118. This embodiment provides the flexibility of individually orienting the two working channels. Subsequently, an adjustable rack 161 may be engaged with both the of the individual working channels 290 as shown in FIG. 119, thereby stabilizing the two working channels and maintaining their orientation relative to one another. It is to be appreciated that the two working channels in this example may be stabilized by other or additional methods.

Figure 120:
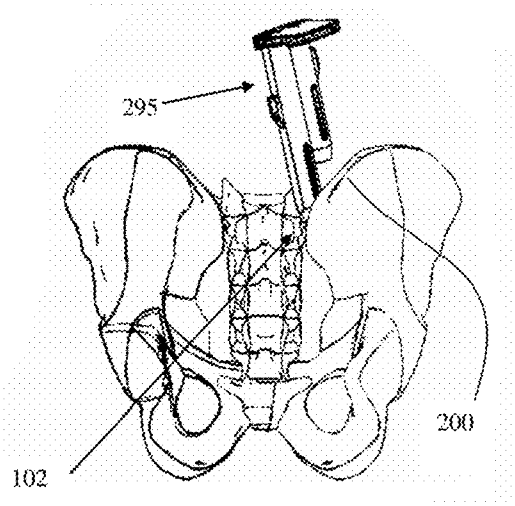
Figure 121:
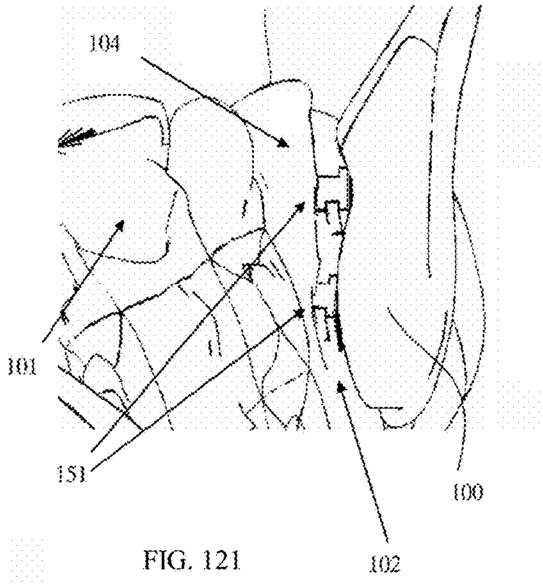

In some embodiments, the working channel may have two barrel or more barrels (e.g., 3, 4, or more barrels, in various orientations—parallel, skewed, etc.), each capable of receiving surgical implements and being used to introduce implants or other devices or materials into the SI joint. For instance, the two or more barrels may include two parallel barrels, two skewed barrels, three parallel barrels in a single plane, three parallel barrels in a triangular arrangement, etc. As an example, and without limiting the invention, FIG. 120 shows an individual working channel 295 engaged with the SI joint having two parallel barrels. The additional barrel may facilitate the formation of a second void and the insertion of a second fusion implant or some other fusion device or bone graft material in the second void. As an example, and without limitation, FIG. 121 shows a posterior view of the SI joint having two fusion implants 151 inserted therein. An exposure device having two parallel barrels such as working channel 295 may be used to insert two fusion implants into the SI joint, as shown in FIG. 121.

Figure 122:
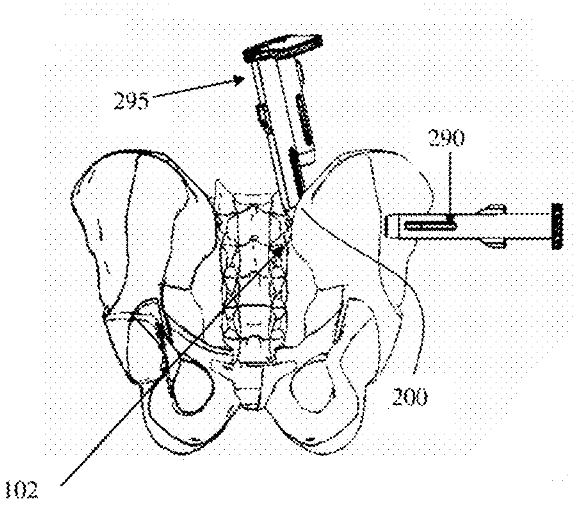
Figure 123:
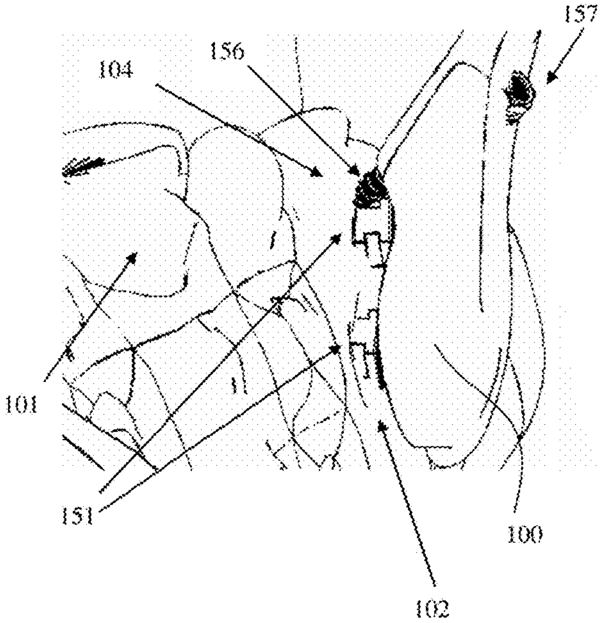
Figure 124:
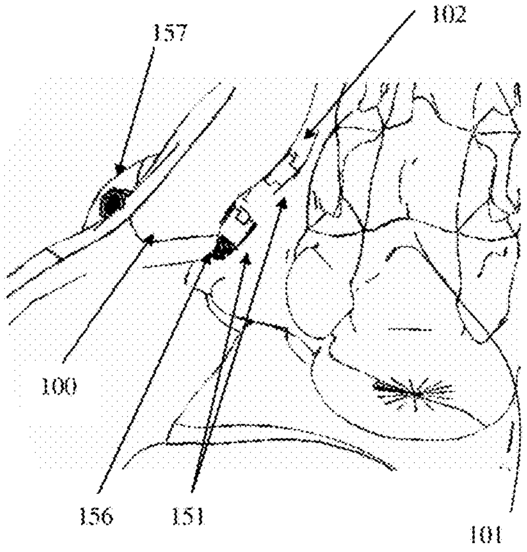

The working channel 295 may be used individually in a SI joint fusion procedure, or in combination with another working channel. For example, and without limiting the invention, FIG. 122 shows an exemplary working channel 290 that may be used in conjunction with the working channel 295, allowing for insertion of a joint fixation device in the ilium and sacrum. The working channels 290 and 295 may also be connected to one another by an adjustable rack, as described above, thereby stabilizing the two working channels and maintaining their orientation relative to one another. It is to be appreciated that working channels having two or more barrels may fixedly attached to a second working channel at an angle by a connecting member, as described in the examples above. As an example, and without limitation, FIGS. 123-124 show posterior and superior views of an SI joint having two fusion implants 151 inserted therein, and a fixation device 157 implanted in the iliac wing 100 and the body of S1 of the sacrum 101. The fusion implants 151 sit in the SI joint 102 between the articular surfaces of the sacrum 101 and the iliac wing 100. The fixation device 157 passes through the iliac wing 100 and into the body of S1 of the sacrum 101 without traversing (passing through) the SI joint 102. An exposure device having two parallel barrels such as working channel 295 may be used to insert two fusion implants into the SI joint, and a second working channel may be used to insert the joint fixation device in the iliac wing and the sacrum, as shown in FIGS. 123-124.

It is also to be appreciated that the individual working channel having two or more barrels are not limited to SI joint fusion procedures, and may have other beneficial applications. Furthermore, the other working channel apparatuses may be useful in other procedures as well. For instance, the working channels of the present invention may be associated with various racks (e.g., having varying lengths and means of attachment) that facilitate procedures where two difficult surgical sites are needed.

Figure 125:
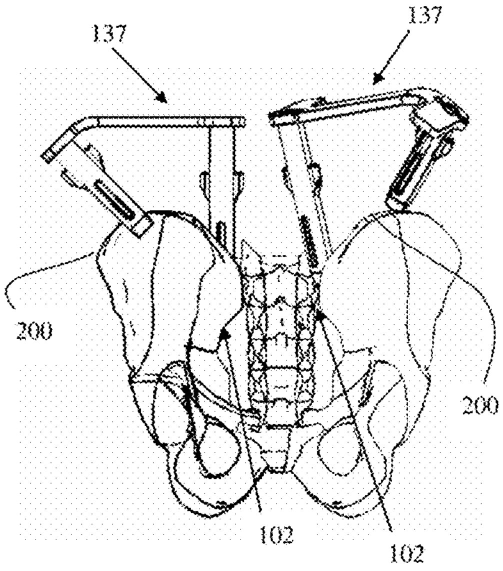
Figure 126:
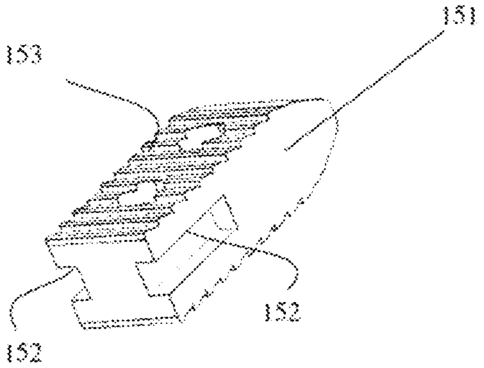
Figure 127:
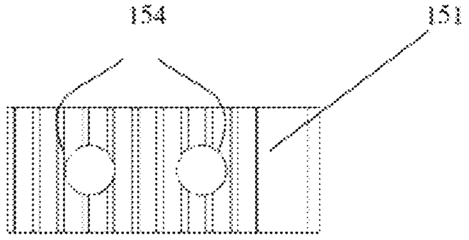
Figure 128:
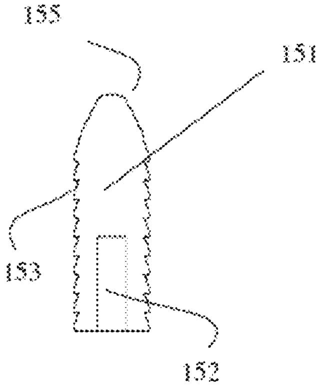

It is to be further appreciated that the working channel apparatuses (exposure devices) described herein can be utilized in SI joint fusion procedures on both SI joints of a patient simultaneously. As shown in FIG. 125, the presently described exposure devices can be utilized in a bilateral SI joint procedure.

The methods described herein may be used to treat both of the patient's SI joints either at the same or approximately the same time (e.g., during the same procedure) or in sequence.

It is to be understood that variations and modifications of the present invention may be made without departing from the scope thereof. It is also to be understood that the present invention is not to be limited by the specific embodiments disclosed herein, but only in accordance with the appended claims when read in light of the foregoing specification.

What is claimed:

1. A method for repairing a patient's sacroiliac joint, said sacroiliac joint including a sacrum and an illium, the method comprising:

a. creating a first incision proximal to the patient's sacroiliac joint;

b. inserting at least one tang on a distal end of a surgical tool into said first incision, said surgical tool having a tapered edge adjacent to said at least one tang;

c. creating a void in said sacroiliac joint;

d. inserting a single fusion implant into said void along a path that is substantially parallel to articular surfaces of the patient's sacroiliac joint, and no further fusion implants are introduced into the patient's sacroiliac joint after the insertion of the single fusion implant, said fusion implant having at least one bone-piercing protrusion for engagement with bone tissue in an articular surface of at least one of the sacrum and the ilium and at least one passage therethrough for holding a fusion promoting material and allowing growth of bone through said at least one passage; and e. rotating the fusion implant within the void, wherein said rotation drives the at least one bone-piercing element into said bone tissue such that said at least on bone-piercing element and penetrates into the bone tissue in an articular surface of at least one of the ilium and the sacrum as the fusion implant is rotated such that the fusion implant spans a joint space between the ilium and the sacrum and articular surfaces of the sacrum and ilium and wherein said fusion implant contacts the ilium and the sacrum and compresses the patient's sacroiliac joint, thereby fixing the ilium and the sacrum in relative lateral positions and securing said fusion implant in the patient's sacroiliac joint.

2. The method of claim 1, further comprising removing cortical tissue from said articular surfaces of said sacrum and said ilium prior to inserting said fusion implant into said void.

3. The method of claim 1, wherein said at least one bone piercing protrusion penetrates and embeds in the cancellous bone tissue of articular surfaces of said sacrum and said ilium as the single fusion implant is rotated, thereby fixing the sacroiliac joint and securing the single fusion implant in the sacroiliac joint.

4. The method of claim 1, further comprising driving said fusion implant into said void, wherein driving said fusion implant engages said at least one bone-piercing protrusion with said bone tissue, wherein said at least one bone-piercing protrusion includes a first bone-piercing protrusion having a first cutting edge at a distal end thereof and said fusion implant includes a second bone-piercing protrusion having a second cutting edge at a distal end thereof, wherein said step of driving said single fusion implant into the void includes positioning said first cutting edge in proximity to an articular surface of said ilium and positioning said second cutting edge in proximity to an articular surface of said sacrum and said step of rotating the single fusion implant or a portion thereof embeds the first and second bone-piercing elements in the articular surfaces of the sacroiliac joint and secure the fusion implant in the sacroiliac joint.

5. The method of claim 1, wherein said fusion implant is configured to substantially fix and fuse the patient's ilium to the patient's sacrum, thereby substantially immobilizing the patient's sacroiliac joint.

* * * * *